United States Patent
Cuero Rengifo et al.

(10) Patent No.: US 11,635,439 B2
(45) Date of Patent: Apr. 25, 2023

(54) BIOLOGICAL DEVICES AND METHODS OF USE THEREOF FOR THE DETECTION OF AMYLOID PROTEINS

(71) Applicant: Bio Capital Holdings, LLC, Houston, TX (US)

(72) Inventors: Raul Cuero Rengifo, Cypress, TX (US); Diana Vasquez Forero, Santander (CO); Juliana Londoño Murillo, Manizales (CO)

(73) Assignee: Bio Capital Holdings, LLC, Houston, TX (US)

( * ) Notice: Subject to any disclaimer, the term of this patent is extended or adjusted under 35 U.S.C. 154(b) by 394 days.

(21) Appl. No.: 16/903,995

(22) Filed: Jun. 17, 2020

(65) Prior Publication Data

US 2021/0011029 A1    Jan. 14, 2021

Related U.S. Application Data

(63) Continuation-in-part of application No. PCT/US2018/065905, filed on Dec. 17, 2018.
(Continued)

(51) Int. Cl.
| | | |
|---|---|---|
| *G01N 33/68* | (2006.01) | |
| *G01N 21/31* | (2006.01) | |
| *G01N 21/39* | (2006.01) | |

(52) U.S. Cl.
CPC ... *G01N 33/6896* (2013.01); *G01N 2021/392* (2013.01); *G01N 2333/4709* (2013.01)

(58) Field of Classification Search
CPC ......... G01N 33/6895; G01N 2021/392; G01N 2333/4709
See application file for complete search history.

(56) References Cited

U.S. PATENT DOCUMENTS

| | | | |
|---|---|---|---|
| 2002/0072596 A1* | 6/2002 | Ruben | ....................... A61P 7/02 435/325 |
| 2006/0183193 A1 | 8/2006 | Horanyi et al. | |

(Continued)

FOREIGN PATENT DOCUMENTS

| | | |
|---|---|---|
| WO | 2013004607 A1 | 1/2013 |
| WO | 2017182634 A1 | 10/2017 |

OTHER PUBLICATIONS

"Human LilrB2 Is a beta-Amyloid Receptor and Its Murine Homolog PirB Regulates Synaptic Plasticity in an Alzheimer's Model", Science, Sep. 20, 2013, vol. 341, No. 6152 by Kim et al (Year: 2013).*

(Continued)

*Primary Examiner* — Jamil Ahmed
(74) *Attorney, Agent, or Firm* — Thomas | Horstemeyer, LLP

(57) ABSTRACT

Described herein are devices and methods for simultaneously expressing amyloid precursor protein and TonB protein. These devices and methods increase the production of these two proteins while also minimizing costs, making the proteins more widely accessible for medical research purposes, including the development of diagnostic tests for numerous diseases associated with elevated production of amyloid proteins. The amyloid precursor protein and TonB produced by the devices and methods described herein, as well as the devices themselves, can be used in experiments designed to model the interactions between metals and amyloids such as β-amyloid that are characteristic of numerous diseases such as Alzheimer's. Finally, provided herein are diagnostic tests that can detect Alzheimer's disease in samples from patients; the tests are sensitive enough to
(Continued)

1➔ Marker (M5000, Epoch Life Science Inc.)
2➔ b-Amyloid Device in pYES2 digested with Hpai and Xbai
(11kb and 3839bp)

identify diseases such as Alzheimer's even at pre-clinical stages, before the appearance of symptoms.

23 Claims, 18 Drawing Sheets

Specification includes a Sequence Listing.

Related U.S. Application Data

(60) Provisional application No. 62/645,691, filed on Mar. 20, 2018, provisional application No. 62/599,849, filed on Dec. 18, 2017.

(56) References Cited

U.S. PATENT DOCUMENTS

| | | | |
|---|---|---|---|
| 2016/0168214 A1* | 6/2016 | Cuero Rengifo | C07K 14/4711 435/254.2 |
| 2018/0024145 A1 | 1/2018 | Sorek et al. | |

OTHER PUBLICATIONS

International Search Report issued for PCT/US2018/065905, dated May 24, 2019.

Kim et al., Human LilrB2 is a Beta-Amyloid Receptor and its Murine Homolog PirB Regulates Synaptic Plasticity in an Alzheimer's Model, Science, vol. 341, No. 6152, p. 1399-1404, 2013.

Genbank, Human mRNA for amyloid A4 precursor of Alzheimer's disease, Retrieved on Apr. 19, 2019, < URL: https://www.ncbi.nlm.nih.gov/nuccore/Y00264.1/> Entire document, 2008.

* cited by examiner

1 ➔ Marker (M5000, Epoch Life Science Inc.)
2 ➔ b-Amyloid Device in pYES2 digested with HpaI and XbaI (11kb and 3839bp)

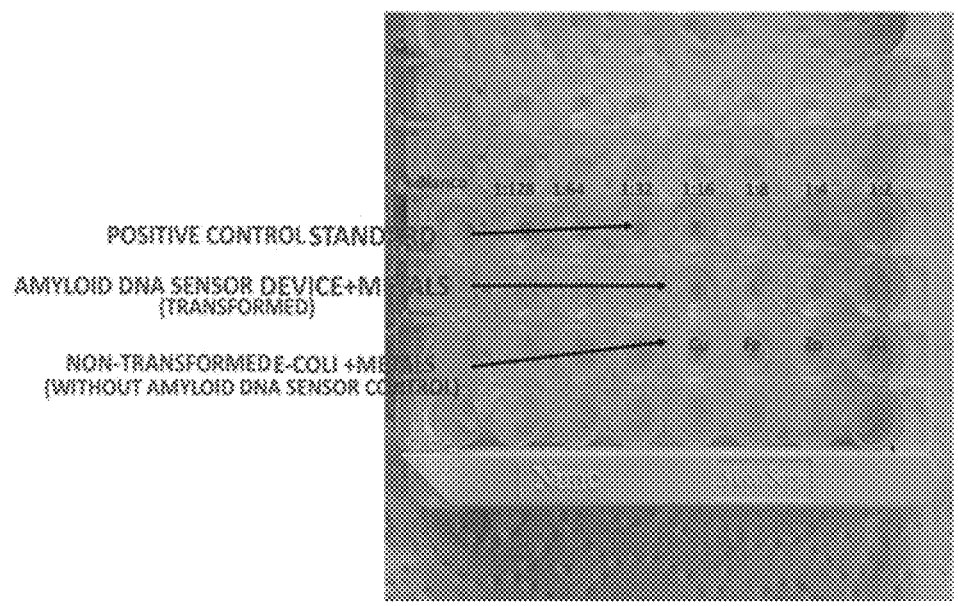
FIGURE 13
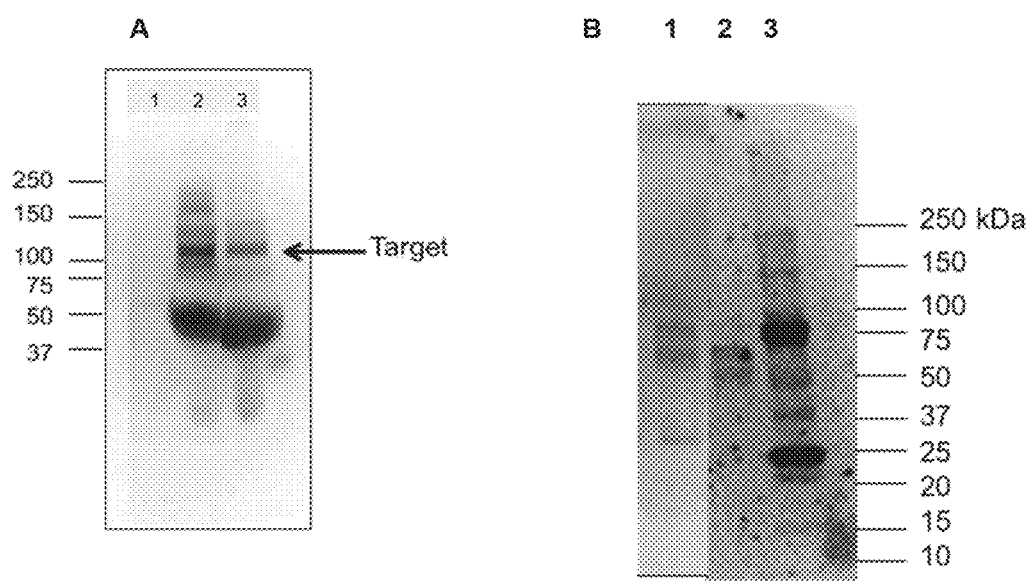
FIGURES 14A-B

SEQUENCE LISTING

```
<160> NUMBER OF SEQ ID NOS: 11

<210> SEQ ID NO 1
<211> LENGTH: 890
<212> TYPE: DNA
<213> ORGANISM: Artificial sequence
<220> FEATURE:
<223> OTHER INFORMATION: Synthetic construct

<400> SEQUENCE: 1
ggattcaaag aggagaaata ctagatggtg agcaagggcg aggagctgtt caccggggtg      60
gtgcccatcc tggtcgagct ggacggcgac gtaaacggcc acaagttcag cgtgtccggc     120
gagggcgagg gcgatgccac ctacggcaag ctgacccctga agttcatctg caccaccggc    180
aagctgcccg tgccctggcc cacccctcgt accaccttcg gctacggcct gcaatgcttc     240
gcccgctacc ccgaccacat gaagctgcac gacttcttca gtccgccat gcccgaaggc      300 tacgtccagg agcgcaccat cttcttcaag gacgacggca actacaagac ccgcgccgag    360
gtgaagttcg agggcgacac cctggtgaac cgcatcgagc tgaagggcat cgacttcaag    420
gaggacggca acatcctggg gcacaagctg gagtacaact acaacagcca caacgtctat    480
atcatggccg acaagcagaa gaacggcatc aaggtgaact tcaagatccg ccacaacatc    540
gaggacggca gcgtgcagct cgccgaccac taccagcaga acacccccat cggcgacggc    600
cccgtgctgc tgcccgacaa ccactacctg agctaccagt ccgccctgag caaagacccc    660
aacgagaagc gcgatcacat ggtcctgctg gagttcgtga ccgccgccgg gatcactctc    720
ggcatggacg agctgtacaa gtaataatac tagagccagg catcaaataa aacgaaaggc    780
tcagtcgaaa gactgggcct ttcgttttat ctgttgtttg tcggtgaacg ctctctacta    840
gagtcacact ggctcacctt cgggtgggcc tttctgcgtt tataaagctt                890

<210> SEQ ID NO 2
<211> LENGTH: 1386
<212> TYPE: DNA
<213> ORGANISM: Artificial sequence
<220> FEATURE:
<223> OTHER INFORMATION: Synthetic construct

<400> SEQUENCE: 2
cctgaggaat tctcactgga acagcgcgtc actcgacagg ccattcttct ccagaatctc      60
ccgcaggcgc ttcagcgcct cgacctggat ctgacgaacc cgctcgcggg tcaggccgat    120
```

```
ttcctggccg  aacctcttcca  gcgtgctgct  ttcgtgaccg  cgcaagccga  agcggcgaat     180
caccacctca  cgctgcttgt  cggtgagttc  cgtcagctgc  tttcgctgag  atcgtcatcc     240
tgcagcagct  cgcacggatc  ggtggggcga  tcgtcggtga  gcgtatccag  cagggtcttg     300
tccgagtccg  gaccaagaga  gacgtctacc  gaagtcaccc  gttcgttcag  gccgagcatg     360
cgcttgacct  cggcgaccgg  cttctccagc  aggttggcga  tttcttcggg  tgaaggttcg     420
tggtcgagct  tgtgggtcag  ttcccgcgcc  gcacgcaggt  agacgttgag  ctccttgacc     480
acatggatcg  gcaagcgaat  ggtccgggtc  tggttcatga  tggcccgctc  gatggtctgg     540
cggatccacc  aggtggcgta  ggtcgagaac  cggaatccgc  gctccggatc  gaacttctcc     600
acggcgcgga  tcaggcctag  gttgccttcc  tcgatcaggt  cgagcaggga  cagtccgcga     660
ttgacatagc  gccgggcgat  cttcaccacc  aaccgcaggt  tgctctcgat  catccgcttc     720
cgaccagcgg  gatcgcccct  ctgcgccaga  cgagcgaagt  ggacttcctc  ttcgggcgtc     780
aacaggggcg  agaaaccgat  tcgttgaga   tacagctgcg  ttgcgtccaa  cgcgcgcgtg     840
tagtcgatgt  gcttgtgttg  tttggaagag  aaggaagtgg  tggcttttgg  agttgcccgg     900
ggagaaggct  gctcgtcggc  agacgactcg  tccagcatga  tgccgggctc  caggaggagc     960
acttcatcat  cgtggtcaaa  ctccggccct  tcttttttga  gtgccatgtc  gttatcccctt    1020 gcatgagttc  gactcaagcc  cgggcgattc  ctttcccgct  ggacacgccc  ggacccgctc    1080
acctacatga  tgtgggcggg  cgaactcccg  gtcagcgacg  tggcaaatat  tgcagtggat    1140
cgacaggctt  accctggcgg  cgaatctcga  agtgcagctt  cacccgatcg  gttcctgtgg    1200
agcccatctc  ggcaatcgat  tgccctacct  tgacctgttg  cccttcccgc  accagcagcc    1260
tgcggttgtg  accgtaggca  ctcacgtagg  tctcgttgtg  tttgatgatg  accaactcgc    1320
cgtagccccg  caaaccacta  ccggcgtata  caacggtccc  accagacgca  gccaggtacc    1380
aagctt                                                                    1386

<210> SEQ ID NO 3
<211> LENGTH: 2102
<212> TYPE: DNA
<213> ORGANISM: Homo sapiens

<400> SEQUENCE: 3
aagcttatgc  tgcccggttt  ggcactgctc  ctgctggccg  cctggacggc  tcgggcgctg      60
gaggtaccca  ctgatggtaa  tgctggcctg  ctggctgaac  cccagattgc  catgttctgt     120
ggcagactga  acatgcacat  gaatgtccag  aatgggaagt  gggattcaga  tccatcaggg     180 accaaaaccct  gcattgatac  caaggaaggc  atcctgcagt  attgccaaga  agtctaccct     240
gaactgcaga  tcaccaatgt  ggtagaagcc  aaccaaccag  tgaccatcca  gaactggtgc     300
aagcggggcc  gcaagcagtg  caagacccat  ccccactttg  tgattcccta  ccgctgctta     360
gttggtgagt  ttgtaagtga  tgcccttctc  gttcctgaca  agtgcaaatt  cttacaccag     420
gagaggatgg  atgtttgcga  aactcatctt  cactggcaca  ccgtcgccaa  agagacatgc     480
agtgagaaga  gtaccaactt  gcatgactac  ggcatgttgc  tgccctgcgg  aattgacaag     540
ttccgagggg  tagagtttgt  gtgttgccca  ctggctgaag  aaagtgacaa  tgtggattct     600
gctgatgcgg  aggaggatga  ctcggatgtc  tggtggggcg  agcagacac   agactatgca     660 gatgggagtg  aagacaaagt  agtagaagta  gcagaggagg  aagaagtggc  tgaggtggaa     720
gaagaagaag  ccgatgatga  cgaggacgat  gaggatggtg  atgaggtaga  ggaagaggct     780
gaggaaccct  acgaagaagc  cacagagaga  accaccagca  ttgccaccac  caccaccacc      840
```

```
accacagagt ctgtggaaga ggtggttcga gttcctacaa cagcagccag tacccctgat      900
gccgttgaca agtatctcga gacacctggg gatgagaatg aacatgccca tttccagaaa      960
gccaaagaga ggcttgaggc caagcaccga gagagaatgt cccaggtcat gagagaatgg     1020
gaagaggcag aacgtcaagc aaagaacttg cctaaagctg ataagaaggc agttatccag     1080
catttccagg agaaagtgga atctttggaa caggaagcag ccaacgagag acagcagctg     1140
gtggagacac acatggccag agtggaagcc atgctcaatg accgccgccg cctggccctg     1200
gagaactaca tcaccgctct gcaggctgtt cctcctcggc tcgtcacgt gttcaatatg      1260 ctaaagaagt atgtccgcgc agaacagaag gacagacagc acaccctaaa gcatttcgag     1320
catgtgcgca tggtggatcc caagaaagcc gctcagatcc ggtcccaggt tatgacacac     1380
ctccgtgtga tttatgagcg catgaatcag tctctctccc tgctctacaa cgtgcctgca     1440
gtggccgagg agattcagga tgaagttgat gagctgcttc agaaagagca aaactattca     1500
gatgacgtct tggccaacat gattagtgaa ccaaggatca gttacggaaa cgatgctctc     1560
atgccatctt tgaccgaaac gaaaaccacc gtggagctcc ttcccgtgaa tggagagttc     1620
agcctggacg atctccagcc gtggcattct ttttggggctg actctgtgcc agccaacaca     1680
gaaaacgaag ttgagcctgt tgatgcccgc cctgctgccg accgaggact gaccactcga     1740
ccaggttctg ggttgacaaa tatcaagacg gaggagatct ctgaagtgaa gatggatgca     1800
gaattccgac atgactcagg atatgaagtt catcatcaaa aattggtgtt ctttgcagaa     1860
gatgtgggtt caaacaaagg tgcaatcatt ggactcatgg tgggcggtgt tgtcatagcg     1920
acagtgatcg tcatcaccct tggtgatgctg aagaagaaac agtacacatc cattcatcat     1980
ggtgtggtgg aggttgacgc cgctgtcacc ccagaggagc gccacctgtc caagatgcag     2040
cagaacggct acgaaaatcc aacctacaag ttctttgagc agatgcagaa ctgagcggcc     2100
gc                                                                    2102

<210> SEQ ID NO 4
<211> LENGTH: 1097
<212> TYPE: DNA
<213> ORGANISM: Artificial sequence
<220> FEATURE:
<223> OTHER INFORMATION: Synthetic construct

<400> SEQUENCE: 4
aagcttctgc agcggccgct actagtagtt aggtgccctg gccgttccca gcattggtgg       60
ccgcggccgt ggccggaccg gcgcccgggg tggcgcccag caccgactgc aggtcaggct      120
tcatcgcctg cagctgcgcg ccccagtagg gccagtcgtg ggtgccgttg gcgtcgaagt      180
tccacaccgc gttgtggccg ccggcgccgt tgtaggcgtc ctggaacttc aggttggacg      240
tccgcacgaa gccctcgagg aacttggcgg gcaggttgtc gccaccgagg tcggacggct      300
tgccgttgcc gcagtacacc cagatccggg tgttgttcgc gaccagcttg ccgacctgca      360
gcgacgggtc gttgcgggcc caggccgggt cctccttcgg accccacatg tcggcggcct      420
tgtagccacc ggcgtcaccc atggccagcc gatcagcga cgggcccatg ccctgcgacg      480
agtccagcag cgccgacagc gagccggcgt agacgaactg gtcggggtgg taggcggcca      540
ggatcagcgc cgaggagccg gccatcgaca ggccgacgac accgctgccg gtcggcttga      600
cctgcttctg cgccgacagg tactgcggca gctcgctggt caggaaggtc tcccacttgt      660
aggtggtgca gccggccttg ccgcaggcgg gcttgtacca gtcggagtag aagctggact      720
```

```
ggccgccgac cggcatggcg accgagatgc ccgactggtt gtaccactcg aacgccgggg    780
tgttgatgtc ccagccgttg aagtcgtctt gcgcgcgcat cccgtcgagc aggtacaacg    840
cgggcgagtt ggccccaccg ctttggaact ggaccttgat gtcccgtccc atggcggcgg    900
agggaacctg caggtactcc accggcagac cggggcgcga aaggccccg gcggtcgccg     960 agccccgac ggcgccaatc aggcccgaga gcagcgccgc accagcggcc cccaccacga     1020
gccggcgcgg catccccgcc acggcgccgc gcaatctgtc gacaagcgtc atctagaagc     1080
ggccgcgaat tcggatc                                                    1097
```

<210> SEQ ID NO 5
<211> LENGTH: 2097
<212> TYPE: DNA
<213> ORGANISM: Gorilla gorilla

<400> SEQUENCE: 5

```
atgcgtctgg ccgttggtgc cctgctggtg tgcgcggtgc tgggcctgtg cctggccgtc    60
ccagataaaa ccgttcgctg gtgcgcagtc agtgagcatg aagcgacgaa gtgccaatct    120
ttccgcgatc acatgaaaag cgtaattccg agcgatggtc cgagtgtagc ttgtgttaag    180
aaagcaagct atctggactg tatccgcgca attcagcgga acgaagctga tgcagttacc    240
ctggacgcag gtctggtttta cgacgcgtac ctggctccta caatctgaa accggttgta    300 gcggagttct atggtagtaa agaagacccg caaactttct attatgcagt ggccgtggta    360
aagaaggact ctggtttttca gatgaaccag ctgcgtggga agaaaagttg tcatacgggc    420
ctggggcgtt ctgcggggttg gaacattcca attgggctgc tgtattgcga tctgccggaa    480
ccacgcaagc cgctggagaa agctgtagcg aacttcttca gtggttcttg tgcgccttgc    540
gccgatggta ctgattttcc gcagctgtgt cagctgtgtc cgggctgcgg ttgttctacc    600
ctgaatcagt actttggcta gtgggggcg tttaaatgcc tgaaagatgg ggcgggtgac    660
gtggcgttcg tcaaacattc tacgattttc gaaaacctgg cgaacaaagc agatcgtgac    720
caatatgaac tgctgtgtct ggacaacact cgcaagccag tcgatgaata taagagttgt    780
catctggcac aagtgcctag tcatactgtg gtcgcgcgta gcattggtgg taaggaggac    840
ctgatttggg aactgctgaa ccaagctcag gagcatttcg gcaaagataa agcaaagaa     900 tttcagctgt tttctagccc gcacggcaaa gacctgctgt ttaaagacag cgcccacggc    960
tttctgaaag tgcctccacg catggatgcc aaaatgtatc tgggttatga atatgttacg    1020
gcaattcgca atctgcgtga aggcacgtgc ccggaagctc cgactgacga gtgcaaacca    1080
gtaaagtggt gtgccctgtc tcatcatgag cgcctgaaat gtgatgaatg gagtgtgaac    1140
tctgttggca aaattgagtg cgttagtgct gaaaccaccg aggactgtat cgcaaagatc    1200
atgaacggcg aagcagatgc tatgtctctg gatggcggtt ttgtgtatat cgcaggtaaa    1260
tgcggcctgg tcccagttct ggctgaaaat tataacaaaa gtgataactg tgaggatact    1320
ccaggggcgg gctattttgc ggtcgctgtc gtcaagaaat ctgcgagcga tctgacatgg    1380
gataacctga agggaagaa atcttgccat accgcggttg ccgcaccgc tgggtggaac     1440 atcccgatgg gcctgctgta taacaaaatc aatcattgcc gttttgacga gttcttcagt    1500
gaggggtgtg cgcctggtag taagaaagat agcagcctgt gcaaactgtg catgggcagc    1560
ggcctgaatc tgtgcgaacc taacaataaa gagggttact acggctacac cggcgcgttt    1620
cgctgcctgc ttgagaaagg tgatgttgcg tttgtaaagc accaaacagt accgcagaat    1680
acgggtggga agaatccgga cccgtgggcc aagaatctga atgaaaagga ttacgaactg    1740
```

```
ctgtgcctgg atgggacccg caagccggtt gaagaatacg cgaattgtca cctggcccgc    1800
gccccgaatc acgccgtggt gacgcgcaaa gataaagagg cctgcgtcca caaaatcctg    1860
cgtcagcagc agcacctgtt cggcagcaat gtgacagatt gtagcggtaa tttctgtctg    1920
ttccgtagcg aaaccaagga cctgctgttc cgtgacgaca ccgtgtgtct ggccaaactg    1980
cacgaccgta ataccctacga gaaatacctg ggcgaggagt acgtgaaagc cgtgggcaat    2040
ctgcgtaagt gtagcacaag cagcctgctg aagcctgca catttcgtcg tccgtaa       2097
```

<210> SEQ ID NO 6
<211> LENGTH: 747
<212> TYPE: DNA
<213> ORGANISM: Pseudomonas entomophila

<400> SEQUENCE: 6

```
gaattcatga cgaaaacgcg ctcgaacatg cgcgctacg gcaccagcct ggccatcgtg    60
ctgggcgtgc acgtggtcgc cgtggtgctg acgctcaact ggtcggtgcc ccaggccatc    120
gagctgccgc cggcagcgat gatggtcgag ttggcgccgt tgccggagcc cgcgccaccg    180
ccaccgccca aggccgcgcc caagccaccg gcagaggtcg aggagccgcc gctgcccaag    240
ctggtggagg cccccaagcc gaagatcgcc atcgccaagc cgcccaagcc caaggccaag    300
ccgcagccgc ccaagcctga aaaaagcct gagccgccga aggacgaacc accgccaag    360 gacgatgtgg cggataccc gccaagcaac gcgcagccgc agaaatcggc cgcaccggca    420
ccgagcatcg cctccaacag caatgccctg cccagctggc agagcgacct gctgcgccac    480
ctggccaagt acaagaagta cccggaagac gctcgccgtc gcggcctgca gggcatcaac    540
cgcctgcgct tcgtggtcga cgccgagggc aaggtagtct cgtactcgct ggccggaggc    600
tcgggcagcg cggcgctgga ccgggcgacc ctggaaatga tccgtcgcgc aggctccgta    660
ccgaagccgc cagcggagct gttgaacaat ggcacgatcg aagtcgtggc gccgttcgtc    720
tattccctgg accgacgctg aggatcc                                        747
```

<210> SEQ ID NO 7
<211> LENGTH: 9944
<212> TYPE: DNA
<213> ORGANISM: Artificial sequence
<220> FEATURE:
<223> OTHER INFORMATION: Synthetic construct

<400> SEQUENCE: 7

```
aagcttaaag aggagaaata ctagatggtg agcaagggcg aggagctgtt caccggggtg    60
gtgcccatcc tggtcgagct ggacggcgac gtaaacggcc acaagttcag cgtgtccggc    120
gagggcgagg gcgatgccac ctacggcaag ctgaccctga agttcatctg caccaccggc    180
aagctgcccg tgccctggcc caccctcgtg accaccttcg gctacggcct gcaatgcttc    240
gcccgctacc ccgaccacat gaagctgcac gacttcttca gtccgccat gcccgaaggc    300 tacgtccagg agcgcaccat cttcttcaag gacgacggca actacaagac ccgcgccgag    360
gtgaagttcg agggcgacac cctggtgaac cgcatcgagc tgaagggcat cgacttcaag    420
gaggacggca acatcctggg gcacaagctg gagtacaact acaacagcca caacgtctat    480
atcatggccg acaagcagaa gaacggcatc aaggtgaact tcaagatccg ccacaacatc    540
gaggacggca gcgtgcagct cgccgaccac taccagcaga acacccccat cggcgacggc    600
cccgtgctgc tgcccgacaa ccactacctg agctaccagt ccgcccctgag caaagacccc    660
```

-continued

```
aacgagaagc gcgatcacat ggtcctgctg gagttcgtga ccgccgccgg gatcactctc     720
ggcatggacg agctgtacaa gtaataatac tagagccagg catcaaataa aacgaaaggc     780
tcagtcgaaa gactgggcct ttcgttttat ctgttgtttg tcggtgaacg ctctctacta     840
gagtcacact ggctcacctt cgggtgggcc tttctgcgtt tataggtacc tcatgtaatt     900
agttatgtca cgcttacatt cacgccctcc ccccacatcc gctctaaccg aaaaggaagg     960
agttagacaa cctgaagtct aggtccctat ttatttttt atagttatgt tagtattaag     1020
aacgttattt atatttcaaa tttttctttt ttttctgtac agacgcgtgt acgcatgtaa     1080
cattatactg aaaaccttgc ttgagaaggt tttgggacgc tcgaaggctt taatttgcga     1140
attcggatta gaagccgccg agcgggtgac agccctccga aggaagactc tcctccgtgc     1200
gtcctcgtct tcaccggtcg cgttcctgaa acgcagatgt gcctcgcgcc gcactgctcc     1260
gaacaataaa gattctacaa tactagcttt tatggttatg aagaggaaaa attggcagta     1320
acctggcccc acaaaccttc aaatgaacga atcaaattaa caaccatagg atgataatgc     1380
gattagtttt ttagccttat ttctggggta attaatcagc gaagcgatga ttttgatct     1440 attaacagat atataaatgc aaaaactgca taaccacttt aactaatact ttcaacattt     1500
tcggtttgta ttacttctta ttcaaatgta ataaagtat caacaaaaaa ttgttaatat     1560
acctctatac tttaacgtca aggagaaaaa accccggatc ggactactag cagctgtaat     1620
acgactcact atagggaata ttaagcttat gctgcccggt ttggcactgc tcctgctggc     1680
cgcctggacg gctcgggcgc tggaggtacc cactgatggt aatgctggcc tgctggctga     1740
accccagatt gccatgttct gtggcagact gaacatgcac atgaatgtcc agaatgggaa     1800
gtgggattca gatccatcag ggaccaaaac ctgcattgat accaaggaag catcctgca     1860 gtattgccaa gaagtctacc ctgaactgca gatcaccaat gtggtagaag ccaaccaacc     1920
agtgaccatc cagaactggt gcaagcgggg ccgcaagcag tgcaagaccc atccccactt     1980
tgtgattccc taccgctgct tagttggtga gtttgtaagt gatgcccttc tcgttcctga     2040
caagtgcaaa ttcttacacc aggagaggat ggatgtttgc gaaactcatc ttcactggca     2100
caccgtcgcc aaagagacat gcagtgagaa gagtaccaac ttgcatgact acggcatgtt     2160
gctgccctgc ggaattgaca agttccgagg ggtagagttt gtgtgttgcc cactggctga     2220
agaaagtgac aatgtggatt ctgctgatgc ggaggaggat gactcggatg tctggtgggg     2280
cggagcagac acagactatg cagatgggag tgaagacaaa gtagtagaag tagcagagga     2340
ggaagaagtg gctgaggtgg aagaagaaga agccgatgat gacgaggacg atgaggatgg     2400
tgatgaggta gaggaagagg ctgaggaacc ctacgaagaa gccacagaga gaaccaccag     2460
cattgccacc accaccacca ccaccacaga gtctgtggaa gaggtggttc gagttcctac     2520
aacagcagcc agtacccctg atgccgttga caagtatctc gagacacctg gggatgagaa     2580
tgaacatgcc catttccaga aagccaaaga gaggcttgag gccaagcacc gagagagaat     2640
gtcccaggtc atgagagaat gggaagaggc agaacgtcaa gcaaagaact tgcctaaagc     2700
tgataagaag gcagttatcc agcatttcca ggagaaagtg gaatctttgg aacaggaagc     2760
agccaacgag agacagcagc tggtggagac acacatggcc agagtggaag ccatgctcaa     2820
tgaccgccgc cgcctggccc tggagaacta catcaccgct ctgcaggctg ttcctcctcg     2880
gcctcgtcac gtgttcaata tgctaaagaa gtatgtccgc gcagaacaga aggacagaca     2940
gcacacccta aagcatttcg agcatgtgcg catggtggat cccaagaaag ccgctcgat     3000 ccggtcccag gttatgacac acctccgtgt gatttatgag cgcatgaatc agtctctctc     3060
```

-continued

```
cctgctctac aacgtgcctg cagtggccga ggagattcag gatgaagttg atgagctgct    3120
tcagaaagag caaaactatt cagatgacgt cttggccaac atgattagtg aaccaaggat    3180
cagttacgga aacgatgctc tcatgccatc tttgaccgaa acgaaaacca ccgtggagct    3240
ccttcccgtg aatggagagt tcagcctgga cgatctccag ccgtggcatt cttttggggc    3300
tgactctgtg ccagccaaca cagaaaacga agttgagcct gttgatgccc gccctgctgc    3360
cgaccgagga ctgaccactc gaccaggttc tgggttgaca aatatcaaga cggaggagat    3420
ctctgaagtg aagatggatg cagaattccg acatgactca ggatatgaag ttcatcatca    3480
aaaattggtg ttctttgcag aagatgtggg ttcaaacaaa ggtgcaatca ttggactcat    3540
ggtgggcggt gttgtcatag cgacagtgat cgtcatcacc ttggtgatgc tgaagaagaa    3600
acagtacaca tccattcatc atggtgtggt ggaggttgac gccgctgtca ccccagagga    3660
gcgccacctg tccaagatgc agcagaacgg ctacgaaaat ccaacctaca agttctttga    3720
gcagatgcag aactgaggta cctcatgtaa ttagttatgt cacgcttaca ttcacgccct    3780
ccccccacat ccgctctaac cgaaaaggaa ggagttagac aacctgaagt ctaggtccct    3840
atttatttt ttatagttat gttagtatta agaacgttat ttatatttca aattttttctt    3900
tttttctgt acagacgcgt gtacgcatgt aacattatac tgaaaaccctt gcttgagaag    3960
gttttgggac gctcgaaggc tttaatttgc gaattctcac tggaacagcg cgtcactcga    4020
caggccattc ttctccagaa tctcccgcag gcgcttcagc gcctcgacct ggatctgacg    4080
aacccgctcg cgggtcaggc cgatttcctg gccgacctct tccagcgtgc tgctttcgtg    4140
accgcgcaag ccgaagcggc gaatcaccac ctcacgctgc ttgtcggtga gttccgtcag    4200
ctgctttcgc tgagatcgtc atcctgcagc agctcgcacg gatcggtggg gcgatcgtcg    4260
gtgagcgtat ccagcagggt cttgtccgag tccggaccaa gagagacgtc taccgaagtc    4320
acccgttcgt tcaggccgag catgcgcttg acctcggcga ccggcttctc cagcaggttg    4380
gcgatttctt cgggtgaagg ttcgtggtcg agcttgtggg tcagttcccg cgccgcacgc    4440
aggtagacgt tgagctcctt gaccacatgg atcggcaagc gaatggtccg ggtctggttc    4500
atgatggccc gctcgatggt ctggcggatc caccaggtgg cgtaggtcga gaaccggaat    4560
ccgcgctccg gatcgaactt ctccacggcg cggatcaggc ctaggttgcc ttcctcgatc    4620
aggtcgagca gggacagtcc gcgattgaca tagcgccggg cgatcttcac caccaaccgc    4680
aggttgctct cgatcatccg cttccgacca gcgggatcgc ccttctgcgc cagacgagcg    4740
aagtggactt cctcttcggg cgtcaacagg ggcgagaaac cgatttcgtt gagatacagc    4800
tgcgttgcgt ccaacgcgcg cgtgtagtcg atgtgcttgt gttgtttgga agagaaggaa    4860
gtggtggctt ttggagttgc ccggggagaa ggctgctcgt cggcagacga ctcgtccagc    4920
atgatgccgg gctccaggag gagcacttca tcatcgtggt caaactccgg cccttctttt    4980
ttgagtgcca tgtcgttatc ccttgcatga gttcgactca gcccgggcg attcctttcc    5040
cgctggacac gcccggaccc gctcacctac atgatgtggg cgggcgaact cccggtcagc    5100
gacgtggcaa atattgcagt ggatcgacag gcttaccctg gcggcgaatc tcgaagtgca    5160
gcttcacccg atcggttcct gtggagccca tctcggcaat cgattgccct accttgacct    5220
gttgcccttc ccgcaccagc agcctgcggt tgtgaccgta ggcactcacg taggtctcgt    5280
tgtgtttgat gatgaccaac tcgccgtagc cccgcaaacc actaccggcg tatacaacgg    5340
tcccaccaga cgcagccagc ggccgctact agtagttagg tgccctggcc gttcccagca    5400
```

```
ttggtggccg cggccgtggc cggaccggcg cccggggtgg cgcccagcac cgactgcagg    5460
tcaggcttca tcgcctgcag ctgcgcgccc cagtagggcc agtcgtgggt gccgttggcg    5520
tcgaagttcc acaccgcgtt gtggccgccg cgccgttgt aggcgtcctg gaacttcagg    5580
ttggacgtcc gcacgaagcc ctcgaggaac ttggcgggca ggttgtcgcc accgaggtcg    5640
gacggcttgc cgttgccgca gtacacccag atccgggtgt tgttcgcgac cagcttgccg    5700
acctgcagcg acgggtcgtt gcgggccag gccgggtcct ccttcggacc ccacatgtcg    5760
gcggccttgt agccaccggc gtcacccatg ccagcccga tcagcgacgg gcccatgccc    5820
tgcgacgagt ccagcagcgc cgacagcgag ccggcgtaga cgaactggtc ggggtggtag    5880
gcggccagga tcagcgccga ggagccggcc atcgacaggc cgacgacacc gctgccggtc    5940
ggcttgacct gcttctgcgc cgacaggtac tgcggcagct cgctggtcag gaaggtctcc    6000
cacttgtagg tggtgcagcc ggccttgccg caggcgggct tgtaccagtc ggagtagaag    6060
ctggactggc cgccgaccgg catggcgacc gagatgccg actggttgta ccactcgaac    6120
gccggggtgt tgatgtccca gccgttgaag tcgtcttgcg cgcgcatccc gtcgagcagg    6180
tacaacgcgg gcgagttggc cccaccgctt tggaactgga ccttgatgtc ccgtcccatg    6240
gcggcggagg gaacctgcag gtactccacc ggcagaccgg ggcgcgagaa ggccccggcg    6300
gtcgccgagc ccccgacggc gccaatcagg cccgagagca cgccgcacc agcggccccc    6360 accacgagcc ggcgcggcat ccccgccacg gcgccgcgca atctgtcgac atgcgtctgg    6420
ccgttggtgc cctgctggtg tgcgcggtgc tgggcctgtg cctggccgtc ccagataaaa    6480
ccgttcgctg gtgcgcagtc agtgagcatg aagcgacgaa gtgccaatct ttccgcgatc    6540
acatgaaaag cgtaattccg agcgatggtc cgagtgtagc ttgtgttaag aaagcaagct    6600
atctggactg tatccgcgca attgcagcga acgaagctga tgcagttacc ctggacgcag    6660
gtctggttta cgacgcgtac ctggctccta acaatctgaa accggttgta gcggagttct    6720
atggtagtaa agaagacccg caaactttct attatgcagt ggccgtggta agaaggact    6780 ctggttttca gatgaaccag ctgcgtggga agaaaagttg tcatacgggc tggggcgtt    6840 ctgcgggttg gaacattcca attgggctgc tgtattgcga tctgccggaa ccacgcaagc    6900
cgctggagaa agctgtagcg aacttcttca gtggttcttg tgcgccttgc gccgatggta    6960
ctgattttcc gcagctgtgt cagctgtgtc cgggctgcgg ttgttctacc ctgaatcagt    7020
actttggcta tagtggggcg tttaaatgcc tgaaagatgg ggcgggtgac gtggcgttcg    7080
tcaaacattc tacgattttc gaaaacctgg cgaacaaagc agatcgtgac caatatgaac    7140
tgctgtgtct ggacaacact cgcaagccag tcgatgaata taaagattgt catctggcac    7200
aagtgcctag tcatactgtg gtcgcgcgta gcattggtgg taaggaggac ctgatttggg    7260
aactgctgaa ccaagctcag gagcatttcg gcaaagataa aagcaaagaa tttcagctgt    7320
tttctagccc gcacggcaaa gacctgctgt ttaaagacag cgcccacggc tttctgaaag    7380
tgcctccacg catggatgcc aaaatgtatc tgggttatga atatgttacg gcaattcgca    7440
atctgcgtga aggcacgtgc ccggaagctc cgactgacga gtgcaaacca gtaaagtggt    7500
gtgccctgtc tcatcatgag cgcctgaaat gtgatgaatg gagtgtgaac tctgttggca    7560
aaattgagtg cgttagtgct gaaaccaccg aggactgtat cgcaaagatc atgaacggcg    7620
aagcagatgc tatgtctctg gatgcggtt ttgtgtatat cgcaggtaaa tgcggcctgg    7680
tcccagttct ggctgaaaat tataacaaaa gtgataactg tgaggatact ccaggggcgg    7740
gctattttgc ggtcgctgtc gtcaagaaat ctgcgagcga tctgacatgg gataacctga    7800
```

```
aagggaagaa atcttgccat accgcggttg gccgcaccgc tgggtggaac atcccgatgg    7860
gcctgctgta taacaaaatc aatcattgcc gttttgacga gttcttcagt gagggggtgtg   7920 cgcctggtag taagaaagat agcagcctgt gcaaactgtg catgggcagc ggcctgaatc    7980
tgtgcgaacc taacaataaa gagggttact acggctacac cggcgcgttt cgctgcctgg    8040
ttgagaaagg tgatgttgcg tttgtaaagc accaaacagt accgcagaat acgggtggga    8100
agaatccgga cccgtgggcc aagaatctga atgaaaagga ttacgaactg ctgtgcctgg    8160
atgggacccg caagccggtt gaagaatacg cgaattgtca cctggcccgc gccccgaatc    8220
acgccgtggt gacgcgcaaa gataaagagg cctgcgtcca caaatcctg cgtcagcagc     8280 agcacctgtt cggcagcaat gtgacagatt gtagcggtaa tttctgtctg ttccgtagcg    8340
aaaccaagga cctgctgttc cgtgacgaca ccgtgtgtct ggccaaactg cacgaccgta    8400
atacctacga gaaatacctg ggcgaggagt acgtgaaagc cgtgggcaat ctgcgtaagt    8460
gtagcacaag cagcctgctg gaagcctgca catttcgtcg tccgtaatca tgtaattagt    8520
tatgtcacgc ttacattcac gccctccccc cacatccgct ctaaccgaaa aggaaggagt    8580
tagacaacct gaagtctagg tccctattta ttttttttata gttatgttag tattaagaac   8640
gttatttata tttcaaattt ttcttttttt tctgtacaga cgcgtgtacg catgtaacat    8700
tatactgaaa accttgcttg agaaggtttt gggacgctcg aaggctttaa tttgccggat    8760
tagaagccgc cgagcgggtg acagccctcc gaaggaagac tctcctccgt gcgtcctcgt    8820
cttcaccggt cgcgttcctg aaacgcagat gtgcctcgcg ccgcactgct ccgaacaata    8880
aagattctac aatactagct tttatggtta tgaagaggaa aaattggcag taacctggcc    8940
ccacaaacct tcaaatgaac gaatcaaatt aacaaccata ggatgataat gcgattagtt    9000
ttttagcctt atttctgggg taattaatca gcgaagcgat gattttttgat ctattaacag   9060 atatataaat gcaaaaactg cataaccact ttaactaata cttttcaacat tttcggtttg   9120 tattacttct tattcaaatg taataaaagt atcaacaaaa aattgttaat ataccctctat   9180 actttaacgt caaggaggaa ttcatgacga aaacgcgctc gaacatggcg cgctacggca    9240
ccagcctggc catcgtgctg ggcgtgcacg tggtcgccgt ggtgctgacg ctcaactggt    9300
cggtgcccca ggccatcgag ctgccgccgg cagcgatgat ggtcgagttg gcgccgttgc    9360
cggagcccgc gccaccgcca ccgcccaagg ccgcgcccaa gccaccggca gaggtcgagg    9420
agccgccgct gcccaagctg gtggaggccc ccaagccgaa gatcgccatc gccaagccgc    9480
ccaagcccaa ggccaagccg cagccgccca agcctgagaa aaagcctgag ccgccgaagg    9540
acgaaccacc ggccaaggac gatgtggcgg ataccccgcc aagcaacgcg cagccgcaga    9600
aatcggccgc accggcaccg agcatcgcct ccaacagcaa tgccctgccc agctggcaga    9660
gcgacctgct gcgccacctg gccaagtaca agaagtaccc ggaagacgct cgccgtcgcg    9720
gcctgcaggg catcaaccgc ctgcgcttcg tggtcgacgc cgagggcaag gtagtctcgt    9780
actcgctggc cggaggctcg ggcagcgcgg cgctggaccg ggcgaccctg gaaatgatcc    9840
gtcgcgcagg ctccgtaccg aagccgccag cggagctgtt gaacaatggc acgatcgaag    9900
tcgtggcgcc gttcgtctat tccctggacc gacgctaatc taga                    9944
```

<210> SEQ ID NO 8
<211> LENGTH: 1797
<212> TYPE: DNA
<213> ORGANISM: Homo sapiens

<400> SEQUENCE: 8

```
atgacaccca tagtgacagt attgatttgt ttaggtttat ccttaggacc tagaactaga      60
gtccaaactg gtactattcc taagccaacc ttatgggctg aacctgacag tgtcattaca     120
cagggttcac ccgtgacatt atcttgtcag ggttctttag aagcccagga atacagattg     180
tatcgtgaga agaaatctgc ttcatggata accaggatta gaccagaatt agttaagaat     240
ggccagttcc acatcccaag tattacctgg gagcataccg gacgttacgg ttgtcagtac     300
tactccagag cacgttggtc cgagttgtct gatcctttag tcttagtgat gacaggagct     360
taccctaagc caactttatc tgcacagcct tcaccagtag tcacaagtgg tggcagagtc     420
actttacaat gcgaatctca ggtagccttt ggtggtttca tcttgtgtaa ggaaggcgaa     480
gatgaacacc cacaatgctt aaacagtcaa ccacacgcaa gaggtagttc tagggcaatc     540
ttctcagtag gaccagtaag tccaaatcgt cgttggtcac atagatgcta tggatacgac     600
ttaaactcac cctatgtctg gtcctcaccc tcagatttgt tagagttgtt ggtcccaggc     660
gtttccaaga accatctttt atccgttcag cctggtcccg taatggcacc aggagagtct     720
ttaaccttac aatgcgtttc tgacgtcggt tatgatagat tcgtgttata caaggaaggc     780
gaacgtgact acgtcaatt gcctggtagg caaccacaag ctggtttgtc acaagccaat     840
ttcactttgg gtccagtgtc taggtcttat ggtggccaat acagatgtta cggtgctcac     900
aatttgagta gtgaatgctc tgcaccctct gacccattag acatcttgat tactggtcaa     960
atacgtggca ctcctttcat ttcagttcaa ccaggtccta cagttgcaag tggtgagaat    1020
gtaactttgt tatgtcaatc ctggagacaa tttcatacat tcttgttgac taaagctggt    1080
gctgctgatg cacctttaag gttaagatcc atacgaat atccaaagta ccaagctgag    1140
ttcccaatgt cacctgttac ttctgctcat gcaggtacat acagatgcta tggttctttg    1200
aactctgatc cttacttatt gagtcaccca tcagaacctt tagaattggt agtatctggt    1260
ccatccatgg gttcatcacc tccacccact ggtcctattt ccactccagc tggacctgaa    1320
gaccaaccat tgacaccaac cggaagtgat ccacagtctg gtttgggtag acacttaggt    1380
gtcgtcatag gaatcttggt cgctgtagtg ttattgttgt tgttattgtt gttattgttc    1440
ttgatattga gacatagaag acaaggtaaa cattggacat caacccagag aaaggcagat    1500
ttccagcatc cagctggagc tgtcggtcct gagcccacag atagaggatt gcagtggaga    1560
tcctctccag ctgccgacgc acaagaagag aatttgtatg cagcagtcaa ggatacacaa    1620
cctgaagatg gtgttgaaat ggataccaga gctgctgcat ctgaggctcc tcaggacgtt    1680
acatacgctc aattacatag tttaacttta agaaggaaag ctaccgagcc acctccatca    1740
caagaaagag aacctccagc agaaccttca atctacgcaa cattagccat tcactaa       1797
```

<210> SEQ ID NO 9
<211> LENGTH: 732
<212> TYPE: DNA
<213> ORGANISM: Artificial sequence
<220> FEATURE:
<223> OTHER INFORMATION: Synthetic construct

<400> SEQUENCE: 9

```
gcggccgcca tgtctaaagg tgaagaatta ttcactggtg ttgtcccaat tttggttgaa      60
ttagatggtg atgttaatgg tcacaaattt tctgtctccg gtgaaggtga aggtgatgct     120
acttacggta aattgacctt aaaatttatt tgtactactg gtaaattgcc agttccatgg     180
ccaaccttag tcactacttt cggttatggt gttcaatgtt ttgctagata cccagatcat     240
```

| | |
|---|---|
| atgaaacaac atgactttt caagtctgcc atgccagaag gttatgttca agaaagaact | 300 |
| atttttttca aagatgacgg taactacaag accagagctg aagtcaagtt tgaaggtgat | 360 |
| accttagtta atagaatcga attaaaaggt attgatttta agaagatgg taacatttta | 420 |
| ggtcacaaat tggaatacaa ctataactct cacaatgttt acatcatggc tgacaaacaa | 480 |
| aagaatggta tcaaagttaa cttcaaaatt agacacaaca ttgaagatgg ttctgttcaa | 540 |
| ttagctgacc attatcaaca aaatactcca attggtgatg gtccagtctt gttaccagac | 600 |
| aaccattact tatccactca atctgcctta tccaaagatc aaacgaaaa gagagaccac | 660 |
| atggtcttgt tagaatttgt tactgctgct ggtattaccc atggtatgga tgaattgtac | 720 |
| aaataatcta ga | 732 |

<210> SEQ ID NO 10
<211> LENGTH: 19766
<212> TYPE: DNA
<213> ORGANISM: Artificial sequence
<220> FEATURE:
<223> OTHER INFORMATION: Synthetic construct

<400> SEQUENCE: 10

| | |
|---|---|
| ttttgagcaa tgtttgtgga agcggtattc gcaatgggaa gctccacccc ggttgataat | 60 |
| cagaaaagcc ccaaaaacag gaagattgta aagcaaata tttaaattgt aaacgttaat | 120 |
| attttgttaa aattcgcgtt aaattttgt taaatcagct cattttttaa cgaatagccc | 180 |
| gaaatcggca aaatccctta taatcaaaa gaatagaccg agataggtt gagtgttgtt | 240 |
| ccagttttcca acaagagtcc actattaaag aacgtggact ccaacgtcaa agggcgaaaa | 300 |
| aggtctatc agggcgatgg cccactacgt gaaccatcac cctaatcaag ttttttgggg | 360 |
| tcgaggtgcc gtaaagcagt aaatcggaag ggtaaacgga tgcccccatt tagagcttga | 420 |
| cggggaaagc cggcgaacgt ggcgagaaag gaagggaaga aagcgaaagg agcgggggct | 480 |
| agggcggtgg gaagtgtagg ggtcacgctg ggcgtaacca ccacacccgc cgcgcttaat | 540 |
| ggggcgctac agggcgcgtg gggatgatcc actagtacgg attagaagcc gccgagcggg | 600 |
| tgacagccct ccgaaggaag actctcctcc gtgcgtcctc gtcttcaccg gtcgcgttcc | 660 |
| tgaaacgcag atgtgcctcg cgccgcactg ctccgaacaa taaagattct acaatactag | 720 |
| cttttatggt tatgaagagg aaaaattggc agtaacctgg ccccacaaac cttcaaatga | 780 |
| acgaatcaaa ttaacaacca taggatgata atgcgattag ttttttagcc ttatttctgg | 840 |
| ggtaattaat cagcgaagcg atgattttg atctattaac agatatataa atgcaaaaac | 900 |
| tgcataacca ctttaactaa actttcaac atttcggtt tgtattactt cttattcaaa | 960 |
| tgtaataaaa gtatcaacaa aaattgtta atatacctct atactttaac gtcaaggaga | 1020 |
| aaaaaccccg gatcggacta ctagcagctg taatacgact cactataggg aatattaagc | 1080 |
| tatgacaccc atagtgacag tattgatttg tttaggttta tccttaggac ctagaactag | 1140 |
| agtccaaact ggtactattc ctaagccaac cttatgggct gaacctgaca gtgtcattac | 1200 |
| acagggttca cccgtgacat tatcttgtca gggttcttta aagcccagg aatacagatt | 1260 |
| gtatcgtgag aagaaatctg cttcatggat aaccaggatt agaccagaat tagttaagaa | 1320 |
| tggccagttc cacatcccaa gtattacctg ggagcatacc ggacgttacg gttgtcagta | 1380 |
| ctactccaga gcacgttggt ccgagttgtc tgatccttta gtcttagtga tgacaggagc | 1440 |
| ttaccctaag ccaactttat ctgcacagcc ttcaccagta gtcacaagtg gtggcagagt | 1500 |

```
cactttacaa tgcgaatctc aggtagcctt tggtggtttc atcttgtgta aggaaggcga    1560
agatgaacac ccacaatgct aaacagtca accacacgca agaggtagtt ctagggcaat    1620
cttctcagta ggaccagtaa gtccaaatcg tcgttggtca catagatgct atggatacga    1680
cttaaactca ccctatgtct ggtcctcacc ctcagatttg ttagagttgt tggtcccagg    1740
cgtttccaag aaaccatctt tatccgttca gcctggtccc gtaatggcac caggagagtc    1800
tttaacctta caatgcgttt ctgacgtcgg ttatgataga ttcgtgttat acaaggaagg    1860
cgaacgtgac ttacgtcaat tgcctggtag gcaaccacaa gctggtttgt cacaagccaa    1920
tttcactttg ggtccagtgt ctaggtctta tggtggccaa tacagatgtt acggtgctca    1980
caatttgagt agtgaatgct ctgcaccctc tgacccatta gacatcttga ttactggtca    2040
aatacgtggc actcctttca tttcagttca accaggtcct acagttgcaa gtggtgagaa    2100
tgtaactttg ttatgtcaat cctggagaca atttcataca ttcttgttga ctaaagctgg    2160
tgctgctgat gcacctttaa ggttaagatc catacacgaa tatccaaagt accaagctga    2220
gttcccaatg tcacctgtta cttctgctca tgcaggtaca tacagatgct atggttcttt    2280
gaactctgat ccttacttat tgagtcaccc atcagaacct ttagaattgg tagtatctgg    2340
tccatccatg ggttcatcac ctccacccac tggtcctatt tccactccag ctggacctga    2400
agaccaacca ttgacaccaa ccggaagtga tccacagtct ggtttgggta gacacttagg    2460
tgtcgtcata ggaatcttgg tcgctgtagt gttattgttg ttgttattgt tgttattgtt    2520
cttgatattg agacatagaa gacaaggtaa acattggaca tcaacccaga gaaaggcaga    2580
tttccagcat ccagctggag ctgtcggtcc tgagcccaca gatagaggat tgcagtggag    2640
atcctctcca gctgccgacg cacaagaaga gaatttgtat gcagcagtca aggatacaca    2700
acctgaagat ggtgttgaaa tggataccag agctgctgca tctgaggctc ctcaggacgt    2760
tacatacgct caattacata gtttaacttt aagaaggaaa gctaccgagc cacctccatc    2820
acaagaaaga gaacctccag cagaaccttc aatctacgca acattagcca ttcactaatc    2880
atgtaattag ttatgtcacg cttacattca cgccctcccc ccacatccgc tctaaccgaa    2940
aaggaaggag ttagacaacc tgaagtctag gtccctattt attttttttat agttatgtta    3000 gtattaagaa cgttatttat atttcaaatt tttctttttt ttctgtacag acgcgtgtac    3060
gcatgtaaca ttatactgaa aaccttgctt gagaaggttt tgggacgctc gaaggcttta    3120
atttgccgga ttagaagccg ccgagcgggt gacagccctc cgaaggaaga ctctcctccg    3180
tgcgtcctcg tcttcaccgg tcgcgttcct gaaacgcaga tgtgcctcgc gccgcactgc    3240
tccgaacaat aaagattcta caatactagc ttttatggtt atgaagagga aaaattggca    3300
gtaacctggc cccacaaacc ttcaaatgaa cgaatcaaat taacaaccat aggatgataa    3360
tgcgattagt tttttagcct tatttctggg gtaattaatc agcgaagcga tgatttttga    3420
tctattaaca gatatataaa tgcaaaaact gcataaccac tttaactaat actttcaaca    3480
ttttcggttt gtattacttc ttattcaaat gtaataaaag tatcaacaaa aaattgttaa    3540
tatacctcta tactttaacg tcaaggagaa gcttgccacc atgtctaaag gtgaagaatt    3600
attcactggt gttgtcccaa ttttggttga attagatggt gatgttaatg gtcacaaatt    3660
ttctgtctcc ggtgaaggtg aaggtgatgc tacttacggt aaaattgacc taaaatttat    3720
ttgtactact ggtaaattgc cagttccatg gccaacctta gtcactactt tcggttatgg    3780
tgttcaatgt tttgctagat acccagatca tatgaaacaa catgacttt tcaagtctgc    3840 catgccagaa ggttatgttc aagaaagaac tatttttttc aaagatgacg gtaactacaa    3900
```

```
gaccagagct gaagtcaagt ttgaaggtga taccttagtt aatagaatcg aattaaaagg    3960
tattgatttt aaagaagatg gtaacatttt aggtcacaaa ttggaataca actataactc    4020
tcacaatgtt tacatcatgg ctgacaaaca aaagaatggt atcaaagtta acttcaaaat    4080
tagacacaac attgaagatg gttctgttca attagctgac cattatcaac aaaatactcc    4140
aattggtgat ggtccagtct tgttaccaga caaccattac ttatccactc aatctgcctt    4200
atccaaagat ccaaacgaaa agagagacca catggtcttg ttagaatttg ttactgctgc    4260
tggtattacc catggtatgg atgaattgta caaataatac tagagccagg catcaaataa    4320
aacgaaaggc tcagtcgaaa gactgggcct tcgttttat ctgttgtttg tcggtgaacg    4380
ctctctacta gagtcacact ggctcacctt cgggtgggcc tttctgcgtt tataggtacc    4440
tcatgtaatt agttatgtca cgcttacatt cacgccctcc ccccacatcc gctctaaccg    4500
aaaaggaagg agttagacaa cctgaagtct aggtccctat ttatttttt atagttatgt    4560 tagtattaag aacgttattt atatttcaaa tttttctttt ttttctgtac agacgcgtgt    4620
acgcatgtaa cattatactg aaaaccttgc ttgagaaggt tttgggacgc tcgaaggctt    4680
taatttgcga attcggatta gaagccgccg agcgggtgac agccctccga aggaagactc    4740
tcctccgtgc gtcctcgtct tcaccggtcg cgttcctgaa acgcagatgt gcctcgcgcc    4800
gcactgctcc gaacaataaa gattctacaa tactagcttt tatggttatg aagaggaaaa    4860
attggcagta acctggcccc acaaaccttc aaatgaacga atcaaattaa caaccatagg    4920
atgataatgc gattagtttt ttagccttat ttctggggta attaatcagc gaagcgatga    4980
tttttgatct attaacagat atataaatgc aaaaactgca taaccacttt aactaatact    5040
ttcaacattt tcggtttgta ttacttctta ttcaaatgta ataaaagtat caacaaaaaa    5100
ttgttaatat acctctatac tttaacgtca aggagaaaaa accccggatc ggactactag    5160
cagctgtaat acgactcact atagggaata ttaagcttat gctgcccggt ttggcactgc    5220
tcctgctggc cgcctggacg gctcgggcgc tggaggtacc cactgatggt aatgctggcc    5280
tgctggctga accccagatt gccatgttct gtggcagact gaacatgcac atgaatgtcc    5340
agaatgggaa gtgggattca gatccatcag ggaccaaaac ctgcattgat accaaggaag    5400
gcatcctgca gtattgccaa gaagtctacc ctgaactgca gatcaccaat gtggtagaag    5460
ccaaccaacc agtgaccatc cagaactggt gcaagcgggg ccgcaagcag tgcaagaccc    5520
atccccactt tgtgattccc taccgctgct tagttggtga gtttgtaagt gatgcccttc    5580
tcgttcctga caagtgcaaa ttcttacacc aggagaggat ggatgtttgc gaaactcatc    5640
ttcactggca caccgtcgcc aaagagacat gcagtgagaa gagtaccaac ttgcatgact    5700
acggcatgtt gctgcctgc ggaattgaca agttccgagg ggtagagttt gtgtgttgcc    5760
cactggctga agaaagtgac aatgtggatt ctgctgatgc ggaggaggat gactcggatg    5820
tctggtgggg cggagcagac acagactatg cagatgggag tgaagacaaa gtagtagaag    5880
tagcagagga ggaagaagtg gctgaggtgg aagaagaaga agccgatgat gacgaggacg    5940
atgaggatgg tgatgaggta gaggaagagg ctgaggaacc ctacgaagaa gcccacagaga    6000 gaaccaccag cattgccacc accaccacca ccaccacaga gtctgtggaa gaggtggttc    6060
gagttcctac aacagcagcc agtaccctg atgccgttga caagtatctc gagacacctg    6120
gggatgagaa tgaacatgcc catttccaga aagccaaaga gaggcttgag gccaagcacc    6180
gagagagaat gtcccaggtc atgagagaat gggaagaggc agaacgtcaa gcaaagaact    6240
```

```
tgcctaaagc tgataagaag gcagttatcc agcatttcca ggagaaagtg gaatctttgg    6300
aacaggaagc agccaacgag agacagcagc tggtggagac acacatggcc agagtggaag    6360
ccatgctcaa tgaccgccgc cgcctggccc tggagaacta catcaccgct ctgcaggctg    6420
ttcctcctcg gcctcgtcac gtgttcaata tgctaaagaa gtatgtccgc gcagaacaga    6480
aggacagaca gcacacccta agcatttcg agcatgtgcg catggtggat cccaagaaag     6540
ccgctcagat ccggtcccag gttatgacac acctccgtgt gatttatgag cgcatgaatc    6600
agtctctctc cctgctctac aacgtgcctg cagtggccga ggagattcag gatgaagttg    6660
atgagctgct tcagaaagag caaaactatt cagatgacgc cttggccaac atgattagtg    6720
aaccaaggat cagttacgga aacgatgctc tcatgccatc tttgaccgaa acgaaaacca    6780
ccgtggagct ccttcccgtg aatggagagt tcagcctgga cgatctccag ccgtggcatt    6840 cttttgggc tgactctgtg ccagccaaca cagaaaacga agttgagcct gttgatgccc     6900
gccctgctgc cgaccgagga ctgaccactc gaccaggttc tgggttgaca aatatcaaga    6960
cggaggagat ctctgaagtg aagatggatg cagaattccg acatgactca ggatatgaag    7020
ttcatcatca aaaattggtg ttctttgcag aagatgtggg ttcaaacaaa ggtgcaatca    7080
ttggactcat ggtgggcggt gttgtcatag cgacagtgat cgtcatcacc ttggtgatgc    7140
tgaagaagaa acagtacaca tccattcatc atggtgtggt ggaggttgac gccgctgtca    7200
ccccagagga gcgccacctg tccaagatgc agcagaacgg ctacgaaaat ccaacctaca    7260
agttctttga gcagatgcag aactgaggta cctcatgtaa ttagttatgt cacgcttaca    7320
ttcacgccct ccccccacat ccgctctaac cgaaaaggaa ggagttagac aacctgaagt    7380
ctaggtccct atttattttt ttatagttat gttagtatta agaacgttat ttatatttca    7440
aattttcctt tttttctgt acagacgcgc gtacgcatgt aacattatac tgaaaacctt     7500
gcttgagaag gttttgggac gctcgaaggc tttaatttgc gaattcggat tagaagccgc    7560
cgagcgggtg acagccctcc gaaggaagac tctcctccgt gcgtcctcgt cttcaccggt    7620
cgcgttcctg aaacgcagat gtgcctcgcg ccgcactgct ccgaacaata agattctac    7680 aatactagct tttatggtta tgaagaggaa aaattggcag taacctggcc ccacaaacct    7740
tcaaatgaac gaatcaaatt aacaaccata ggatgataat gcgattagtt ttttagcctt    7800
atttctgggg taattaatca gcgaagcgat gattttgat ctattaacag atatataaat     7860
gcaaaaactg cataaccact ttaactaata ctttcaacat tttcggtttg tattacttct    7920
tattcaaatg taataaaagt atcaacaaaa aattgttaat atacctctat actttaacgt    7980
caaggagctc ctaggccacc atggtattgt taagggtgtt gatattgtta ttgagtgggg    8040
cagcaggaat gggtggtcag tacggcaacc cattgaacaa atacattcgt cactacgaag    8100
gcttatcata caacgttgat agtttacatc agaagcatca acgtgccaaa cgtgccgtca    8160
gtcatgagga ccaattctta agattagatt tccatgccca cggaagacac ttcaacttaa    8220
ggatgaagag agatacctcc ttgtttagtg acagttcaa ggttgaaact tccaacaaag     8280
tattggacta cgatacttca cacatctaca ctggtcacat ctacggtgag gaaggttctt    8340
tctctcatgg ttccgtcatt gacggaagat ttgaaggatt cattcaaact agaggcggta    8400
cattctatgt tgagccagcc gagaggtaca ttaaggatag aacattgccc tttcattccg    8460
taatctacca tgaggatgat atcaattacc cacacaaata cggtcctcaa ggtggctgcg    8520
ctgatcactc agtatttgag agaatgagga agtatcaaat gaccggtgtt gaagaagtta    8580
ctcaaatacc acaagaggag cacgctgcta acggaccaga gttgttgaga aagaagcgta    8640
```

```
ctacttctgc tgagaagaat acatgtcaat tgtacattca aacagatcac ttattcttta   8700
agtactatgg tacaagagag gccgtgatag cccaaatctc ctcacacgtt aaagctattg   8760
acaccatata ccagactact gatttcagtg gtatacgtaa catttctttc atggtgaaga   8820
gaatcaggat aaacactaca gcagacgaga aagatccaac caatccattc agatttccca   8880
acattggagt agagaagttc ttagaattga atagtgaaca gaatcatgat gactactgtt   8940
tggcttatgt gtttactgat agagactttg atgatggtgt gttgggatta gcatgggttg   9000
gtgcaccctc aggttcatct ggtggtattt gtgagaagtc caaattgtac tctgatggca   9060
agaagaagtc tttgaatact ggcattatca ctgtgcagaa ctatggatca catgtgccac   9120
ccaaagtttc tcatatcact ttcgcacatg aagtaggcca taacttcggt tctcctcatg   9180
attccggtac tgagtgtact cctggagaat ccaagaattt gggccagaaa gagaatggta   9240
actacataat gtacgctagg gctacttccg gtgacaaatt gaacaataac aaattctctt   9300
tgtgctcaat tcgtaacatt tctcaagtgt tagagaagaa gagaaacaat tgtttcgttg   9360
aatcaggtca accaatttgc ggaaatggca tggtggagca gggcgaagaa tgtgactgtg   9420
gttattcaga tcaatgtaag gatgagtgtt gctttgatgc aaatcaaccc gagggtagaa   9480
agtgtaagtt aaagccaggc aagcaatgct ctccaagtca aggaccctgc tgcactgcac   9540
aatgcgcctt taagagtaag tccgagaagt gtagagacga cagtgactgc gctagagaag   9600
gtatctgtaa cggctttacc gcattgtgtc ctgccagtga ccctaagcca aactttaccg   9660
attgtaatcg tcacacccaa gtttgcataa acggacagtg cgctggatct atctgtgaga   9720
agtacggttt ggaagaatgc acttgtgctt cttctgatgg taaagatgat aaagagttgt   9780
gtcatgtctg ttgtatgaag aagatggacc catccacttg tgcatccaca ggttctgttc   9840
aatggtccag acacttctct ggaagaacaa ttacattaca accaggttct ccttgtaatg   9900
atttcagagg ttactgtgac gtgtttatga gatgcagatt ggttgacgct gatggccctt   9960
tggccagatt gaagaaggca atcttctcac ctgaattgta cgagaacatt gccgaatgga  10020
tcgtcgctca ctggtgggct gtcttattga tgggcatcgc cttaatcatg ttgatggctg  10080
gattcattaa gatctgtagt gtacatactc cttcaagtaa tccaaagtta ccacctccca  10140 aaccttgcc tggtactttg aagagaagaa ggcctcctca gccaattcaa cagccacaga  10200
ggcaaagacc tcgtgaatca tatcaaatgg gtcacatgag acgttaatta actcatgtaa  10260
ttagttatgt cacgcttaca ttcacgccct ccccccacat ccgctctaac cgaaaaggaa  10320
ggagttagac aacctgaagt ctaggtccct atttattttt ttatagttat gttagtatta  10380
agaacgttat ttatatttca aatttttctt tttttctgt acagacgcgt gtacgcatgt  10440
aacattatac tgaaaacctt gcttgagaag gttttgggac gctcgaaggc tttaatttgc  10500
gcggccgcta ctagtagtta ggtgccctgg ccgttccag cattggtggc cgcggccgtg  10560
gccggaccgg cgcccggggt ggcgcccagc accgactgca ggtcaggctt catcgcctgc  10620
agctgcgcgc cccagtaggg ccagtcgtgg gtgccgttgg cgtcgaagtt ccacaccgcg  10680
ttgtggccgc cggcgccgtt gtaggcgtcc tggaacttca ggttggacgt ccgcacgaag  10740
ccctcgagga acttggcggg caggttgtcg ccaccgaggt cggacggctt gccgttgccg  10800
cagtacaccc agatccgggt gttgttcgcg accagcttgc cgacctgcag cgacgggtcg  10860
ttgcgggccc aggccgggtc ctccttcgga ccccacatgt cggcggcctt gtagccaccg  10920
gcgtcaccca tggccagccc gatcagcgac gggcccatgc cctgcgacga gtccagcagc  10980
```

```
gccgacagcg agccggcgta gacgaactgg tcggggtggt aggcggccag gatcagcgcc    11040
gaggagccgg ccatcgacag gccgacgaca ccgctgccgg tcggcttgac ctgcttctgc    11100
gccgacaggt actgcggcag ctcgctggtc aggaaggtct cccacttgta ggtggtgcag    11160
ccggccttgc cgcaggcggg cttgtaccag tcggagtaga agctggactg gccgccgacc    11220
ggcatggcga ccgagatgcc cgactggttg taccactcga acgccggggt gttgatgtcc    11280
cagccgttga agtcgtcttg cgcgcgcatc ccgtcgagca ggtacaacgc gggcgagttg    11340
gccccaccgc tttggaactg gaccttgatg tcccgtccca tggcggcgga gggaacctgc    11400
aggtactcca ccggcagacc ggggcgcgag aaggcccccgg cggtcgccga gccccgacg    11460 gcgccaatca ggcccgagag cagcgccgca ccagcggccc ccaccgagag ccggcgcggc    11520
atccccgcca cggcgccgcg caatctgtcg acatgcgtct ggccgttggt gccctgctgg    11580
tgtgcgcggt gctgggcctg tgcctggccg tcccagataa aaccgttcgc tggtgcgcag    11640
tcagtgagca tgaagcgacg aagtgccaat ctttccgcga tcacatgaaa agcgtaattc    11700
cgagcgatgg tccgagtgta gcttgtgtta agaaagcaag ctatctggac tgtatccgcg    11760
caattgcagc gaacgaagct gatgcagtta ccctggacgc aggtctggtt tacgacgcgt    11820
acctggctcc taacaatctg aaaccggttg tagcggagtt ctatggtagt aaagaagacc    11880
cgcaaacttt ctattatgca gtggccgtgg taaagaagga ctctggtttt cagatgaacc    11940
agctgcgtgg gaagaaaagt tgtcatacgg gcctggggcg ttctgcgggt tggaacattc    12000
caattgggct gctgtattgc gatctgccgg aaccacgcaa gccgctggag aaagctgtag    12060
cgaacttctt cagtggttct tgtgcgcctt gcgccgatgg tactgatttt ccgcagctgt    12120
gtcagctgtg tccgggctgc ggttgttcta ccctgaatca gtactttggc tatagtgggg    12180
cgtttaaatg cctgaaagat ggggcgggtg acgtggcgtt cgtcaaacat tctacgattt    12240
tcgaaaacct ggcgaacaaa gcagatcgtg accaatatga actgctgtgt ctggacaaca    12300
ctcgcaagcc agtcgatgaa tataaagatt gtcatctggc acaagtgcct agtcatactg    12360
tggtcgcgcg tagcattggt ggtaaggagg acctgatttg ggaactgctg aaccaagctc    12420
aggagcattt cggcaaagat aaaagcaaag aatttcagct gttttctagc ccgcacggca    12480
aagacctgct gtttaaagac agcgcccacg gctttctgaa agtgcctcca cgcatggatg    12540
ccaaaatgta tctgggttat gaatatgtta cggcaattcg caatctgcgt gaaggcacgt    12600
gcccggaagc tccgactgac gagtgcaaac cagtaaagtg gtgtgccctg tctcatcatg    12660
agcgcctgaa atgtgatgaa tggagtgtga actctgttgg caaaattgag tgcgttagtg    12720
ctgaaaccac cgaggactgt atcgcaaaga tcatgaacgg cgaagcagat gctatgtctc    12780 tggatgcgg ttttgtgtat atcgcaggta aatgcggcct ggtcccagtt ctggctgaaa    12840
attataacaa aagtgataac tgtgaggata ctccaggggc gggctatttt gcggtcgctg    12900
tcgtcaagaa atctgcgagc gatctgacat gggataacct gaaagggaag aaatcttgcc    12960
ataccgcggt tggccgcacc gctgggtgga acatcccgat gggcctgctg tataacaaaa    13020
tcaatcattg ccgttttgac gagttcttca gtgaggggtg tgcgcctggt agtaagaaag    13080
atagcagcct gtgcaaactg tgcatgggca gcggcctgaa tctgtgcgaa cctaacaata    13140 agagggtta ctacggctac accggcgcgt ttcgctgcct ggttgagaaa ggtgatgttg    13200
cgtttgtaaa gcaccaaaca gtaccgcaga atacgggtgg gaagaatccg gacccgtggg    13260
ccaagaatct gaatgaaaag gattacgaac tgctgtgcct ggatgggacc cgcaagccgg    13320
ttgaagaata cgcgaattgt caccctggccc gcgccccgaa tcacgccgtg gtgacgcgca    13380
```

```
aagataaaga ggcctgcgtc cacaaaatcc tgcgtcagca gcagcacctg ttcggcagca    13440
atgtgacaga ttgtagcggt aatttctgtc tgttccgtag cgaaaccaag gacctgctgt    13500
tccgtgacga caccgtgtgt ctggccaaac tgcacgaccg taatacctac gagaaatacc    13560
tgggcgagga gtacgtgaaa gccgtgggca atctgcgtaa gtgtagcaca agcagcctgc    13620
tggaagcctg cacatttcgt cgtccgtaat catgtaatta gttatgtcac gcttacattc    13680
acgccctccc cccacatccg ctctaaccga aaaggaagga gttagacaac ctgaagtcta    13740
ggtccctatt tatttttta tagttatgtt agtattaaga acgttattta tatttcaaat     13800 ttttctttt tttctgtaca gacgcgtgta cgcatgtaac attatactga aaaccttgct     13860
tgagaaggtt ttgggacgct cgaaggcttt aatttgccgg attagaagcc gccgagcggg    13920
tgacagccct ccgaaggaag actctcctcc gtgcgtcctc gtcttcaccg gtcgcgttcc    13980
tgaaacgcag atgtgcctcg cgccgcactg ctccgaacaa taaagattct acaatactag    14040
cttttatggt tatgaagagg aaaaattggc agtaacctgg ccccacaaac cttcaaatga    14100
acgaatcaaa ttaacaacca taggatgata atgcgattag ttttttagcc ttatttctgg    14160
ggtaattaat cagcgaagcg atgattttg atctattaac agatatataa atgcaaaaac     14220
tgcataacca cttaactaa tactttcaac attttcggtt tgtattactt cttattcaaa     14280
tgtaataaaa gtatcaacaa aaattgtta atatacctct atactttaac gtcaaggagg     14340
aattcatgac gaaaacgcgc tcgaacatgg cgcgctacgg caccagcctg gccatcgtgc    14400
tgggcgtgca cgtggtcgcc gtggtgctga cgctcaactg gtcggtgccc caggccatcg    14460
agctgccgcc ggcagcgatg atggtcgagt tggcgccgtt gccggagccc gcgccaccgc    14520
caccgcccaa ggccgcgccc aagccaccgg cagaggtcga ggagccgccg ctgcccaagc    14580
tggtggaggc ccccaagccg aagatcgcca tcgccaagcc gcccaagccc aaggccaagc    14640
cgcagccgcc caagcctgag aaaaagcctg agccgccgaa ggacgaacca ccggccaagg    14700
acgatgtggc ggataccccg ccaagcaacg cgcagccgca gaaatcggcc gcaccggcac    14760
cgagcatcgc ctccaacagc aatgccctgc ccagctggca gagcgacctg ctgcgccacc    14820
tggccaagta caagaagtac ccggaagacg ctcgccgtcg cggcctgcag ggcatcaacc    14880
gcctgcgctt cgtggtcgac gccgagggca aggtagtctc gtactcgctg gccggaggct    14940
cgggcagcgc ggcgctggac cgggcgaccc tggaaatgat ccgtcgcgca ggctccgtac    15000
cgaagccgcc agcggagctg ttgaacaatg gcacgatcga agtcgtggcg ccgttcgtct    15060
attccctgga ccgacgctaa tctagagggc cgcatcatgt aattagttat gtcacgctta    15120
cattcacgcc ctcccccac atccgctcta accgaaaagg aaggagttag acaacctgaa     15180
gtctaggtcc ctatttattt ttttatagtt atgttagtat taagaacgtt atttatattt    15240 caaatttc ttttttttct gtacagacgc gtgtacgcat gtaacattat actgaaaacc     15300
ttgcttgaga aggttttggg acgctcgaag gctttaattt gcggcctgc attaatgaat     15360 cggccaacgc gcgggagag gcggtttgcg tattgggcgc tcttccgctt cctcgctcac     15420
tgactcgctg cgctcggtcg ttcggctgcg gcgagcggta tcagctcact caaaggcggt    15480
aatacggtta tccacagaat caggggataa cgcaggaaag aacatgtgag caaaaggcca    15540
gcaaaagccc aggaaccgta aaaaggccgc gttgctggcg ttttccata ggctccgccc     15600 ccctgacgag catcacaaaa atcgacgctc aagtcagagg tggcgaaacc cgacaggact    15660
ataaagatac caggcgtttc ccctggaag ctccctcgtg cgctctcctg ttccgaccct     15720
```

```
gccgcttacc ggatacctgt ccgcctttct cccttcggga agcgtggcgc tttctcatag   15780
ctcacgctgt aggtatctca gttcggtgta ggtcgttcgc tccaagctgg gctgtgtgca   15840 cgaaccccccc gttcagcccg accgctgcgc cttatccggt aactatcgtc ttgagtccaa   15900
cccggtaaga cacgacttat cgccactggc agcagccact ggtaacagga ttagcagagc   15960
gaggtatgta ggcggtgcta cagagttctt gaagtggtgg cctaactacg gctacactag   16020
aaggacagta tttggtatct gcgctctgct gaagccagtt accttcggaa aaagagttgg   16080
tagctcttga tccggcaaac aaaccaccgc tggtagcggt ggttttttg tttgcaagca    16140 gcagattacg cgcagaaaaa aaggatctca agaagatcct ttgatctttt ctacggggtc   16200
tgacgctcag tggaacgaaa actcacgtta agggattttg gtcatgagat tatcaaaaag   16260
gatcttcacc tagatccttt taaattaaaa atgaagtttt aaatcaatct aaagtatata   16320
tgagtaaact tggtctgaca gttaccaatg cttaatcagt gaggcaccta tctcagcgat   16380
ctgtctattt cgttcatcca tagttgcctg actccccgtc gtgtagataa ctacgatacg   16440
ggagcgctta ccatctggcc ccagtgctgc aatgataccg cgagacccac gctcaccggc   16500
tccagattta tcagcaataa accagccagc cggaagggcc gagcgcagaa gtggtcctgc   16560
aactttatcc gcctccattc agtctattaa ttgttgccgg gaagctagag taagtagttc   16620
gccagttaat agtttgcgca acgttgttgg cattgctaca ggcatcgtgg tgtcactctc   16680
gtcgtttggt atggcttcat tcagctccgg ttcccaacga tcaaggcgag ttacatgatc   16740
ccccatgttg tgcaaaaaag cggttagctc cttcggtcct ccgatcgttg tcagaagtaa   16800
gttggccgca gtgttatcac tcatggttat ggcagcactg cataattctc ttactgtcat   16860
gccatccgta agatgctttt ctgtgactgg tgagtactca accaagtcat tctgagaata   16920
gtgtatgcgg cgaccgagtt gctcttgccc ggcgtcaata cgggataata gtgtatcaca   16980
tagcagaact ttaaaagtgc tcatcattgg aaaacgttct cggggcgaaa actctcaag    17040 gatcttaccg ctgttgagat ccagttcgat gtaaccccact cgtgcaccca actgatcttc   17100
agcatctttt actttcacca gcgtttctgg gtgagcaaaa acaggaaggc aaaatgccgc   17160
aaaaaaggga ataagggcga cacggaaatg ttgaatactc atactcttcc ttttcaatg    17220 ggtaataact gatataatta aattgaagct ctaatttgtg agtttagtat acatgcattt   17280
acttataata cagtttttta gttttgctgg ccgcatcttc tcaaatatgc ttcccagcct   17340
gcttttctgt aacgttcacc ctctacctta gcatcccttc cctttgcaaa tagtcctctt   17400
ccaacaataa taatgtcaga tcctgtagag accacatcat ccacggttct atactgttga   17460
cccaatgcgt ctcccttgtc atctaaaccc acaccgggtg tcataatcaa ccaatcgtaa   17520
ccttcatctc ttccacccat gtctctttga gcaataaagc cgataacaaa tctttgtcg    17580 ctcttcgcaa tgtcaacagt acccttagta tattctccag tagataggga gcccttgcat   17640
gacaattctg ctaacatcaa aaggcctcta ggttcctttg ttacttcttc tgccgcctgc   17700
ttcaaaccgc taacaatacc tgggcccacc acaccgtgtg cattcgtaat gtctgcccat   17760
tctgctattc tgtatacacc cgcagagtac tgcaatttga ctgtattacc aatgtcagca   17820
aattttctgt cttcgaagag taaaaaattg tacttggcgg ataatgcctt agcggcttca   17880
actgtgccct ccatggaaaa atcagtcaag atatccacat gtgtttttag taaacaaatt   17940
ttgggaccta atgcttcaac taactccagt aattccttgg tggtacgaac atccaatgaa   18000
gcacacaagt ttgtttgctt ttcgtgcatg atattaaata gcttggcagc aacaggacta   18060
ggatgagtag cagcacgttc cttatatgta gctttcgaca tgatttatct tcgtttcctg   18120
```

```
caggtttttg ttctgtgcag ttgggttaag aatactgggc aatttcatgt ttcttcaaca    18180
ctacatatgc gtatatatac caatctaagt ctgtgctcct tccttcgttc ttccttctgt    18240
tcggagatta ccgaatcaaa aaatttcaa agaaaccgaa atcaaaaaaa agaataaaaa      18300
aaaaatgatg aattgaattg aaaagctagc ttatcgatga taagctgtca aagatgagaa    18360
ttaattccac ggactataga ctatactaga tactccgtct actgtacgat acacttccgc    18420
tcaggtcctt gtcctttaac gaggccttac cactcttttg ttactctatt gatccagctc    18480
agcaaaggca gtgtgatcta agattctatc ttcgcgatgt agtaaaacta gctagaccga    18540
gaaagagact agaaatgcaa aaggcacttc tacaatggct gccatcatta ttatccgatg    18600
tgacgctgca gcttctcaat gatattcgaa tacgctttga ggagatacag cctaatatcc    18660
gacaaactgt tttacagatt tacgatcgta cttgttaccc atcattgaat tttgaacatc    18720
cgaacctggg agttttccct gaaacagata gtatatttga acctgtataa taatatatag    18780
tctagcgctt tacggaagac aatgtatgta tttcggttcc tggagaaact attgcatcta    18840
ttgcataggt aatcttgcac gtcgcatccc cggttcattt tctgcgtttc catcttgcac    18900
ttcaatagca tatctttgtt aacgaagcat ctgtgcttca ttttgtagaa caaaaatgca    18960
acgcgagagc gctaattttt caaacaaaga atctgagctg cattttaca gaacagaaat     19020 gcaacgcgaa agcgctatt taccaacgaa gaatctgtgc ttcatttttg taaaacaaaa     19080
atgcaacgcg acgagagcgc taattttca aacaaagaat ctgagctgca tttttacaga     19140
acagaaatgc aacgcgagag cgctatttta ccaacaaaga atctatactt cttttttgtt    19200
ctacaaaaat gcatcccgag agcgctattt ttctaacaaa gcatcttaga ttactttttt    19260
tctcctttgt gcgctctata atgcagtctc ttgataactt tttgcactgt aggtccgtta    19320
aggttagaag aaggctactt tggtgtctat tttctcttcc ataaaaaaag cctgactcca    19380
cttcccgcgt ttactgatta ctagcgaagc tgcgggtgca ttttttcaag ataaaggcat    19440
ccccgattat attctatacc gatgtggatt gcgcatactt tgtgaacaga aagtgatagc    19500
gttgatgatt cttcattggt cagaaaatta tgaacggttt cttctatttt gtctctatat    19560
actacgtata ggaaatgttt acattttcgt attgttttcg attcactcta tgaatagttc    19620
ttactacaat ttttttgtct aaagagtaat actagagata aacataaaaa atgtagaggt    19680
cgagtttaga tgcaagttca aggagcgaaa ggtggatggg taggttatat agggatatag    19740
cacagagata tatagcaaag agatac                                          19766

<210> SEQ ID NO 11
<211> LENGTH: 13883
<212> TYPE: DNA
<213> ORGANISM: Artificial Sequence
<220> FEATURE:
<223> OTHER INFORMATION: Synthetic Construct

<400> SEQUENCE: 11
ggggaattgt gagcggataa caattcccct ctagaaataa ttttgtttaa ctttaagaag      60
gagatatacc atggtgagca agggcgagga gctgttcacc ggggtggtgc ccatcctggt    120
cgagctggac ggcgacgtaa acggccacaa gttcagcgtg tccggcgagg gcgagggcga    180
tgccacctac ggcaagctga ccctgaagtt catctgcacc accggcaagc tgcccgtgcc    240
ctggcccacc ctcgtgacca ccctgaccta cggcgtgcag tgcttcagcc gctaccccga    300
ccacatgaag cagcacgact tcttcaagtc cgccatgccc gaaggctacg tccaggagcg    360
```

```
caccatcttc ttcaaggacg acggcaacta caagacccgc gccgaggtga agttcgaggg    420
cgacaccctg gtgaaccgca tcgagctgaa gggcatcgac ttcaaggagg acggcaacat    480
cctgggcac aagctggagt acaactacaa cagccacaac gtctatatca tggccgacaa    540
gcagaagaac ggcatcaagg tgaacttcaa gatccgccac aacatcgagg acggcagcgt    600
gcagctcgcc gaccactacc agcagaacac ccccatcggc gacggccccg tgctgctgcc    660
cgacaaccac tacctgagca cccagtccgc cctgagcaaa gaccccaacg agaagcgcga    720
tcacatggtc ctgctggagt tcgtgaccgc cgccgggatc actctcggca tggacgagct    780
gtacaagtaa ggatccagaa ataattttgt ttaactttaa gaaggagaga attcatgaca    840
cccatagtga cagtattgat tgtttaggt ttatccttag gacctagaac tagagtccaa    900
actggtacta ttcctaagcc aaccttatgg gctgaacctg acagtgtcat tacacagggt    960
tcacccgtga cattatcttg tcagggttct ttagaagccc aggaatacag attgtatcgt   1020
gagaagaaat ctgcttcatg gataaccagg attagaccag aattagttaa gaatggccag   1080
ttccacatcc caagtattac ctgggagcat accggacgtt acggttgtca gtactactcc   1140
agagcacgtt ggtccgagtt gtctgatcct ttagtcttag tgatgacagg agcttaccct   1200
aagccaactt tatctgcaca gccttcacca gtagtcacaa gtggtggcag agtcactta   1260
caatgcgaat ctcaggtagc ctttggtggt ttcatcttgt gtaaggaagg cgaagatgaa   1320
cacccacaat gcttaaacag tcaaccacac gcaagaggta gttctagggc aatcttctca   1380
gtaggaccag taagtccaaa tcgtcgttgg tcacatagat gctatggata cgacttaaac   1440
tcaccctatg tctggtcctc accctcagat ttgttagagt gttggtccc aggcgtttcc   1500
aagaaaccat ctttatccgt tcagcctggt cccgtaatgg caccaggaga gtctttaacc   1560
ttacaatgcg tttctgacgt cggttatgat agattcgtgt tatacaagga aggcgaacgt   1620
gacttacgtc aattgcctgg taggcaacca caagctggtt tgtcacaagc caatttcact   1680
ttgggtccag tgtctaggtc ttatggtggc aatacagat gttacggtgc tcacaatttg   1740
agtagtgaat gctctgcacc ctctgaccca ttagacatct tgattactgg tcaaatacgt   1800
ggcactcctt tcatttcagt tcaaccaggt cctacagttg caagtggtga aatgtaact   1860
ttgttatgtc aatcctggag acaatttcat acattcttgt tgactaaagc tggtgctgct   1920
gatgcacctt taaggttaag atccatacac gaatatccaa agtaccaagc tgagttccca   1980
atgtcacctg ttacttctgc tcatgcaggt acatacagat gctatggttc tttgaactct   2040
gatccttact tattgagtca cccatcagaa cctttagaat tggtagtatc tggtccatcc   2100
atgggttcat cacctccacc cactggtcct attccactc cagctggacc tgaagaccaa   2160
ccattgacac caaccggaag tgatccacag tctggtttgg gtagacactt aggtgtcgtc   2220
ataggaatct tggtcgctgt agtgttattg ttgttgttat tgttgttatt gttcttgata   2280
ttgagacata aagacaagg taaacattgg acatcaaccc agagaaaggc agatttccag   2340
catccagctg gagctgtcgg tcctgagccc acagatagag gattgcagtg gagatcctct   2400
ccagctgccg acgcacaaga agagaatttg tatgcagcag tcaaggatac acaacctgaa   2460
gatggtgttg aaatggatac cagagctgct gcatctgagg ctcctcagga cgttacatac   2520
gctcaattac atagtttaac tttaagaagg aaagctaccg agccacctcc atcacaagaa   2580
agagaacctc cagcagaacc ttcaatctac gcaacattag ccattcacta agtcgacaga   2640
aataattttg tttaacttta agaaggagaa agcttatgct gcccgggttg gcactgctcc   2700
tgctggccgc ctggacggct cgggcgctgg aggtacccac tgatggtaat gctggcctgc   2760
```

```
tggctgaacc ccagattgcc atgttctgtg gcagactgaa catgcacatg aatgtccaga    2820
atgggaagtg ggattcagat ccatcaggga ccaaaacctg cattgatacc aaggaaggca    2880
tcctgcagta ttgccaagaa gtctaccctg aactgcagat caccaatgtg gtagaagcca    2940
accaaccagt gaccatccag aactggtgca agcggggccg caagcagtgc aagacccatc    3000
cccactttgt gattccctac cgctgcttag ttggtgagtt tgtaagtgat gcccttctcg    3060
ttcctgacaa gtgcaaattc ttacaccagg agggatgga tgtttgcgaa actcatcttc    3120
actggcacac cgtcgccaaa gagacatgca gtgagaagag taccaacttg catgactacg    3180
gcatgttgct gccctgcgga attgacaagt tccgaggggt agagtttgtg tgttgcccac    3240
tggctgaaga aagtgacaat gtggattctg ctgatgcgga ggaggatgac tcggatgtct    3300
ggtggggcgg agcagacaca gactatgcag atgggagtga agacaaagta gtagaagtag    3360
cagaggagga agaagtggct gaggtggaag aagaagaagc cgatgatgac gaggacgatg    3420
aggatggtga tgaggtagag gaagaggctg aggaaccct a cgaagaagcc acagagagaa    3480
ccaccagcat tgccaccacc accaccacca ccacagagtc tgtggaagag gtggttcgag    3540
ttcctacaac agcagccagt accccctgatg ccgttgacaa gtatctcgag acacctgggg    3600
atgagaatga acatgcccat ttccagaaag ccaaagagag gcttgaggcc aagcaccgag    3660
agagaatgtc ccaggtcatg agagaatggg aagaggcaga acgtcaagca aagaacttgc    3720
ctaaagctga taagaaggca gttatccagc atttccagga gaaagtggaa tctttggaac    3780
aggaagcagc caacgagaga cagcagctgg tggagacaca catggccaga gtggaagcca    3840
tgctcaatga ccgccgccgc ctggccctgg agaactacat caccgctctg caggctgttc    3900
ctcctcggcc tcgtcacgtg ttcaatatgc taaagaagta tgtccgcgca gaacagaagg    3960
acagacagca caccctaaag catttcgagc atgtgcgcat ggtggatccc aagaaagccg    4020
ctcagatccg gtcccaggtt atgacacacc tccgtgtgat ttatgagcgc atgaatcagt    4080
ctctctccct gctctacaac gtgcctgcag tggccgagga gattcaggat gaagttgatg    4140
agctgcttca gaaagagcaa aactattcag atgacgtctt ggccaacatg attagtgaac    4200
caaggatcag ttacggaaac gatgctctca tgccatcttt gaccgaaacg aaaaccaccg    4260
tggagctcct tcccgtgaat ggagagttca gcctggacga tctccagccg tggcattctt    4320
ttggggctga ctctgtgcca gccaacacag aaaacgaagt tgagcctgtt gatgcccgcc    4380
ctgctgccga ccgaggactg accactcgac caggttctgg gttgacaaat atcaagacgg    4440
aggagatctc tgaagtgaag atggatgcag aattccgaca tgactcagga tatgaagttc    4500
atcatcaaaa attggtgttc tttgcagaag atgtgggttc aaacaaaggt gcaatcattg    4560
gactcatggt gggcggtgtt gtcatagcga cagtgatcgt catcaccttg gtgatgctga    4620
agaagaaaca gtacacatcc attcatcatg gtgtggtgga ggttgacgcc gctgtcaccc    4680
cagaggagcg ccacctgtcc aagatgcagc agaacggctc cgaaaatcca acctacaagt    4740
tctttgagca gatgcagaac tgagcggccg cataatgctt aagtcgaaca gaaagtaatc    4800
gtattgtaca cggccgcata atcgaaatta atacgactca ctataggga attgtgagcg    4860 gataacaatt cccatctta gtatattagt taagtataag aaggagatat acatatgact    4920
agtagttagg tgccctggcc gttcccagca ttggtggccg cggccgtggc cggaccggcg    4980
cccggggtgg cgcccagcac cgactgcagg tcaggcttca tcgcctgcag ctgcgcgccc    5040
cagtagggcc agtcgtgggt gccgttggcg tcgaagttcc acaccgcgtt gtggccgccg    5100
```

```
gcgccgttgt aggcgtcctg gaacttcagg ttggacgtcc gcacgaagcc ctcgaggaac    5160
ttggcgggca ggttgtcgcc accgaggtcg gacggcttgc cgttgccgca gtacacccag    5220
atccgggtgt tgttcgcgac cagcttgccg acctgcagcg acgggtcgtt gcgggcccag    5280
gccgggtcct ccttcggacc ccacatgtcg gcggccttgt agccaccggc gtcacccatg    5340
gccagcccga tcagcgacgg gcccatgccc tgcgacgagt ccagcagcgc cgacagcgag    5400
ccggcgtaga cgaactggtc ggggtggtag gcggccagga tcagcgccga ggagccggcc    5460
atcgacaggc cgacgacacc gctgccggtc ggcttgacct gcttctgcgc cgacaggtac    5520
tgcggcagct cgctggtcag gaaggtctcc cacttgtagg tggtgcagcc ggccttgccg    5580
caggcgggct tgtaccagtc ggagtagaag ctggactggc cgccgaccgg catggcgacc    5640
gagatgcccg actggttgta ccactcgaac gccggggtgt tgatgtccca gccgttgaag    5700
tcgtcttgcg cgcgcatccc gtcgagcagg tacaacgcgg gcgagttggc cccaccgctt    5760
tggaactgga ccttgatgtc ccgtcccatg gcggcggagg gaacctgcag gtactccacc    5820
ggcagaccgg ggcgcgagaa ggccccgcg gtcgccgagc ccccgacggc gccaatcagg     5880
cccgagagca gcgccgcacc agcggccccc accacgagcc ggcgcggcat ccccgccacg    5940
gcgccgcgca atctgtcgac aagcgtcatc tagatctaga aataattttg tttaacttta    6000
agaaggagag atatcatgcg tctggccgtt ggtgccctgc tggtgtgcgc ggtgctgggc    6060
ctgtgcctgg ccgtcccaga taaaaccgtt cgctggtgcg cagtcagtga gcatgaagcg    6120
acgaagtgcc aatctttccg cgatcacatg aaaagcgtaa ttccgagcga tggtccgagt    6180
gtagcttgtg ttaagaaagc aagctatctg gactgtatcc gcgcaattgc agcgaacgaa    6240
gctgatgcag ttaccctgga cgcaggtctg gtttacgacg cgtacctggc tcctaacaat    6300
ctgaaaccgt tgtagcggaa gttctatggt agtaaagaag acccgcaaac tttctattat    6360
gcagtggccg tggtaaagaa ggactctggt tttcagatga accagctgcg tgggaagaaa    6420
agttgtcata cgggcctggg gcgttctgcg ggttggaaca ttccaattgg gctgctgtat    6480
tgcgatctgc cggaaccacg caagccgctg gagaaagctg tagcgaactt cttcagtggt    6540
tcttgtgcgc cttgcgccga tggtactgat ttttccgcagc tgtgtcagct gtgtccgggc    6600
tgcggttgtt ctaccctgaa tcagtacttt ggctatagtg gggcgtttaa atgcctgaaa    6660
gatggggcgg gtgacgtggc gttcgtcaaa cattctacga ttttcgaaaa cctggcgaac    6720
aaagcagatc gtgaccaata tgaactgctg tgtctggaca cactcgcaa gccagtcgat     6780 gaatataaag attgtcatct ggcacaagtg cctagtcata ctgtggtcgc gcgtagcatt    6840
ggtggtaagg aggacctgat ttgggaactg ctgaaccaag ctcaggagca tttcggcaaa    6900
gataaaagca agaatttca gctgttttct agcccgcacg gcaaagacct gctgtttaaa    6960
gacagcgccc acggctttct gaaagtgcct ccacgcatgg atgccaaaat gtatctgggt    7020
tatgaatatg ttacggcaat tcgcaatctg cgtgaaggca cgtgcccgga agctccgact    7080
gacgagtgca aaccagtaaa gtggtgtgcc ctgtctcatc atgagcgcct gaaatgtgat    7140
gaatggagtg tgaactctgt tggcaaaatt gagtgcgtta gtgctgaaac caccgaggac    7200
tgtatcgcaa agatcatgaa cggcgaagca atgctatgt ctctggatgg cggttttgtg     7260
tatatcgcag gtaaatgcgg cctggtccca gttctggctg aaaattataa caaaagtgat    7320
aactgtgagg atactccagg ggcgggctat tttgcggtcg ctgtcgtcaa gaaatctgcg    7380
agcgatctga catgggataa cctgaaaggg aagaaatctt gccataccgc ggttggccgc    7440
accgctgggt ggaacatccc gatgggcctg ctgtataaca aaatcaatca ttgccgtttt    7500
```

```
gacgagttct tcagtgaggg gtgtgcgcct ggtagtaaga aagatagcag cctgtgcaaa    7560
ctgtgcatgg gcagcggcct gaatctgtgc gaacctaaca ataaagaggg ttactacggc    7620
tacaccggcg cgtttcgctg cctggttgag aaaggtgatg ttgcgtttgt aaagcaccaa    7680
acagtaccgc agaatacggg tgggaagaat ccggacccgt gggccaagaa tctgaatgaa    7740
aaggattacg aactgctgtg cctggatggg acccgcaagc cggttgaaga atacgcgaat    7800
tgtcacctgg cccgcgcccc gaatcacgcc gtggtgacgc gcaaagataa agaggcctgc    7860
gtccacaaaa tcctgcgtca gcagcagcac ctgttcggca gcaatgtgac agattgtagc    7920
ggtaatttct gtctgttccg tagcgaaacc aaggacctgc tgttccgtga cgacaccgtg    7980
tgtctggcca aactgcacga ccgtaatacc tacgagaaat acctgggcga ggagtacgtg    8040
aaagccgtgg gcaatctgcg taagtgtagc acaagcagcc tgctggaagc ctgcacattt    8100
cgtcgtccgt aaggtaccag aaataatttt gtttaacttt aagaaggaga ctcgagatga    8160
cgaaaacgcg ctcgaacatg gcgcgctacg gcaccagcct ggccatcgtg ctgggcgtgc    8220
acgtggtcgc cgtggtgctg acgctcaact ggtcggtgcc ccaggccatc gagctgccgc    8280
cggcagcgat gatggtcgag ttggcgccgt tgccggagcc cgcgccaccg ccaccgccca    8340
aggccgcgcc caagccaccg gcagaggtcg aggagccgcc gctgcccaag ctggtggagg    8400
cccccaagcc gaagatcgcc atcgccaagc cgcccaagcc caaggccaag ccgcagccgc    8460
ccaagcctga gaaaaagcct gagccgccga aggacgaacc accggccaag gacgatgtgg    8520 cggataccccc gccaagcaac gcgcagccgc agaaatcggc cgcaccggca ccgagcatcg    8580
cctccaacag caatgccctg cccagctggc agagcgacct gctgcgccac ctggccaagt    8640
acaagaagta cccggaagac gctcgccgtc gcggcctgca gggcatcaac cgcctgcgct    8700
tcgtggtcga cgccgagggc aaggtagtct cgtactcgct ggccggaggc tcgggcagcg    8760
cggcgctgga ccgggcgacc ctggaaatga tccgtcgcgc aggctccgta ccgaagccgc    8820
cagcggagct gttgaacaat ggcacgatcg aagtcgtggc gccgttcgtc tattccctgg    8880
accgacgtta attaacctag gctgctgcca ccgctgagca ataactagca taacccccttg    8940 gggcctctaa acgggtcttg aggggttttt tgctgaaagg aggaactata tccggattgg    9000
cgaatgggac gcgccctgta gcggcgcatt aagcgcggcg ggtgtggtgg ttacgcgcag    9060
cgtgaccgct acacttgcca gcgccctagc gcccgctcct ttcgctttct tcccttcctt    9120
tctcgccacg ttcgccggct tccccgtcca gctctaaat cggggggctcc ctttagggtt    9180 ccgatttagt gctttacggc acctcgaccc caaaaaactt gattagggtg atggttcacg    9240
tagtgggcca tcgccctgat agacggtttt tcgccctttg acgttggagt ccacgttctt    9300
taatagtgga ctcttgttcc aaactggaac aacactcaac cctatctcgg tctattcttt    9360
tgatttataa gggattttgc cgatttcggc ctattggtta aaaatgagc tgatttaaca    9420 aaaatttaac gcgaatttta acaaaatatt aacgtttaca atttctggcg cacgatggc    9480 atgagattat caaaaaggat cttcacctag atccttttaa attaaaaatg aagttttaaa    9540
tcaatctaaa gtatatatga gtaaacttgg tctgacagtt accaatgctt aatcagtgag    9600
gcacctatct cagcgatctg tctatttcgt tcatccatag ttgcctgact ccccgtcgtg    9660
tagataacta cgatacggga gggcttacca tctggcccca gtgctgcaat gataccgcga    9720
gacccacgct caccggctcc agatttatca gcaataaacc agccagcgg aagggccgag    9780 cgcagaagtg gtcctgcaac tttatccgcc tccatccagt ctattaattg ttgccgggaa    9840
```

-continued

```
gctagagtaa gtagttcgcc agttaatagt ttgcgcaacg ttgttgccat tgctacaggc    9900
atcgtggtgt cacgctcgtc gtttggtatg gcttcattca gctccggttc ccaacgatca    9960
aggcgagtta catgatcccc catgttgtgc aaaaaagcgg ttagctcctt cggtcctccg   10020
atcgttgtca gaagtaagtt ggccgcagtg ttatcactca tggttatggc agcactgcat   10080
aattctctta ctgtcatgcc atccgtaaga tgcttttctg tgactggtga gtactcaacc   10140
aagtcattct gagaatagtg tatgcggcga ccgagttgct cttgcccggc gtcaatacgg   10200
gataataccg cgccacatag cagaacttta aaagtgctca tcattggaaa acgttcttcg   10260
gggcgaaaac tctcaaggat cttaccgctg ttgagatcca gttcgatgta acccactcgt   10320
gcacccaact gatcttcagc atcttttact ttcaccagcg tttctgggtg agcaaaaaca   10380
ggaaggcaaa atgccgcaaa aaagggaata agggcgacac ggaaatgttg aatactcata   10440
ctcttccttt ttcaatcatg attgaagcat ttatcagggt tattgtctca tgagcggata   10500
catatttgaa tgtatttaga aaataaaca ataggtcat gaccaaaatc ccttaacgtg   10560
agttttcgtt ccactgagcg tcagaccccg tagaaaagat caaaggatct tcttgagatc   10620
cttttttttct gcgcgtaatc tgctgcttgc aaacaaaaaa accaccgcta ccagcggtgg   10680
tttgtttgcc ggatcaagag ctaccaactc tttttccgaa ggtaactggc ttcagcagag   10740
cgcagatacc aaatactgtc cttctagtgt agccgtagtt aggccaccac ttcaagaact   10800
ctgtagcacc gcctacatac ctcgctctgc taatcctgtt accagtggct gctgccagtg   10860
gcgataagtc gtgtcttacc gggttggact caagacgata gttaccggat aaggcgcagc   10920
ggtcgggctg aacggggggt tcgtgcacac agcccagctt ggagcgaacg acctacaccg   10980
aactgagata cctacagcgt gagctatgag aaagcgccac gcttcccgaa gggagaaagg   11040
cggacaggta tccggtaagc ggcagggtcg gaacaggaga gcgcacgagg gagcttccag   11100
ggggaaacgc ctggtatctt tatagtcctg tcgggtttcg ccacctctga cttgagcgtc   11160
gatttttgtg atgctcgtca gggggggcgga gcctatggaa aaacgccagc aacgcggcct   11220
ttttacggtt cctggccttt tgctggcctt ttgctcacat gttctttcct gcgttatccc   11280
ctgattctgt ggataaccgt attaccgcct ttgagtgagc tgataccgct cgccgcagcc   11340
gaacgaccga gcgcagcgag tcagtgagcg aggaagcgga agagcgcctg atgcggtatt   11400
ttctccttac gcatctgtgc ggtatttcac accgcatata tggtgcactc tcagtacaat   11460
ctgctctgat gccgcatagt taagccagta tacactccgc tatcgctacg tgactgggtc   11520
atggctgcgc cccgacaccc gccaacaccc gctgacgcgc cctgacgggc ttgtctgctc   11580
ccggcatccg cttacagaca agctgtgacc gtctccggga gctgcatgtg tcagaggttt   11640
tcaccgtcat caccgaaacg cgcgaggcag ctgcggtaaa gctcatcagc gtggtcgtga   11700
agcgattcac agatgtctgc ctgttcatcc gcgtccagct cgttgagttt ctccagaagc   11760
gttaatgtct ggcttctgat aaagcgggcc atgttaaggg cggttttttc ctgtttggtc   11820
actgatgcct ccgtgtaagg gggatttctg ttcatggggg taatgatacc gatgaaacga   11880
gagaggatgc tcacgatacg ggttactgat gatgaacatg cccggttact ggaacgttgt   11940
gagggtaaac aactggcggt atggatgcgg cgggaccaga gaaaaatcac tcagggtcaa   12000
tgccagcgct tcgttaatac agatgtaggt gttccacagg gtagccagca gcatcctgcg   12060
atgcagatcc ggaacataat ggtgcagggc gctgacttcc gcgtttccag actttacgaa   12120
acacggaaac cgaagaccat tcatgttgtt gctcaggtcg cagacgtttt gcagcagcag   12180
tcgcttcacg ttcgctcgcg tatcggtgat tcattctgct aaccagtaag gcaaccccgc   12240
```

-continued

```
cagcctagcc gggtcctcaa cgacaggagc acgatcatgc tagtcatgcc ccgcgcccac    12300
cggaaggagc tgactgggtt gaaggctctc aagggcatcg gtcgagatcc cggtgcctaa    12360
tgagtgagct aacttacatt aattgcgttg cgctcactgc ccgctttcca gtcgggaaac    12420
ctgtcgtgcc agctgcatta atgaatcggc caacgcgcgg ggagaggcgg tttgcgtatt    12480
gggcgccagg gtggttttc ttttcaccag tgagacgggc aacagctgat tgcccttcac    12540
cgcctggccc tgagagagtt gcagcaagcg gtccacgctg gtttgcccca gcaggcgaaa    12600
atcctgtttg atggtggtta acggcgggat ataacatgag ctgtcttcgg tatcgtcgta    12660
tcccactacc gagatgtccg caccaacgcg cagcccggac tcggtaatgg cgcgcattgc    12720
gcccagcgcc atctgatcgt tggcaaccag catcgcagtg ggaacgatgc cctcattcag    12780
catttgcatg gtttgttgaa aaccggacat ggcactccag tcgccttccc gttccgctat    12840
cggctgaatt tgattgcgag tgagatattt atgccagcca gccagacgca gacgcgccga    12900
gacagaactt aatgggcccg ctaacagcgc gatttgctgg tgacccaatg cgaccagatg    12960
ctccacgccc agtcgcgtac cgtcttcatg ggagaaaata atactgttga tgggtgtctg    13020
gtcagagaca tcaagaaata acgccggaac attagtgcag gcagcttcca cagcaatggc    13080
atcctggtca tccagcggat agttaatgat cagcccactg acgcgttgcg cgagaagatt    13140
gtgcaccgcc gctttacagg cttcgacgcc gcttcgttct accatcgaca ccaccacgct    13200
ggcacccagt tgatcggcgc gagatttaat cgccgcgaca atttgcgacg gcgcgtgcag    13260
ggccagactg gaggtggcaa cgccaatcag caacgactgt ttgcccgcca gttgttgtgc    13320
cacgcggttg ggaatgtaat tcagctccgc catcgccgct tccactttt cccgcgtttt    13380 cgcagaaacg tggctggcct ggttcaccac gcgggaaacg gtctgataag agacaccggc    13440
atactctgcg acatcgtata acgttactgg tttcacattc accaccctga attgactctc    13500
ttccgggcgc tatcatgcca taccgcgaaa ggttttgcgc cattcgatgg tgtccgggat    13560
ctcgacgctc tcccttatgc gactcctgca ttaggaagca gcccagtagt aggttgaggc    13620
cgttgagcac cgccgccgca aggaatggtg catgcaagga gatggcgccc aacagtcccc    13680
cggccacggg gcctgccacc atacccacgc cgaaacaagc gctcatgagc ccgaagtggc    13740
gagcccgatc ttccccatcg gtgatgtcgg cgataaggc gccagcaacc gcacctgtgg    13800
cgccggtgat gccggccacg atgcgtccgg cgtagaggat cgagatcgat ctcgatcccg    13860
cgaaattaat acgactcact ata                                           13883
```

BIOLOGICAL DEVICES AND METHODS OF USE THEREOF FOR THE DETECTION OF AMYLOID PROTEINS

CROSS REFERENCE TO RELATED APPLICATIONS

This application is a continuation-in-part of International Application No. PCT/US2018/065905 filed Dec. 17, 2018, which claims priority upon U.S. provisional application Ser. No. 62/599,849 filed on Dec. 18, 2017 and 62/645,691 filed Mar. 20, 2018. These applications are hereby incorporated by reference in their entirety.

CROSS REFERENCE TO SEQUENCE LISTING

The genetic components described herein are referred to by a sequence identifier number (SEQ ID NO). The SEQ ID NO corresponds numerically to the sequence identifiers <400>1, <400>2, etc. The Sequence Listing, in written computer readable format (CRF), is hereby incorporated by reference in its entirety.

BACKGROUND

The term "dementia" describes a set of symptoms that can include loss of memory, mood changes, and problems with communication and reasoning. Alzheimer's disease is the most common form of dementia and affects more than 26 million people worldwide. Incidence of Alzheimer's disease is expected to increase as the world's population ages; currently, there is no cure for this disease.

The causes of Alzheimer's disease are not well-understood, though abnormal structure called plaques and tangles have been identified in the brains of deceased Alzheimer's patients. Plaques are deposits of a protein fragment called β-amyloid, whereas tangles are twisted fibers of a different protein (tau) that accumulates inside cells. Some reports have indicated that Alzheimer's disease is associated with a high concentration of metals in the brain.

Due to the difficulty of accessing cerebral tissue in a living organism, progress in the study and understanding of Alzheimer's disease has been slow. While various Alzheimer's-associated proteins are commercially available, the cost of acquiring significant amounts of them for further research is prohibitive. A need thus exists for a method for producing proteins associated with Alzheimer's disease cheaply and efficiently. A further need exists for a model system for studying the interaction of β-amyloid and metals in cell culture and/or in a living organism. Additionally, a definitive diagnosis of Alzheimer's disease can only be made through autopsy, after death. Therefore, a need exists for earlier diagnosis of Alzheimer's disease, even before the appearance of clinical symptoms, so that intervention can be administered to slow the progress of the disease or to mitigate Alzheimer's symptoms.

SUMMARY

Described herein are devices and methods for simultaneously expressing amyloid precursor protein and TonB protein. These devices and methods increase the production of these two proteins while also minimizing costs, making the proteins more widely accessible for medical research purposes, including the development of diagnostic tests for numerous diseases associated with elevated production of amyloid proteins. The amyloid precursor protein and TonB produced by the devices and methods described herein, as well as the devices themselves, can be used in experiments designed to model the interactions between metals and amyloids such as β-amyloid that are characteristic of numerous diseases such as Alzheimer's. Finally, provided herein are diagnostic tests that can detect Alzheimer's disease in samples from patients; the tests are sensitive enough to identify diseases such as Alzheimer's even at pre-clinical stages, before the appearance of symptoms.

The advantages of the invention will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIG. 13 shows the ELISA assay for β-amyloid protein with or without metal ions. ELISA showing expression of b-amyloid protein from samples of b-amyloid sensor cells grown in presence of different metal ions ($Cu^{2+}$, $Fe^{2+}$, $Zn^{2+}$ and $Al^{2+}$) as compared to a control (non-transformed *E. coli* cells).

FIG. 14A shows the Western Blot test for b-amyloid protein from patient's blood plasma. This figure shows a band specific to b-amyloid in samples of patients with high b-amyloid fluorescence and clinically diagnosed with Alzheimer's symptoms as compared to a healthy patient with low b-amyloid fluorescence. 1. buffer (control). 2. patient with higher b-amyloid fluorescence and clinical Alzheimer's symptoms, and 3. patient with low b-amyloid fluorescence and no clinically diagnosed Alzheimer's. The patient samples (lane 2 and lane 3) are plasma samples at 30 µg/lane. Primary Antibody (Mouse b-amyloid monoclonal antibody (AMY-33) Cat #13-0100Z Thermofisher) 2 µg/mL, 2 hr RTP. Secondary: Goat Anti Mm—HRP-1:5K dilution. FIG. 14B shows the Western Blot test for b-amyloid protein from mixture of extract of DNA amyloid yeast with blood plasma from healthy patient (first lane), and Diagnosed Alzheimer's patient (second lane), as compared to standard, STD (third lane). This figure shows darker bands for sample of diagnosed Alzheimer's patient (lane 2), as compared to sample from healthy patient which shows lighter bands. Hence, the mixture of the extract of the DNA amyloid sensor with plasma showed higher expression of the protein in diagnosed Alzheimers patient as compared to healthy.

DETAILED DESCRIPTION

Figure 1:
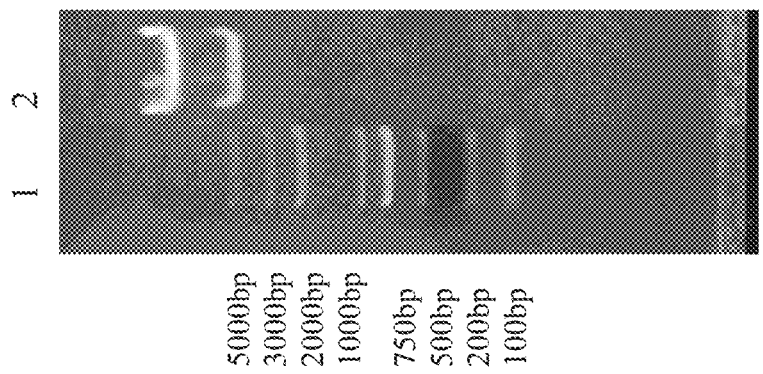
FIG. 1 shows an agarose gel analysis of a vector described herein. Lane 1 is a DNA ladder marker band with fragments ranging from 100 base pairs to 5000 base pairs and Lane 2 shows a device having SEQ ID NO. 7 after digestion with HpaI and XbaI restriction enzymes, showing two bands, one (higher) of 11 kb size and a second (lower) having 3839 base pairs.

Before the present compounds, compositions, articles, devices, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "an isolated nucleic acid" includes mixtures of two or more such nucleic acids, and the like.

"Optional" or "optionally" means that the subsequently described event or circumstance can or cannot occur, and that the description includes instances where the event or circumstance occurs and instances where it does not. For example, the phrase "optionally includes a gene for a selective marker" means that the gene may or may not be present.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc. of these materials are disclosed that while specific reference of each various individual and collective combination and permutation of these compounds may not be explicitly disclosed, each is specifically contemplated and described herein. For example, if a bacterium is disclosed and discussed and a number of different compatible bacterial plasmids are discussed, each and every combination and permutation of bacterium and bacterial plasmid that is possible is specifically contemplated unless specifically indicated to the contrary. For example, if a class of molecules A, B, and C are disclosed as well as a class of molecules D, E, and F, and an example of a combination molecule A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E is specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if a variety of additional steps can be performed, it is understood that each of these additional steps can be performed with any specific embodiment or combination of embodiments of the disclosed methods, and that each such combination is specifically contemplated and should be considered disclosed.

References in the specification and concluding claims to parts by weight, of a particular element or component in a composition or article, denote the weight relationship between the element or component and any other elements or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

I. DNA Constructs

DNA constructs are provided herein for the production of amyloid precursor protein and TonB, for the production of devices that can be used in the study of Alzheimer's disease, and for the production of devices and extracts that can be used to detect Alzheimer's disease in suspected and pre-clinical patients. It is understood that one way to define the variants and derivatives of the genetic components and DNA constructs described herein is in terms of homology/identity to specific known sequences. Those of skill in the art readily understand how to determine the homology of two nucleic acids. For example, the homology can be calculated after aligning the two sequences so that the homology is at its highest level. Another way of calculating homology can be performed according to published algorithms (see Zuker, M., *Science*, 244:48-52, 1989; Jaeger et al., *Proc. Natl. Acad. Sci. USA*, 86:7706-7710, 1989; and Jaeger et al., *Methods Enzymol.*, 183:281-306, 1989, which are herein incorporated by reference for at least material related to nucleic acid alignment).

As used herein, "conservative" mutations are mutations that result in an amino acid change in the protein produced from a sequence of DNA. When a conservative mutation occurs, the new amino acid has similar properties as the wild type amino acid and generally does not drastically change the function or folding of the protein (e.g., switching iso-leucine for valine is a conservative mutation since both are small, branched, hydrophobic amino acids). "Silent muta-tions," meanwhile, change the nucleic acid sequence of a gene encoding a protein but do not change the amino acid sequence of the protein.

It is understood that the description of mutations and homology can be combined together in any combination, such as embodiments that have at least 70%, 75%, 80%, 85%, 90%, 95%, or 99% homology to a particular sequence wherein the variants are conservative or silent mutations. It is understood that any of the sequences described herein can be a variant or derivative having the homology values listed above.

In one aspect, a database such as, for example, GenBank, can be used to determine the sequences of genes and/or regulatory regions of interest, the species from which these elements originate, and related homologous sequences.

In one aspect, genes of interest can be incorporated into a DNA construct. In a further aspect, the DNA construct can be incorporated as part of a vector for transfection into microbial cells. In a still further aspect, the vector can be a plasmid, a phagemid, a cosmid, a yeast artificial chromosome, a bacterial artificial chromosome, a virus, a phage, or a transposon. In another aspect, the microorganisms are fungi or bacteria. In one aspect, the fungi are yeasts such as, for example, *Saccharomyces cerevisiae*. In another aspect, the bacteria are *Escherichia coli*.

Vectors capable of high levels of expression of recombinant genes and proteins are well known in the art. Vectors useful for the transformation of a variety of host cells are common and commercially available and include, for example, pWLneo, pSV2cat, pOG44, pXT1, pSG, pSVK3, pBSK, pBR322, pYES, pYES2, pBSKII, pUC, and pET-Duet-1. The skilled practitioner will be able to choose a plasmid based on such factors as (a) the amount of nucleic acid (i.e., number of genes and other elements) to be inserted, (b) the host organism, (c) culture conditions for the host organism, and other related factors.

In one aspect, the DNA construct includes the following genetic components: (a) a gene that expresses a riboswitch, (b) a gene that expresses amyloid precursor protein, (c) a gene that expresses transferrin, and (d) a gene that expresses TonB. In another aspect, the DNA construct includes the following genetic components: (a) a gene that expresses β-amyloid receptor, (b) a gene that expresses amyloid precursor protein, (c) a gene that expresses a riboswitch, (d) a gene that expresses transferrin, and (e) a gene that expresses TonB. In still another aspect, the DNA construct includes the following genetic components: (a) a gene that expresses β-amyloid receptor, (b) a gene that expresses amyloid precursor protein, (c) a gene that expresses transferrin, and (d) a gene that expresses TonB.

In still another aspect, the DNA construct includes the following genetic components: (a) a gene that expresses β-amyloid receptor, and (b) a gene that expresses TonB.

In one aspect, the nucleic acids (e.g., genes that express the riboswitch, amyloid precursor protein, transferrin, TonB, and β-amyloid receptor) used in the DNA constructs described herein can be amplified using polymerase chain reaction (PCR) prior to being ligated into a plasmid or other vector. Typically, PCR amplification techniques make use of primers, or short, chemically-synthesized oligonucleotides that are complementary to regions on each respective strand flanking the DNA or nucleotide sequence to be amplified. A person having ordinary skill in the art will be able to design or choose primers based on the desired experimental conditions. In general, primers should be designed to provide for both efficient and faithful replication of the target nucleic acids. Two primers are required for the amplification of each gene, one for the sense strand (that is, the strand containing the gene of interest) and one for the antisense strand (that is, the strand complementary to the gene of interest). Pairs of primers should have similar melting temperatures that are close to the PCR reaction's annealing temperature. In order to facilitate the PCR reaction, the following features should be avoided in primers: mononucleotide repeats, complementarity with other primers in the mixture, self-complementarity, and internal hairpins and/or loops. Methods of primer design are known in the art; additionally, computer programs exist that can assist the skilled practitioner with primer design. Primers can optionally incorporate restriction enzyme recognition sites at their 5' ends to assist in later ligation into plasmids or other vectors.

PCR can be carried out using purified DNA, unpurified DNA that is integrated into a vector, or unpurified genomic DNA. The process for amplifying target DNA using PCR consists of introducing an excess of two primers having the characteristics described above to a mixture containing the sequence to be amplified, followed by a series of thermal cycles in the presence of a heat-tolerant or thermophilic DNA polymerase, such as, for example, any of Taq, Pfu, Pwo, Tfl, rTth, Tli, or Tma polymerases. A PCR "cycle" involves denaturation of the DNA through heating, followed by annealing of the primers to the target DNA, followed by extension of the primers using the thermophilic DNA polymerase and a supply of deoxynucleotide triphosphates (i.e., dCTP, dATP, dGTP, and TTP), along with buffers, salts, and other reagents as needed. In one aspect, the DNA segments created by primer extension during the PCR process can serve as templates for additional PCR cycles. Many PCR cycles can be performed to generate a large concentration of target DNA or gene. PCR can optionally be performed in a device or machine with programmable temperature cycles for denaturation, annealing, and extension steps. Further, PCR can be performed on multiple genes simultaneously in the same reaction vessel or microcentrifuge tube since the primers chosen will be specific to selected genes. PCR products can be purified by techniques known in the art such as, for example, gel electrophoresis followed by extraction from the gel using commercial kits and reagents.

In a further aspect, the plasmid can include an origin of replication, allowing it to use the host cell's replication machinery to create copies of itself.

As used herein, "operably linked" refers to the association of nucleic acid sequences on a single nucleic acid fragment so that the function of one affects the function of another. For example, if sequences for multiple genes are inserted into a single plasmid, their expression may be operably linked. Alternatively, a promoter is said to be operably linked with a coding sequence when it is capable of affecting the expression of that coding sequence.

As used herein, "expression" refers to transcription and/or accumulation of an mRNA derived from a gene or DNA fragment. Expression may also be used to refer to translation of mRNA into a peptide, polypeptide, or protein.

In one aspect, the gene that expresses amyloid precursor protein is isolated from a mammal. In a further aspect, the mammal is a primate such as, for example, a human, a chimpanzee, a gorilla, a Sumatran orangutan, an olive baboon, a golden snub-nosed monkey, a sooty mangabey, a black snub-nosed monkey, a crab-eating macaque, a rhesus macaque, a southern pig-tailed macaque, an Angola colobus, a white-headed capuchin, a green monkey, a drill, a common marmoset, a black-capped squirrel monkey, a northern white-cheeked gibbon, a gray mouse lemur, Nancy Ma's night monkey, or a Philippine tarsier. In an alternative aspect, the gene that expresses amyloid precursor protein is isolated from a non-primate mammal such as, for example, a horse, a Przewalski's horse, a donkey, a sunda pangolin, a northern tree shrew, a large flying fox, an aardvark, a baiji, a killer whale, an alpaca, a pig, a Chinese rufous horseshoe bat, a cape golden mole, a Hawaiian monk seal, a naked mole rat, a cape elephant shrew, a sea otter, a giant panda, an Egyptian fruit bat, a cow, a white-tailed deer, a minke whale, a guinea pig, a European rabbit, a Chinese tree shrew, a sheep, a wild Bactrian camel, a Bactrian camel, a leopard, a goat, a bison, a big brown bat, a walrus, a chinchilla, a domestic dog, a nine-banded armadillo, a European hedgehog, a polar bear, a Tibetan antelope, a water buffalo, a domestic cat, an American pika, or a lesser Egyptian jerboa. In a further aspect, the gene that expresses amyloid precursor protein has SEQ ID NO. 3 or at least 70% homology thereto, at least 75% homology thereto, at least 80% homology thereto, at least 85% homology thereto, at least 90% homology thereto, or at least 95% homology thereto. In one aspect, the gene that expresses amyloid precursor protein is isolated from *Homo sapiens* and can be found in GenBank with GI number NM_201414.2.

Other sequences expressing amyloid precursor protein or related or homologous genes can be identified in a database such as, for example, GenBank. In one aspect, sequences useful herein include those with the GI numbers listed in Table 1.

TABLE 1

Amyloid Precursor Protein Genes

| Source Organism | Sequence Description | GI Number |
| --- | --- | --- |
| Homo sapiens | amyloid precursor protein | NM_201414.2 |
| Artificial sequence | amyloid precursor protein | EU716635.1 |
| Homo sapiens | amyloid precursor protein | Y00264.1 |
| Pan troglodytes | amyloid precursor protein | XM_009452766.2 |
| Gorilla gorilla | amyloid precursor protein | XM_004062635.2 |
| Homo sapiens | amyloid precursor protein | NM_001136131.2 |
| Homo sapiens | amyloid precursor protein | AK296229.1 |
| Pongo abelii | amyloid precursor protein | NM_001133542.1 |
| Papio anubis | amyloid precursor protein | XM_017956498.1 |
| Rhinopithecus roxellana | amyloid precursor protein | XM_010383440.1 |
| Cercocebus atys | amyloid precursor protein | XM_012029848.1 |
| Rhinopithecus bieti | amyloid precursor protein | XM_017856490.1 |
| Macaca fascicularis | amyloid precursor protein | XM_005548887.2 |
| Macaca mulatta | amyloid precursor protein | XM_015133072.1 |
| Macaca fascicularis | amyloid precursor protein | M58727.1 |
| Macaca nemestrina | amyloid precursor protein | XM_011726340.1 |

TABLE 1-continued

Amyloid Precursor Protein Genes

| Source Organism | Sequence Description | GI Number |
|---|---|---|
| Colobus angolensis | amyloid precursor protein | XM_011926494.1 |
| Homo sapiens | amyloid precursor protein | AK298861.1 |
| Chlorocebus sabaeus | amyloid precursor protein | XM_007966074.1 |
| Mandrillus leucophaeus | amyloid precursor protein | XM_011998311.1 |
| Colobus angolensis | amyloid precursor protein | XM_011926496.1 |
| Cebus capucinus | amyloid precursor protein | XM_017541908.1 |
| Callithrix jacchus | amyloid precursor protein | XM_008986526.2 |
| Homo sapiens | amyloid precursor protein | NM_001136129.2 |
| Homo sapiens | amyloid precursor protein | AF282245.1 |
| Saimiri boliviensis | amyloid precursor protein | XM_010344901.1 |
| Nomascus leucogenys | amyloid precursor protein | XM_003263808.3 |
| Colobus angolensis | amyloid precursor protein | XM_011926497.1 |
| Pan troglodytes | amyloid precursor protein | AK304995.1 |
| Microcebus murinus | amyloid precursor protein | XM_012764455.1 |
| Carlito syrichta | amyloid precursor protein | XM_008049942.2 |
| Homo sapiens | amyloid precursor protein | NM_001204303.1 |
| Equus przewalskii | amyloid precursor protein | XM_008514150.1 |
| Equus caballus | amyloid precursor protein | XM_003364171.3 |
| Pan troglodytes | amyloid precursor protein | XM_009453143.2 |
| Equus asinus | amyloid precursor protein | XM_014859018.1 |
| Gorilla gorilla | amyloid precursor protein | XM_004062638.2 |
| Manis javanica | amyloid precursor protein | XM_017650814.1 |
| Rhinopithecus roxellana | amyloid precursor protein | XM_010383441.1 |
| Papio anubis | amyloid precursor protein | XM_017956499.1 |
| Tupaia belangeri | amyloid precursor protein | KF479228.2 |
| Tupaia belangeri | amyloid precursor protein | KY399770.1 |
| Rhinopithecus bieti | amyloid precursor protein | XM_017856498.1 |
| Cercocebus atys | amyloid precursor protein | XM_012029849.1 |
| Macaca fascicularis | amyloid precursor protein | XM_005548888.2 |
| Macaca mulatta | amyloid precursor protein | XM_015133073.1 |
| Macaca nemestrina | amyloid precursor protein | XM_011726341.1 |
| Pteropus vampyrus | amyloid precursor protein | XM_011358211.1 |
| Pteropus alecto | amyloid precursor protein | XM_015586510.1 |
| Orycteropus afer | amyloid precursor protein | XM_007943498.1 |
| Lipotes vexillifer | amyloid precursor protein | XM_007466496.1 |
| Orcinus orca | amyloid precursor protein | XM_004264482.1 |
| Vicugna pacos | amyloid precursor protein | XM_006215213.2 |
| Colobus angolensis | amyloid precursor protein | XM_011926495.1 |
| Sus scrofa | amyloid precursor protein | AK392671.1 |
| Rhinolophus sinicus | amyloid precursor protein | XM_019729868.1 |
| Sus scrofa | amyloid precursor protein | XM_005670305.3 |
| Sus scrofa | amyloid precursor protein | DQ267684.1 |
| Chlorocebus sabaeus | amyloid precursor protein | XM_007966083.1 |
| Chrysochloris asiatica | amyloid precursor protein | XM_006872473.1 |
| Neomonachus schauinslandi | amyloid precursor protein | XM_021678096.1 |
| Heterocephalus glaber | amyloid precursor protein | XM_004842236.3 |
| Aotus nancymaae | amyloid precursor protein | XM_021670543.1 |
| Elephantulus edwardii | amyloid precursor protein | XM_006896033.1 |
| Enhydra lutris | amyloid precursor protein | XM_022510986.1 |
| Ailuropod melanoleuca | amyloid precursor protein | XM_002920065.3 |
| Rousettus aegyptiacus | amyloid precursor protein | XM_016121316.1 |
| Bos taurus | amyloid precursor protein | NM_001076796.1 |
| Balaenoptera acutorostrata | amyloid precursor protein | XM_007164150.1 |
| Odocoileus virginianus | amyloid precursor protein | XM_020892411.1 |
| Lipotes vexillifer | amyloid precursor protein | XM_007466499.1 |
| Cavia porcellus | amyloid precursor protein | XM_005002497.2 |
| Oryctolagus cuniculus | amyloid precursor protein | XM_008266829.2 |
| Tupaia chinensis | amyloid precursor protein | XM_006157706.1 |
| Cavia porcellus | amyloid precursor protein | X97631.1 |
| Ovis aries | amyloid precursor protein | XM_004002799.3 |
| Camelus ferus | amyloid precursor protein | XM_006186178.2 |
| Homo sapiens | amyloid precursor protein | AK297412.1 |
| Camelus bactrianus | amyloid precursor protein | XM_010956631.1 |
| Panthera pardus | amyloid precursor protein | XM_019467791.1 |
| Capra hircus | amyloid precursor protein | XM_018050752.1 |
| Ovis aries | amyloid precursor protein | XM_012169352.2 |
| Bison bison | amyloid precursor protein | XM_010838453.1 |
| Eptesicus fuscus | amyloid precursor protein | XM_008145624.1 |
| Callithrix jacchus | amyloid precursor protein | XM_008986527.2 |
| Cebus capucinus | amyloid precursor protein | XM_017541910.1 |
| Chinchilla lanigera | amyloid precursor protein | XM_005375597.2 |
| Odobenus rosmarus | amyloid precursor protein | XM_004413350.2 |
| Canis lupus familiaris | amyloid precursor protein | NM_001293279.1 |
| Canis familiaris | amyloid precursor protein | AY498707.1 |
| Canis lupus familiaris | amyloid precursor protein | AY926582.1 |
| Dasypus novemcinctus | amyloid precursor protein | XM_004468674.2 |

TABLE 1-continued

Amyloid Precursor Protein Genes

| Source Organism | Sequence Description | GI Number |
|---|---|---|
| *Erinaceus europaeus* | amyloid precursor protein | XM_016186732.1 |
| *Ursus maritimus* | amyloid precursor protein | XM_008701769.1 |
| *Pantholops hodgsonii* | amyloid precursor protein | XM_005973985.1 |
| *Bubalus bubalis* | amyloid precursor protein | XM_006042073.1 |
| *Felis catus* | amyloid precursor protein | XM_006935946.2 |
| *Ochotona princeps* | amyloid precursor protein | XM_004588599.2 |
| *Jaculus jaculus* | amyloid precursor protein | XM_004654385.1 |
| *Lipotes vexilifer* | amyloid precursor protein | XM_007466497.1 |

In one aspect, the gene that expresses transferrin is isolated from a mammal. In a further aspect, the mammal is a primate such as, for example, a gorilla, a human, a bonobo, a chimpanzee, a northern white-cheeked gibbon, a Bornean orangutan, a Sumatran orangutan, a siamang, a lar gibbon, Allen's swamp monkey, Francois' langur, a gray-cheeked mangabey, an Angola colobus, a green monkey, a crab-eating macaque, a southern pig-tailed macaque, a mantled guereza, a sooty mangabey, a drill, a rhesus macaque, a common squirrel monkey, a black-capped squirrel monkey, Nancy Ma's night monkey, an olive baboon, a red-tailed monkey, a black snub-nosed monkey, a brown wooly monkey, a white-headed marmoset, a common marmoset, a red-bellied titi, a Bolivian red howler monkey, a white-headed capuchin, a brown-mantled tamarin, a golden snub-nosed monkey, a Philippine tarsier, a Coquerel's sifaka, a gray mouse lemur, or a sunda flying lemur. In an alternative aspect, the gene that expresses transferrin is isolated from a non-primate mammal such as, for example, a thirteen-lined ground squirrel, an American pika, a European rabbit, a groundhog, an Alpine marmot, a lesser Egyptian jerboa, a chinchilla, a northern Israeli blind subterranean mole rat, a common degu, a Chinese tree shrew, a naked mole rat, a guinea pig, a Damara mole rat, a North American deer mouse, a North American beaver, a mouse, a Mongolian gerbil, a wild Bactrian camel, a dromedary camel, or a Bactrian camel. In a further aspect, the gene that expresses transferrin has SEQ ID NO. 5 or at least 70% homology thereto, at least 75% homology thereto, at least 80% homology thereto, at least 85% homology thereto, at least 90% homology thereto, or at least 95% homology thereto. In another aspect, the gene expressing a transferrin is a serotransferrin, an epididymis secretory sperm binding protein, or a homolog thereof. In one aspect, the gene that expresses transferrin is isolated from a gorilla and can be found in GenBank with GI number XM_019022854.1.

Other sequences expressing transferrin or related or homologous genes can be identified in a database such as, for example, GenBank. In one aspect, sequences useful herein include those with the GI numbers listed in Table 2:

TABLE 2

Transferrin Genes

| Source Organism | Sequence Description | GI Number |
|---|---|---|
| *Gorilla gorilla* | transferrin | XM_019022854.1 |
| *Gorilla gorilla* | transferrin | NM_001303546.1 |
| *Homo sapiens* | transferrin | NM_001063.3 |
| *Homo sapiens* | transferrin | DQ923758.1 |
| *Homo sapiens* | transferrin | S95936.1 |
| *Homo sapiens* | transferrin | AB590492.1 |
| *Homo sapiens* | transferrin | XM_017007090.1 |
| *Homo sapiens* | transferrin | XM_017007089.1 |
| *Homo sapiens* | transferrin | AK222755.1 |
| *Homo sapiens* | transferrin | M12530.1 |
| *Homo sapiens* | epididymis secretory sperm binding protein | GQ472199.1 |
| *Pan paniscus* | serotransferrin | XM_008976094.1 |
| *Homo sapiens* | transferrin | BC059367.1 |
| *Homo sapiens* | transferrin | KJ897654.1 |
| *Homo sapiens* | transferrin | CR936810.1 |
| *Pan troglodytes* | transferrin | NM_001144835.1 |
| *Homo sapiens* | transferrin | NM_001354703.1 |
| *Nomascus leucogenys* | transferrin | XM_003265239.3 |
| *Pongo pygmaeus* | transferrin | KM972646.1 |
| *Nomascus leucogenys* | transferrin | NM_001308674.1 |
| *Homo sapiens* | transferrin | NM_001354704.1 |
| *Pongo abelii* | transferrin | NM_001133958.1 |
| *Homo sapiens* | serotransferrin | AK295419.1 |
| *Symphalangus syndactylus* | transferrin | KM972647.1 |
| *Hylobates lar* | transferrin | KM972649.1 |
| *Allenopithecus nigroviridis* | transferrin | KM972653.1 |
| *Homo sapiens* | transferrin | BX648533.1 |
| *Homo sapiens* | transferrin | AF118063.1 |
| *Trachypithecus francoisi* | transferrin | KM972656.1 |
| *Lophocebus albigena* | transferrin | KM972652.1 |
| *Colobus angolensis* | serotransferrin | XM_011958201.1 |
| *Chlorocebus sabaeus* | transferrin | XM_008009084.1 |

TABLE 2-continued

Transferrin Genes

| Source Organism | Sequence Description | GI Number |
|---|---|---|
| Macaca nemestrina | transferrin | XM_011721456.1 |
| Macaca fascicularis | transferrin | AB169522.1 |
| Colobus guereza | transferrin | KM972655.1 |
| Macaca fascicularis | serotransferrin | XM_005545793.2 |
| Cercocebus atys | transferrin | XM_012061466.1 |
| Mandrillus leucophaeus | transferrin | XM_011970225.1 |
| Macaca mulatta | serotransferrin | NM_001318182.1 |
| Mandrillus leucophaeus | transferrin | XM_011970224.1 |
| Macaca fascicularis | transferrin | AB170458.1 |
| Pongo abelii | transferrin | XM_009239319.1 |
| Saimiri sciureus | transferrin | KM972659.1 |
| Saimiri boliviensis | transferrin | XM_003925066.2 |
| Aotus nancymaae | transferrin | NM_001308518.1 |
| Papio anubis | transferrin | KM972651.1 |
| Cercopithecus ascanius | transferrin | KM972654.1 |
| Chlorocebus sabaeus | transferrin | XM_008009085.1 |
| Rhinopithecus bieti | serotransferrin | XM_017872421.1 |
| Rhinopithecus bieti | serotransferrin | XM_017872420.1 |
| Papio anubis | serotransferrin | XM_021934857.1 |
| Lagothrix lagotricha | transferrin | KM972663.1 |
| Callithrix jacchus | transferrin | XM_008983803.2 |
| Callithrix geoffroyi | transferrin | KM972658.1 |
| Callicebus moloch | transferrin | KM972661.1 |
| Alouatta sara | transferrin | KM972662.1 |
| Homo sapiens | serotransferrin | AK295334.1 |
| Cebus capucinus | transferrin | XM_017505719.1 |
| Homo sapiens | serotransferrin | AK303753.1 |
| Saguinus fuscicollis | transferrin | KM972657.1 |
| Cebus capucinus | transferrin | XR_001818300.1 |
| Colobus angolensis | serotransferrin | XM_011958202.1 |
| Carlito syrichta | serotransferrin | XM_021712084.1 |
| Propithecus coquereli | serotransferrin | XM_012664058.1 |
| Microcebus murinus | serotransferrin | XM_012766832.2 |
| Galeopterus variegatus | serotransferrin | XM_008581124.1 |
| Ictidomys tridecemlineatus | serotransferrin | XM_005327026.2 |
| Ochotona princeps | transferrin | XM_004588321.2 |
| Oryctolagus cuniculus | transferrin | NM_001101694.1 |
| Marmota monax | transferrin | AY288100.1 |
| Ochotona princeps | transferrin | XM_004588320.2 |
| Marmota marmota | serotransferrin | XM_015487041.1 |
| Jaculus jaculus | serotransferrin | XM_004664199.1 |
| Chinchilla lanigera | serotransferrin | XM_005406809.2 |
| Nannospalax galili | serotransferrin | XM_017802840.1 |
| Octodon degus | serotransferrin | XM_004625212.1 |
| Tupaia chinensis | transferrin | XM_014584459.1 |
| Heterocephalus glaber | serotransferrin | XM_004834254.3 |
| Cavia porcellus | serotransferrin | XM_003476728.3 |
| Fukomys damarensis | serotransferrin | XM_010625485.2 |
| Fukomys damarensis | serotransferrin | XM_010625484.2 |
| Peromyscus maniculatus | serotransferrin | XM_006978668.2 |
| Rhinopithecus roxellana | transferrin | XM_010379532.1 |
| Artificial sequence | synthetic construct | JX091745.1 |
| Castor canadensis | serotransferrin | XM_020165722.1 |
| Mus musculus | transferrin | NM_133977.2 |
| Mus musculus | transferrin | AK142599.1 |
| Mus musculus | transferrin | AK168419.1 |
| Mus musculus | transferrin | AK149559.1 |
| Mus musculus | transferrin | AK085754.1 |
| Meriones unguiculatus | serotransferrin | XM_021663252.1 |
| Camelus ferus | transferrin | XM_006179717.2 |
| Camelus dromedaries | transferrin | XM_010975530.1 |
| Camelus bactrianus | transferrin | XM_010947720.1 |
| Mus musculus | transferrin | AK149595.1 |
| Mus musculus | transferrin | BC022986.1 |
| Mus musculus | transferrin | BC092046.1 |
| Mus musculus | transferrin | BC058218.1 |
| Mus musculus | transferrin | BC058216.1 |
| Mus musculus | transferrin | BC020295.1 |

In one aspect, the gene that expresses TonB is isolated from a bacterium. In a further aspect, the bacterium is a *Pseudomonas* species such as, for example, *P. entomophila*, *P.* sp. CCOS191, *P. putida*, *P. mosselii*, *P.* sp. DRA525, *P.* sp. FGI182, *P.* sp. JY-Q, *P. plecoglossicida*, *P.* sp. VLB120, *P. fulva*, *P.* sp. URMO17WK12:I11, *P. parafulva*, *P. syringae*, *P. frederiksbergensis*, *P. fluorescens*, *P. asplenii*, or *P. fuscovaginae*. In an alternative aspect, the bacterium is *Enterococcus faecalis*. In a further aspect, the gene that expresses TonB has SEQ ID NO. 6 or at least 70% homology thereto, at least 75% homology thereto, at least 80% homology thereto, at least 85% homology thereto, at least 90% homology thereto, or at least 95% homology thereto. In one aspect, the gene that expresses TonB is isolated from *P. entomophila* and can be found in GenBank with GI number CT573326.1

Other sequences expressing TonB or related or homologous genes can be identified in a database such as, for example, GenBank. In one aspect, sequences useful herein include those with the GI numbers listed in Table 3:

In one aspect, the gene that expresses β-amyloid receptor is isolated from a mammal. In a further aspect, the mammal is a primate such as, for example, a human, a northern white-cheeked gibbon, an olive baboon, a gorilla, a sooty mangabey, a drill, a chimpanzee, an Angola colobus, a Sumatran orangutan, a crab-eating macaque, a rhesus macaque, or a golden snub-nosed monkey. In a further aspect, the gene that expresses β-amyloid receptor has SEQ ID NO. 8 or at least 70% homology thereto, at least 75%

TABLE 3

TonB Genes

| Source Organism | Sequence Description | GI Number |
| --- | --- | --- |
| *Pseudomonas entomophila* | genomic DNA | CT573326.1 |
| *Pseudomonas* sp. CCOS 191 | genomic DNA | LN847264.1 |
| *Pseudomonas mosselii* | genomic DNA | CP024159.1 |
| *Pseudomonas mosselii* | genomic DNA | CP023299.1 |
| *Pseudomonas putida* | genomic DNA | CP014343.1 |
| *Pseudomonas mosselii* | genomic DNA | CP009365.1 |
| *Pseudomonas putida* | genomic DNA | CP018846.1 |
| *Pseudomonas* sp. DRA525 | genomic DNA | CP018743.1 |
| *Pseudomonas putida* | genomic DNA | CP010979.1 |
| *Pseudomonas putida* | genomic DNA | CP003738.1 |
| *Pseudomonas* sp. FGI182 | genomic DNA | CP007012.1 |
| *Pseudomonas putida* | genomic DNA | CP002870.1 |
| *Pseudomonas putida* | genomic DNA | CP000926.1 |
| *Pseudomonas putida* | genomic DNA | CP017073.1 |
| *Pseudomonas putida* | genomic DNA | AP013070.1 |
| *Pseudomonas* sp. JY-Q | genomic DNA | CP011525.1 |
| *Pseudomonas plecoglossicida* | genomic DNA | CP010359.1 |
| *Pseudomonas putida* | genomic DNA | CP007620.1 |
| *Pseudomonas montellii* | genomic DNA | CP006979.1 |
| *Pseudomonas montellii* | genomic DNA | CP006978.1 |
| *Pseudomonas putida* | genomic DNA | CP003734.1 |
| *Pseudomonas putida* | TonB | AF315582.1 |
| *Pseudomonas putida* | genomic DNA | LT799039.1 |
| *Pseudomonas putida* | genomic DNA | CP015202.1 |
| *Pseudomonas putida* | genomic DNA | AE015451.2 |
| *Pseudomonas putida* | genomic DNA | LT707061.1 |
| *Pseudomonas putida* | genomic DNA | CP016212.1 |
| *Pseudomonas putida* | genomic DNA | CP009974.1 |
| *Pseudomonas putida* | genomic DNA | CP002290.1 |
| *Pseudomonas putida* | genomic DNA | CP015876.1 |
| *Pseudomonas putida* | genomic DNA | CP003588.1 |
| *Pseudomonas putida* | genomic DNA | CP000712.1 |
| *Pseudomonas putida* | genomic DNA | AP015029.1 |
| *Pseudomonas putida* | genomic DNA | CP005976.1 |
| *Pseudomonas putida* | genomic DNA | CP024086.1 |
| *Pseudomonas putida* | genomic DNA | CP011789.1 |
| *Pseudomonas putida* | genomic DNA | CP024085.1 |
| *Pseudomonas putida* | TonB | X70139.1 |
| *Pseudomonas* sp. VLB120 | genomic DNA | CP003961.1 |
| *Pseudomonas puitda* | genomic DNA | CP000949.1 |
| *Pseudomonas fulva* | genomic DNA | CP023048.1 |
| *Pseudomonas* sp. URMO17WK12:I11 | genomic DNA | LN865164.1 |
| *Enterococcus faecalis* | genomic DNA | CP022312.1 |
| *Pseudomonas parafulva* | genomic DNA | CP019952.1 |
| *Pseudomonas montellii* | genomic DNA | CP013997.1 |
| *Pseudomonas syringae* | genomic DNA | CP024712.1 |
| *Pseudomonas syringae* | genomic DNA | CP019732.1 |
| *Pseudomonas syringae* | genomic DNA | CP019730.1 |
| *Pseudomonas syringae* | genomic DNA | CP017009.1 |
| *Pseudomonas syringae* | genomic DNA | CP017007.1 |
| *Pseudomonas syringae* | genomic DNA | CP011972.2 |
| *Pseudomonas syringae* | genomic DNA | CP012179.1 |
| *Pseudomonas frederiksbergensis* | genomic DNA | CP018319.1 |
| *Pseudomonas fluorescens* | genomic DNA | CP000094.2 |
| *Pseudomonas syringae* | genomic DNA | CP018202.1 |
| *Pseudomonas asplenii* | genomic DNA | LT629777.1 |
| *Pseudomonas fuscovaginae* | genomic DNA | LT629972.1 |
| *Pseudomonas fulva* | genomic DNA | CP002727.1 | homology thereto, at least 80% homology thereto, at least 85% homology thereto, at least 90% homology thereto, or at least 95% homology thereto. In another aspect, the β-amyloid receptor is an immunoglobulin-like receptor including any member from family A or B, or is a homolog thereof. In one aspect, the gene that expresses β-amyloid receptor is isolated from humans and can be found in GenBank with GI number NM_005874.4.

Other sequences expressing β-amyloid receptor or related or homologous genes can be identified in a database such as, for example, GenBank. In one aspect, sequences useful herein include those with the GI numbers listed in Table 4:

TABLE 4

β-Amyloid Receptor Genes

| Source Organism | Sequence Description | GI Number |
|---|---|---|
| Homo sapiens | immunoglobulin-like receptor B2 | NM_005874.4 |
| Homo sapiens | immunoglobulin-like transcript 4 | AF000574.1 |
| Homo sapiens | immunoglobulin-like receptor B2 | NM_001080978.3 |
| Homo sapiens | immunoglobulin-like receptor B2 | NM_001278403.2 |
| Homo sapiens | immunoglobulin-like receptor 2 | AF283987.1 |
| Homo sapiens | splice isoform of A8N423 variant | AK226015.1 |
| Homo sapiens | immunoglobulin-like transcript 4 | AF011565.1 |
| Homo sapiens | immunoglobulin-like receptor 2 | AF025528.1 |
| Homo sapiens | immunoglobulin-like receptor B | BC036827.1 |
| Homo sapiens | immunoglobulin-like receptor B | GQ129422.1 |
| Homo sapiens | immunoglobulin-like receptor B | EU832815.1 |
| Homo sapiens | immunoglobulin-like receptor B2 | AK297071.1 |
| Homo sapiens | immunoglobulin-like receptor 2 | AF283986.1 |
| Homo sapiens | immunoglobulin-like receptor B2 | NM_001278404.2 |
| Homo sapiens | immunoglobulin-like receptor B2 | AK297041.1 |
| Homo sapiens | immunoglobulin-like receptor B2 | NR_103521.2 |
| Homo sapiens | cDNA | AK310263.1 |
| Homo sapiens | immunoglobulin-like receptor B2 | NM_001278405.2 |
| Homo sapiens | immunoglobulin-like transcript 4 | AF011566.1 |
| Homo sapiens | immunoglobulin-like receptor B2 | NM_001278406.2 |
| Homo sapiens | immunoglobulin-like receptor B2 | BC025766.1 |
| Homo sapiens | immunoglobulin-like receptor B2 | LC125264.1 |
| Homo sapiens | immunoglobulin-like receptor B2 | EU915606.1 |
| Homo sapiens | immunoglobulin-like receptor B1 | XM_017026191.1 |
| Homo sapiens | immunoglobulin-like receptor B1 | XM_011526336.2 |
| Nomascus leucogenys | immunoglobulin-like receptor A3 | XM_012499998.1 |
| Papio anubis | immunoglobulin-like receptor B2 | XM_021931420.1 |
| Papio anubis | immunoglobulin-like receptor B2 | XM_021931421.1 |
| Gorilla gorilla | immunoglobulin-like receptor B1 | XM_019014815.1 |
| Cercocebus atys | immunoglobulin-like receptor B2 | XM_012081733.1 |
| Gorilla gorilla | immunoglobulin-like receptor B1 | XM_019014817.1 |
| Gorilla gorilla | immunoglobulin-like receptor B1 | XM_019014814.1 |
| Gorilla gorilla | immunoglobulin-like receptor B1 | XM_019014816.1 |
| Gorilla gorilla | immunoglobulin-like receptor B1 | XM_019014813.1 |
| Mandrillus leucophaeus | immunoglobulin-like receptor B1 | XM_011977366.1 |
| Pan troglodytes | immunoglobulin-like receptor B1 | XM_009436281.2 |
| Pan troglodytes | immunoglobulin-like receptor B1 | XM_009436279.2 |
| Pan troglodytes | immunoglobulin-like receptor B1 | XM_009436282.2 |
| Pan troglodytes | immunoglobulin-like receptor B1 | XM_009436280.2 |
| Mandrillus leucophaeus | immunoglobulin-like receptor B1 | XM_011977365.1 |
| Mandrillus leucophaeus | immunoglobulin-like receptor B1 | XR_001005766.1 |
| Colobus angolensis | immunoglobulin-like receptor B2 | XR_001000667.1 |
| Colobus angolensis | immunoglobulin-like receptor B2 | XR_001000670.1 |
| Colobus angolensis | immunoglobulin-like receptor B2 | XR_001000669.1 |
| Colobus angolensis | immunoglobulin-like receptor B2 | XR_001000668.1 |
| Homo sapiens | immunoglobulin-like receptor B1 | XM_017026188.1 |
| Homo sapiens | immunoglobulin-like receptor B1 | XM_017026187.1 |
| Homo sapiens | immunoglobulin-like receptor B1 | XM_017026186.1 |
| Homo sapiens | immunoglobulin-like receptor B1 | NM_001081638.3 |
| Homo sapiens | immunoglobulin-like receptor B1 | NM_001081637.2 |
| Homo sapiens | immunoglobulin-like receptor B1 | LT742769.1 |
| Homo sapiens | immunoglobulin-like receptor B1 | XM_017026190.1 |
| Homo sapiens | immunoglobulin-like receptor B1 | XM_017026189.1 |
| Homo sapiens | immunoglobulin-like receptor B1 | XM_017026185.1 |
| Homo sapiens | immunoglobulin-like receptor B1 | KJ898301.1 |
| Homo sapiens | immunoglobulin-like receptor B1 | NM_001081639.3 |
| Homo sapiens | immunoglobulin-like receptor B1 | NM_006669.6 |
| Homo sapiens | immunoglobulin-like receptor B | AB590401.1 |
| Homo sapiens | immunoglobulin-like receptor B | DQ895431.2 |
| Homo sapiens | immunoglobulin-like receptor B | DQ892230.2 |
| Homo sapiens | immunoglobulin-like receptor B1 | BC015731.1 |
| Homo sapiens | immunoglobulin-like receptor 1 | AF009220.1 |
| Homo sapiens | immunoglobulin-like transcript 2 | U82279.1 |
| Homo sapiens | immunoglobulin-like receptor B1 | AK223310.1 |
| Homo sapiens | immunoglobulin-like receptor B | AK292028.1 |
| Homo sapiens | immunoglobulin-like receptor 1 | AF283985.1 |
| Homo sapiens | immunoglobulin-like receptor 1 | AF283984.1 |
| Homo sapiens | immunoglobulin-like receptor 1 | AF009221.1 |

TABLE 4-continued

β-Amyloid Receptor Genes

| Source Organism | Sequence Description | GI Number |
| --- | --- | --- |
| Pongo abelii | immunoglobulin-like receptor A3 | XM_009233107.1 |
| Pongo abelii | immunoglobulin-like receptor A3 | XM_009233106.1 |
| Homo sapiens | immunoglobulin-like receptor B | AK292156.1 |
| Homo sapiens | Ig-related receptor MIR-7 | AF004230.1 |
| Macaca fascicularis | immunoglobulin-like receptor B2 | XM_015441717.1 |
| Nomascus leucogenys | immunoglobulin-like receptor B4 | XM_012500018.1 |
| Nomascus leucogenys | immunoglobulin-like receptor B4 | XM_012500021.1 |
| Nomascus leucogenys | immunoglobulin-like receptor B4 | XM_012500020.1 |
| Pongo abelii | immunoglobulin-like receptor A3 | XM_009233109.1 |
| Pongo abelii | immunoglobulin-like receptor A3 | XM_009233108.1 |
| Homo sapiens | immunoglobulin-like transcript 2a | AF009005.1 |
| Nomascus leucogenys | immunoglobulin-like receptor B4 | XM_012500017.1 |
| Nomascus leucogenys | immunoglobulin-like receptor B4 | XM_012500019.1 |
| Colobus angolensis | immunoglobulin-like receptor B2 | XM_011932553.1 |
| Papio anubis | immunoglobulin-like receptor B2 | XM_021931416.1 |
| Papio anubis | immunoglobulin-like receptor B2 | XM_021931415.1 |
| Macaca mulatta | immunoglobulin-like receptor B1 | XM_015124907.1 |
| Cercocebus atys | immunoglobulin-like receptor B2 | XM_012053973.1 |
| Homo sapiens | immunoglobulin-like transcript 1 | AF041034.1 |
| Macaca mulatta | immunoglobulin-like receptor B1 | XM_015124906.1 |
| Cercocebus atys | immunoglobulin-like receptor B2 | XM_012081730.1 |
| Macaca mulatta | immunoglobulin-like receptor B1 | XM_015124908.1 |
| Cercocebus atys | immunoglobulin-like receptor B1 | XM_012053495.1 |
| Macaca mulatta | immunoglobulin-like receptor B | DQ155432.1 |
| Papio anubis | immunoglobulin-like receptor B2 | XM_021931418.1 |
| Papio anubis | immunoglobulin-like receptor B2 | XM_021931417.1 |
| Macaca mulatta | immunoglobulin-like receptor B1 | XM_015124909.1 |
| Cercocebus atys | immunoglobulin-like receptor B2 | XM_012081731.1 |
| Rhinopithecus roxellana | immunoglobulin-like receptor B4 | XM_010379809.1 |
| Mandrillus leucophaeus | immunoglobulin-like receptor B1 | XM_011977359.1 |
| Rhinopithecus roxellana | immunoglobulin-like receptor B4 | XM_010379808.1 |
| Mandrillus leucophaeus | immunoglobulin-like receptor B1 | XM_011977363.1 |

In another aspect, said construct further includes a promoter, a terminator or stop sequence, a gene that confers resistance to an antibiotic (a "selective marker"), a reporter protein, or a combination thereof.

In another aspect, the DNA construct has the following genetic components: (1) one or more promoters, (2) a gene that expresses a riboswitch, (3) a gene that expresses amyloid precursor protein, (4) a gene that expresses transferrin, (5) a gene that expresses TonB, (6) a gene that expresses a reporter protein (optional), (6) one or more terminators or stop sequences.

In an alternative aspect, the DNA construct has the following genetic components: (1) one or more promoters, (2) a gene that expresses β-amyloid receptor, (3) a gene that expresses amyloid precursor protein, (4) a gene that expresses a riboswitch, (5) a gene that expresses transferrin, (6) a gene that expresses TonB, (7) a gene that expresses a reporter protein (optional), and (8) one or more terminators or stop sequences.

In still another aspect, the DNA construct has the following genetic components: (1) one or more ribosomal binding sites, (2) one or more promoters, (3) a gene that expresses β-amyloid receptor, (4) a gene that expresses amyloid precursor protein, (5) a LAC operon, (6) a gene that expresses transferrin, (7) a gene that expresses TonB, and (8) a gene that expresses a reporter protein (optional).

In one aspect, the construct includes a regulatory sequence. In a further aspect, the regulatory sequence is already incorporated into a vector such as, for example, a plasmid, prior to genetic manipulation of the vector. In another aspect, the regulatory sequence can be incorporated into the vector through the use of restriction enzymes or any other technique known in the art.

In one aspect, the regulatory sequence is an operon such as, for example, the LAC operon. As used herein, an "operon" is a segment of DNA containing a group of genes wherein the group is controlled by a single promoter. Genes included in an operon are all transcribed together. In a further aspect, the operon is a LAC operon and can be induced when lactose crosses the cell membrane of the biological device.

In one aspect, the regulatory sequence is a promoter. The term "promoter" refers to a DNA sequence capable of controlling the expression of a coding sequence. In one aspect, the coding sequence to be controlled is located 3' to the promoter. In another aspect, the promoter is derived from a native gene. In an alternative aspect, the promoter is composed of multiple elements derived from different genes and/or promoters. A promoter can be assembled from elements found in nature, from artificial or synthetic elements, or from a combination thereof. It is understood by those skilled in the art that different promoters can direct the expression of a gene in different tissues or cell types, at different stages of development, in response to different environmental or physiological conditions, and/or in different species. In one aspect, the promoter functions as a switch to activate the expression of a gene.

In one aspect, the promoter is "constitutive." A constitutive promoter is a promoter that causes a gene to be expressed in most cell types at most times. In another aspect, the promoter is "regulated." A regulated promoter is a promoter that becomes active in response to a specific stimulus. A promoter may be regulated chemically, such as, for example, in response to the presence or absence of a particular metabolite (e.g., lactose or tryptophan), a metal ion, a molecule secreted by a pathogen, or the like. A promoter may also be regulated physically, such as, for example, in response to heat, cold, water stress, salt stress, oxygen concentration, illumination, wounding, or the like.

Promoters that are useful to drive expression of the nucleotide sequences described herein are numerous and familiar to those skilled in the art. Suitable promoters include, but are not limited to, the following: T3 promoter, T7 promoter, an iron promoter, and GAL1 promoter. In one aspect, the promoter is an iron promoter. In a further aspect, the iron promoter has SEQ ID NO. 4. In another aspect, the promoter is the native GAL1 promoter found in the plasmid pYES2. Variants of these promoters are also contemplated. The skilled artisan will be able to use site-directed mutagenesis and/or other mutagenesis techniques to modify the promoters to promote more efficient function. The promoter may be positioned, for example, at about 10-100 nucleotides from a ribosomal binding site. In another aspect, the promoter is positioned before the gene that expresses amyloid precursor protein, the gene that expresses transferrin, the gene that expresses TonB, the gene that expresses β-amyloid, or a combination thereof. In an alternative aspect, several different promoters can be used in the same DNA construct.

In one aspect, the promoter is a GAL1 promoter. In another aspect, the GAL1 promoter is native to the plasmid used to create the vector. In another aspect, a GAL1 promoter is positioned before any or all genetic components present in the device. In an another aspect, the promoter is a GAL1 promoter obtained from or native to the pYES2 plasmid.

In another aspect, the promoter is a T7 promoter. In a further aspect, the T7 promoter is native to the plasmid used to create the vector. In still another aspect, the GAL1 promoter is positioned before any or all of the genes in the construct, or is positioned before the LAC operon. In yet another aspect, the promoter is a T7 promoter obtained from or native to the pETDuet-1 plasmid.

In another aspect, the regulatory sequence is a terminator or stop sequence. As used herein, a "terminator" is a sequence of DNA that marks the end of a gene or operon to be transcribed. In a further aspect, the terminator is an intrinsic terminator or a Rho-dependent transcription terminator. As used herein, an intrinsic terminator is a sequence wherein a hairpin structure can form in the nascent transcript that disrupts the mRNA/DNA/RNA polymerase complex. As used herein, a Rho-dependent transcription terminator requires a Rho factor protein complex to disrupt the mRNA/DNA/RNA polymerase complex. In one aspect, the terminator is a T7 terminator. In an alternative aspect, the terminator is a CYC1 terminator obtained from or native to the pYES2 plasmid. In still another aspect, the DNA construct can include multiple terminators. In one aspect, the terminator is native to the vector in which the DNA construct is incorporated. In an alternative aspect, a terminator is positioned after each gene of interest in the 5' to 3' direction.

In a further aspect, the regulatory sequence includes both a promoter and a terminator or stop sequence. In a still further aspect, the regulatory sequence can include multiple promoters or terminators. Other regulatory elements, such as enhancers, are also contemplated. Enhancers may be located from about 1 to about 2000 nucleotides in the 5' direction from the start codon of the DNA to be transcribed, or may be located 3' to the DNA to be transcribed. Enhancers may be "cis-acting," that is, located on the same molecule of DNA as the gene whose expression they affect.

In another aspect, the vector contains one or more ribosomal binding sites. As used herein, a "ribosomal binding site" is a sequence of nucleotides located 5' to the start codon of an mRNA that recruits a ribosome to initiate protein translation. In one aspect, the ribosomal binding site can be positioned before any or all genes in a DNA construct, or a before a subset of genes in a DNA construct.

In one aspect, when the vector is a plasmid, the plasmid can also contain a multiple cloning site or polylinker. In a further aspect, the polylinker contains recognition sites for multiple restriction enzymes. The polylinker can contain up to 2, 3, 4, 5, 6, 7, 8, 9, 10, 11, 12, 13, 14, 15, 16, 17, 18, 19, 20, or more than 20 recognition sites for multiple restriction enzymes. Further, restriction sites may be added, disabled, or removed as required, using techniques known in the art. In one aspect, the plasmid contains restriction sites for any known restriction enzyme such as, for example, HindIII, KpnI, SacI, BamHI, BstXI, EcoRI, BsaBI, NotI, XhoI, SphI, XbaI, ApaI, SalI, ClaI, EcoRV, PstI, SmaI, SpeI, EagI, SacII, or any combination thereof. In a further aspect, the plasmid contains more than one recognition site for the same restriction enzyme.

In one aspect, the restriction enzyme can cleave DNA at a palindromic or an asymmetrical restriction site. In a further aspect, the restriction enzyme cleaves DNA to leave blunt ends; in an alternative aspect, the restriction enzyme cleaves DNA to leave "sticky" or overhanging ends. In another aspect, the enzyme can cleave DNA a distance of from 20 bases to over 1000 bases away from the restriction site. A variety of restriction enzymes are commercially available and their recognition sequences, as well as instructions for use (e.g., amount of DNA needed, precise volumes of reagents, purification techniques, as well as information about salt concentration, pH, optimum temperature, incubation time, and the like) are provided by enzyme manufacturers.

In one aspect, a plasmid with a polylinker containing one or more restriction sites can be digested with one restriction enzyme and a nucleotide sequence of interest can be ligated into the plasmid using a commercially-available DNA ligase enzyme. Several such enzymes are available, often as kits containing all reagents and instructions required for use. In another aspect, a plasmid with a polylinker containing two or more restriction sites can be simultaneously digested with two restriction enzymes and a nucleotide sequence of interest can be ligated into the plasmid using a DNA ligase enzyme. Using two restriction enzymes provides an asymmetric cut in the DNA, allowing for insertion of a nucleotide sequence of interest in a particular direction and/or on a particular strand of the double-stranded plasmid. Since RNA synthesis from a DNA template proceeds from 5' to 3', usually starting just after a promoter, the order and direction of elements inserted into a plasmid can be especially important. If a plasmid is to be simultaneously digested with multiple restriction enzymes, these enzymes must be compatible in terms of buffer, salt concentration, and other incubation parameters.

In some aspects, prior to ligation using a ligase enzyme, a plasmid that has been digested with a restriction enzyme is treated with an alkaline phosphatase enzyme to remove 5' terminal phosphate groups. This prevents self-ligation of the plasmid and thus facilitates ligation of heterologous nucleotide fragments into the plasmid.

In one aspect, different genes can be ligated into a plasmid in one pot. In this aspect, the genes will first be digested with restriction enzymes. In certain aspects, the digestion of genes with restriction enzymes provides multiple pairs of matching 5' and 3' overhangs that will spontaneously assemble the genes in the desired order. In another aspect, the genes and components to be incorporated into a plasmid can be assembled into a single insert sequence prior to insertion into the plasmid. In a further aspect, a DNA ligase enzyme can be used to assist in the ligation process.

In another aspect, the ligation mix may be incubated in an electromagnetic chamber. In one aspect, this incubation lasts for about 1 minute, about 2 minutes, about 5 minutes, about 10 minutes, about 15 minutes, about 20 minutes, about 30 minutes, or about 1 hour.

The DNA construct described herein can be part of a vector. In general, plasmid vectors containing replicon and control sequences that are derived from species compatible with the host cell are used in connection with the hosts. The vector ordinarily carries a replication site as well as marking sequences that are capable of performing phenotypic selection in transformed cells. Plasmid vectors are well known and are commercially available. Such vectors include, but are not limited to, pWLneo, pSV2cat, pOG44, pXT1, pSG, pSVK3, pBSK, pBR322, pYES, pYES2, pBSKII, pUC, pUC19, and pETDuet-1 vectors.

Plasmids are double-stranded, autonomously-replicating, genetic elements that are not integrated into host cell chromosomes. Further, these genetic elements are usually not part of the host cell's central metabolism. In bacteria, plasmids may range from 1 kilobase (kb) to over 200 kb. Plasmids can be engineered to encode a number of useful traits including the production of secondary metabolites, antibiotic resistance, the production of useful proteins, degradation of complex molecules and/or environmental toxins, and others. Plasmids have been the subject of much research in the field of genetic engineering, as plasmids are convenient expression vectors for foreign DNA in, for example, microorganisms. Plasmids generally contain regulatory elements such as promoters and terminators and also usually have independent replication origins. Ideally, plasmids will be present in multiple copies per host cell and will contain selectable markers (such as genes for antibiotic resistance) to allow the skilled artisan to select host cells that have been successfully transfected with the plasmids (for example, by growing the host cells in a medium containing the antibiotic).

In one aspect, the vector encodes a selective marker. In a further aspect, the selective marker is a gene that confers resistance to an antibiotic. In certain aspects, during fermentation of host cells transformed with the vector, the cells are contacted with the antibiotic. For example, the antibiotic may be included in the culture medium. Cells that have not successfully been transformed cannot survive in the presence of the antibiotic; only cells containing the vector that confers antibiotic resistance can survive. Optimally, only cells containing the vector to be expressed will be cultured, as this will result in the highest production efficiency of the desired gene products (e.g., proteins). Cells that do not contain the vector would otherwise compete with transformed cells for resources. In one aspect, the antibiotic is tetracycline, neomycin, kanamycin, ampicillin, hygromycin, chloramphenicol, amphotericin B, bacitracin, carbapenam, cephalosporin, ethambutol, fluoroquinolones, isoniazid, methicillin, oxacillin, vancomycin, streptomycin, quinolones, rifampin, rifampicin, sulfonamides, cephalothin, erythromycin, gentamycin, penicillin, other commonly-used antibiotics, or a combination thereof.

In certain aspects, the DNA construct can include a gene that expresses a reporter protein. The selection of the reporter protein can vary. For example, the reporter protein can be a yellow fluorescent protein, a red fluorescent protein, a green fluorescent protein, or a cyan fluorescent protein. In one aspect, the reporter protein is a yellow fluorescent protein and the gene that expresses the reporter protein has SEQ ID NO. 1 or at least 70% homology thereto, at least 75% homology thereto, at least 80% homology thereto, at least 85% homology thereto, at least 90% homology thereto, or at least 95% homology thereto. In another aspect, the reporter protein is a green fluorescent protein and the gene that expresses the reporter protein has SEQ ID NO. 9 or at least 70% homology thereto, at least 75% homology thereto, at least 80% homology thereto, at least 85% homology thereto, at least 90% homology thereto, or at least 95% homology thereto. The amount of fluorescence that is produced by the biological device can be correlated to the amount of DNA incorporated into the microbial host cells. The fluorescence produced by the device can be detected and quantified using techniques known in the art. For example, spectrofluorometers are typically used to measure fluorescence. The Examples provide exemplary procedures for measuring the amount of fluorescence produced as a result of the expression of DNA.

In one aspect, the construct includes the following genetic components: (a) a gene that expresses amyloid precursor protein, (b) a gene that expresses transferrin; (c) a gene that expresses TonB; and (d) a gene that expresses a reporter protein (optional). In some aspects, the construct omits the gene that expresses transferrin.

In another aspect, construct includes (a) a gene that expresses a reporter protein (optional); (b) gene that expresses amyloid precursor protein, (c) a gene that expresses transferrin, (d) a gene that expresses TonB, (e) a gene that expresses a ribosomal switch, and (f) a gene that expresses an iron promoter.

In another aspect, construct includes from 5' to 3' the following genetic components in the following order: (a) a gene that expresses a reporter protein (optional); (b) gene that expresses amyloid precursor protein, (c) a gene that expresses transferrin, and (d) a gene that expresses TonB. In some aspects, a simplified construct is provided that omits the gene that expresses transferrin.

In another aspect, construct includes from 5' to 3' the following genetic components in the following order: (a) a gene that expresses a protein (optional), (b) a gene that expresses a ribosomal switch, (c) gene that expresses amyloid precursor protein, (d) a gene that expresses transferrin, and (e) a gene that expresses TonB. In some aspects, a simplified construct is provided that omits the gene that expresses transferrin.

In another aspect, construct includes from 5' to 3' the following genetic components in the following order: (a) a gene that expresses a reporter protein (optional), (b) a gene that expresses a ribosomal switch, (c) gene that expresses amyloid precursor protein, (d) a gene that expresses transferrin, (e) a gene that expresses an iron promoter, and (f) a gene that expresses TonB.

In one aspect, the construct is a pYES2 or pBSKII plasmid having from 5' to 3' the following genetic components in the following order: (a) gene that expresses amyloid precursor protein, (b) a gene that expresses transferrin, and (c) a gene that expresses TonB. In another aspect, the construct is a pBSKII plasmid having from 5' to 3' the following genetic components in the following order: (a) a gene that expresses amyloid precursor protein and (b) a gene that expresses TonB.

In another aspect, the construct is a pYES2 or pBSKII plasmid having from 5' to 3' the following genetic components in the following order: (a) a gene that expresses a reporter protein (optional), (b) gene that expresses amyloid precursor protein, (c) a gene that expresses transferrin, and (d) a gene that expresses TonB. In another aspect, the construct is a pYES2 or pBSKII plasmid having from 5' to 3' the following genetic components in the following order: (a) a gene that expresses a reporter protein (optional), (b) gene that expresses amyloid precursor protein, (c) a gene that expresses a ribosomal switch, (d) a gene that expresses transferrin, and (e) a gene that expresses TonB. In some aspects a simplified construct is provided in a pBSKII plasmid that omits the gene that expresses transferrin.

In another aspect, the construct is a pYES2 or pBSKII plasmid having from 5' to 3' the following genetic components in the following order: (a) a gene that expresses a reporter protein (optional), (b) gene that expresses amyloid precursor protein, (c) a gene that expresses a ribosomal switch, (d) a gene that expresses transferrin, (e) a gene that expresses an iron promoter, and (f) a gene that expresses TonB.

In another aspect, the construct is a pYES2 or pBSKII plasmid having from 5' to 3' the following components in the following order: (a) a GAL1 promoter, (b) a yellow fluorescent reporter protein (optional), (c) a CYC1 terminator, (d) a GAL1 promoter, (e) a gene that expresses amyloid precursor protein, (f) a CYC1 terminator, (g) a gene that expresses a riboswitch, (h) an iron promoter, (i) a gene that expresses transferrin, (j) a CYC1 terminator, (k) a GAL1 promoter, and (1) a gene that expresses TonB. In a further aspect, the construct is a pBSKII plasmid having from 5' to 3' the following components in the following order: (a) a T7 promoter, (b) a gene that expresses amyloid precursor protein, (c) a ene that expresses a riboswitch, (d) a gene that expresses TonB, and (e) a gene that expresses a yellow fluorescent reporter protein (optional).

In another aspect, the construct comprises from 5' to 3' the following genetic components in the following order: (a) a GAL1 promoter, (b) a yellow fluorescent reporter protein having SEQ ID NO. 1 or at least 70% homology thereto (optional), (c) a CYC1 terminator, (d) a GAL1 promoter, (e) a gene that expresses amyloid precursor protein having SEQ ID NO. 3 or at least 70% homology thereto, (f) a CYC1 terminator, (f) a gene that expresses a riboswitch having SEQ ID NO. 2 or at least 70% homology thereto, (g) an iron promoter having SEQ ID NO. 4 or at least 70% homology thereto, (h) a gene that expresses transferrin having SEQ ID NO. 5 or at least 70% homology thereto, (j) a CYC1 terminator, (k) a GAL1 promoter, and (1) a gene that expresses TonB having SEQ ID NO. 6 or at least 70% homology thereto.

In one aspect, the construct comprises (a) a gene that expresses β-amyloid receptor, (b) a gene that expresses a reporter protein (optional); (c) gene that expresses amyloid precursor protein, (d) a gene that expresses transferrin, (e) a gene that expresses TonB, (f) a gene that expresses a ribosomal switch, and (g) a gene that expresses an iron promoter.

In another aspect, the construct comprises from 5' to 3' the following genetic components in the following order: (a) a gene that expresses β-amyloid receptor, (b) a gene that expresses a reporter protein (optional); (c) gene that expresses amyloid precursor protein, (d) a gene that expresses transferrin, and (e) a gene that expresses TonB.

In one aspect, the construct comprises from 5' to 3' the following genetic components in the following order: (a) a gene that expresses β-amyloid receptor, (b) a gene that expresses a reporter protein (optional), (c) a gene that expresses a ribosomal switch, (d) gene that expresses amyloid precursor protein, (e) a gene that expresses transferrin, and (f) a gene that expresses TonB.

In one aspect, the construct comprises from 5' to 3' the following genetic components in the following order: (a) a gene that expresses β-amyloid receptor, (b) a gene that expresses a reporter protein (optional), (c) a gene that expresses a ribosomal switch, (d) gene that expresses amyloid precursor protein, (e) a gene that expresses transferrin, (f) a gene that expresses an iron promoter, and (g) a gene that expresses TonB.

In one aspect, the construct is a pYES2 or pBSKII plasmid having from 5' to 3' the following genetic components in the following order: (a) a gene that expresses β-amyloid receptor, (b) a gene that expresses amyloid precursor protein, (c) a gene that expresses transferrin, and (d) a gene that expresses TonB.

In another aspect, the construct is a pYES2 or pBSKII plasmid having from 5' to 3' the following genetic components in the following order: (a) a gene that expresses β-amyloid receptor, (b) a gene that expresses a reporter protein (optional), (c) a gene that expresses amyloid precursor protein, (d) a gene that expresses transferrin, and (e) a gene that expresses TonB.

In another aspect, the construct is a pYES2 or pBSKII plasmid having from 5' to 3' the following genetic components in the following order: (a) a gene that expresses β-amyloid receptor, (b) a gene that expresses a reporter protein (optional), (c) a gene that expresses amyloid precursor protein, (d) a gene that expresses a ribosomal switch, (e) a gene that expresses transferrin, and (f) a gene that expresses TonB.

In another aspect, the construct is a pYES2 or pBSKII plasmid having from 5' to 3' the following genetic components in the following order: (a) a gene that expresses β-amyloid receptor, (b) a gene that expresses a reporter protein (optional), (c) a gene that expresses amyloid precursor protein, (d) a gene that expresses a ribosomal switch, (e) a gene that expresses an iron promoter, (f) a gene that expresses transferrin, and (g) a gene that expresses TonB.

In another aspect, the construct is a pYES2 or pBSKII plasmid having from 5' to 3' the following components in the following order: (a) a GAL1 promoter, (b) a gene that expresses β-amyloid receptor, (c) a CYC1 terminator, (d) a GAL1 promoter, (e) a gene that expresses a green fluorescent reporter protein (optional), (f) a CYC1 terminator, (g) a GAL1 promoter, (h) a gene that expresses an amyloid precursor protein, (i) a CYC1 terminator, (j) a gene that expresses a riboswitch, (k) an iron promoter, (1) a gene that expresses transferrin, (m) a CYC1 terminator, (n) a GAL1 promoter, and (o) a gene that expresses TonB.

In another aspect, the construct comprises from 5' to 3' the following genetic components in the following order: (a) a GAL1 promoter, (b) a gene that expresses β-amyloid receptor having SEQ ID NO. 8 or at least 70% homology thereto, (c) a CYC1 terminator, (d) a GAL1 promoter, (e) a gene that expresses a green fluorescent reporter protein having SEQ ID NO. 9 or at least 70% homology thereto (optional), (f) a CYC1 terminator, (g) a GAL1 promoter, (h) a gene that expresses an amyloid precursor protein having SEQ ID NO. 3 or at least 70% homology thereto, (i) a CYC1 terminator, (j) a gene that expresses a riboswitch having SEQ ID NO. 2 or at least 70% homology thereto, (k) an iron promoter having SEQ ID NO. 4 or at least 70% homology thereto, (1) a gene that expresses transferrin having SEQ ID NO. 5 or at least 70% homology thereto, (m) a CYC1 terminator, (n) a GAL1 promoter, and (n) a gene that expresses TonB having SEQ ID NO. 6 or at least 70% homology thereto.

In a further aspect, the DNA construct has SEQ ID NO. 10.

In one aspect, the construct includes (a) a gene that expresses β-amyloid receptor, (b) a gene that expresses a reporter protein (optional); (c) gene that expresses amyloid precursor protein, (d) a gene that expresses transferrin, (e) a gene that expresses TonB, and (f) a gene that expresses an iron promoter.

In still another aspect, the construct is a pETDuet-1 plasmid having from 5' to 3' the following genetic components in the following order: (a) a gene that expresses β-amyloid receptor, (b) a gene that expresses amyloid precursor protein, (c) a gene that expresses transferrin, and (d) a gene that expresses TonB.

In still another aspect, the construct is a pETDuet-1 plasmid having from 5' to 3' the following genetic components in the following order: (a) a gene that expresses a reporter protein (optional), (b) a gene that expresses β-amyloid receptor, (c) a gene that expresses amyloid precursor protein, (d) a gene that expresses transferrin, and (e) a gene that expresses TonB.

In still another aspect, the construct is a pETDuet-1 plasmid having from 5' to 3' the following genetic components in the following order: (a) a gene that expresses a reporter protein (optional), (b) a gene that expresses β-amyloid receptor, (c) a gene that expresses amyloid precursor protein, (d) an iron promoter, (e) a gene that expresses transferrin, and (f) a gene that expresses TonB.

In one aspect, the construct comprises from 5' to 3' the following components in the following order: (a) a gene that expresses a reporter protein (optional), (b) a ribosomal binding site, (c) a gene that expresses β-amyloid receptor, (d) a ribosomal binding site, (e) a gene that expresses amyloid precursor protein, (f) a T7 promoter, (g) a LAC operon, (h) a ribosomal binding site, (i) an iron promoter, (j) a ribosomal binding site, (k) a gene that expresses transferrin, (l) a ribosomal binding site, and (m) a gene that expresses TonB.

In an alternative aspect, the DNA construct has SEQ ID NO. 11.

FIGS. 2, 3, 4, 5, 11, and 12 provide non-limiting examples of three DNA constructs described herein.

Exemplary methods for producing the DNA constructs described herein are provided in the Examples. Restriction enzymes and purification techniques known in the art can be used to assemble the DNA constructs. Backbone plasmids and synthetic inserts can be mixed together for ligation purposes at different ratios such as, for example, 1:1, 1:2, 1:3, 1:4, and up to 1:5. In one aspect, the ratio of the backbone plasmid to synthetic insert is 1:4. After the vector comprising the DNA construct has been produced, the resulting vector can be incorporated into the host cells using the methods described below.

II. Biological Devices

In one aspect, a "biological device" is formed when a microbial cell is transfected with any of the DNA constructs described herein. The biological devices are generally composed of microbial host cells, where the host cells are transformed with a DNA construct as described herein.

In one aspect, the DNA construct is carried by the expression vector into the cell and is separate from the host cell's genome. In another aspect, the DNA construct is incorporated into the host cell's genome. In still another aspect, incorporation of the DNA construct into the host cell enables the host cell to produce amyloid precursor protein and TonB, devices that can be used in the study of Alzheimer's disease, and/or devices and extracts that can be used to detect Alzheimer's disease in suspected and pre-clinical patients. "Heterologous" genes and proteins are genes and proteins that have been experimentally inserted into a cell that are not normally expressed by that cell. A heterologous gene may be cloned or derived from a different cell type or species than the recipient cell or organism. Heterologous genes may be introduced into cells by transfection or transformation.

An "isolated" nucleic acid is one that has been separated from other nucleic acid molecules and/or cellular material (peptides, proteins, lipids, saccharides, and the like) normally present in the natural source of the nucleic acid. An "isolated" nucleic acid may optionally be free of the flanking sequences found on either side of the nucleic acid as it naturally occurs. An isolated nucleic acid can be naturally occurring, can be chemically synthesized, or can be a cDNA molecule (i.e., is synthesized from an mRNA template using reverse transcriptase and DNA polymerase enzymes).

"Transformation" or "transfection" as used herein refers to a process for introducing heterologous DNA into a host cell. Transformation can occur under natural conditions or may be induced using various methods known in the art. Many methods for transformation are known in the art and the skilled practitioner will know how to choose the best transformation method based on the type of cells being transformed. Methods for transformation include, for example, viral infection, electroporation, lipofection, chemical transformation, and particle bombardment. Cells may be stably transformed (i.e., the heterologous DNA is capable of replicating as an autonomous plasmid or as part of the host chromosome) or may be transiently transformed (i.e., the heterologous DNA is expressed for only a limited period of time).

"Competent cells" refers to microbial cells capable of taking up heterologous DNA. Competent cells can be purchased from a commercial source, or cells can be made competent using procedures known in the art. Exemplary procedures for producing competent cells are provided in the Examples.

The host cells as referred to herein include their progeny, which are any and all subsequent generations formed by cell division. It is understood that not all progeny may be identical due to deliberate or inadvertent mutations. A host cell may be "transfected" or "transformed" which refers to a process by which exogenous nucleic acid is transferred or introduced into the host cell.

The host cells can be naturally-occurring cells or "recombinant" cells. Recombinant cells are distinguishable from naturally-occurring cells in that naturally-occurring cells do not contain heterologous DNA introduced through molecular cloning procedures. In one aspect, the host cell is a prokaryotic cell such as, for example, *Escherichia coli*. In other aspects, the host cell is a eukaryotic cell such as, for example, the yeast *Saccharomyces cerevisiae*. Host cells transformed with the DNA construct described herein are referred to as "biological devices."

The DNA construct is first delivered into the host cell. In one aspect, the host cells are naturally competent (i.e., able to take up exogenous DNA from the surrounding environment). In another aspect, cells must be treated to induce artificial competence. This delivery may be accomplished in vitro, using well-developed laboratory procedures for transforming cell lines. Transformation of bacterial cell lines can be achieved using a variety of techniques. One method involves calcium chloride. The exposure to the calcium ions renders the cells able to take up the DNA construct. Another method is electroporation. In this technique, a high-voltage electric field is applied briefly to cells, producing transient holes in the membranes of the cells through which the vector containing the DNA construct enters. Another method involves exposing intact yeast cells to alkali cations such as, for example, lithium. In one aspect, this method includes exposing yeast to lithium acetate, polyethylene glycol, and single-stranded DNA such as, for example, salmon sperm DNA. Without wishing to be bound by theory, the single-stranded DNA is thought to bind to the cell wall of the yeast, thereby blocking plasmids from binding. The plasmids are then free to enter the yeast cell. Enzymatic and/or electromagnetic techniques can also be used alone, or in combination with other methods, to transform microbial cells. Exemplary procedures for transforming yeast and bacteria with specific DNA constructs are provided in the Examples. In certain aspects, two or more types of DNA can be incorporated into the host cells. Thus, different metabolites can be produced from the same host cells at enhanced rates.

III. Preparation of Devices and Extracts

The biological devices described herein are useful in the production of amyloid precursor protein and TonB, for the production of devices that can be used in the study of Alzheimer's disease, and for the production of devices and extracts that can be used to detect Alzheimer's disease in suspected and pre-clinical patients. Once the DNA construct has been incorporated into the host cell, the cells are cultured such that the cells multiply. A satisfactory microbiological culture contains available sources of hydrogen donors and acceptors, carbon, nitrogen, sulfur, phosphorus, inorganic salts, and, in certain cases, vitamins or other growth-promoting substances. For example, the addition of peptone provides a readily-available source of nitrogen and carbon. Furthermore, the use of different types of media results in different growth rates and different stationary phase densities; stationary phase is where secondary metabolite production occurs most frequently. A rich media results in a short doubling time and higher cell density at stationary phase. Minimal media results in slow growth and low final cell densities. Efficient agitation and aeration increase final cell densities.

In one aspect, host cells may be cultured or fermented by any method known in the art. The skilled practitioner will be able to select a culture medium based on the species and/or strain of host cell selected. In certain aspects, the culture medium will contain a carbon source. A variety of carbon sources are contemplated, including, but not limited to: monosaccharides such as glucose and fructose, disaccharides such as lactose or sucrose, oligosaccharides, polysaccharides such as starch, or mixtures thereof. Unpurified mixtures extracted from feedstocks are also contemplated as carbon sources, as are one-carbon substrates such as carbon dioxide and/or methanol in the cases of compatible organisms. The carbon source utilized is limited only by the particular organism being cultured.

Culturing or fermenting of host cells may be accomplished by any technique known in the art. In one aspect, batch fermentation may be conducted. In batch fermentation, the composition of the culture medium is set at the beginning and the system is closed to future artificial alterations. In some aspects, a limited form of batch fermentation may be carried out wherein factors such as oxygen concentration and pH are manipulated, but additional carbon is not added. Continuous fermentation methods are also contemplated. In continuous fermentation, equal amounts of a defined medium are continuously added to and removed from a bioreactor. In other aspects, microbial host cells are immobilized on a substrate. Fermentation may be carried out on any scale and may include methods in which literal "fermentation" is carried out as well as other culture methods that are non-fermentative.

In one aspect, the method involves growing the biological devices described herein for a sufficient time to produce amyloid precursor protein, TonB, transferrin, and/or β-amyloid. The ordinary artisan will be able to choose a culture medium and optimum culture conditions based on the biological identity of the host cells.

In certain aspects, after culturing the biological device to produce the proteins of interest, the host cells of the device can be lysed with one or more enzymes to produce an extract. For example, when the host cells are yeast, the yeast cells can be lysed with lyticase. In one aspect, the lyticase concentration can be 500, 600, 700, 800, 900, or 1000 μL per liter of culture, where any value can be the lower or upper endpoint of a range (e.g., 500 to 900 μL, 600 to 800 μL, etc.).

In addition to enzymes, other components can be used to facilitate lysis of the host cells. In one aspect, chitosan can be used in combination with an enzyme to lyse the host cells. Chitosan is generally composed of glucosamine units and N-acetylglucosamine units and can be chemically or enzymatically extracted from chitin, which is a component of arthropod exoskeletons and fungal and microbial cell walls. In certain aspects, the chitosan can be acetylated to a specific degree of acetylation. In one aspect, the chitosan is from 60% to about 100%, 70% to 90%, 75% to 85%, or is about 80% acetylated. The molecular weight of the chitosan can vary, as well. For example, the chitosan comprises about 3, 4, 5, 6, 7, 8, 9, 10, 11, 12, 13, 14, 15, 16, 17, 18, 19, or 20 glucosamine units and/or N-acetylglucosamine units. In another aspect, the chitosan includes 5 to 7 glucosamine units and/or N-acetylglucosamine units. In one aspect, the chitosan can be added until a concentration of 0.0015, 0.0025, 0.0050, 0.0075, 0.01, 0.015, 0.02, 0.03, 0.04, or 0.05% (v/v) is achieved in the culture, where any value can be a lower or an upper end-point of a range (e.g., 0.005 to 0.02%, 0.0075 to 0.015%, etc.). Still further in this aspect, the chitosan is present at a concentration of 0.01%.

In a further aspect, the amyloid precursor protein, TonB, transferrin, and/or β-amyloid can be collected, separated from the microbial cells (lysed or intact), and/or purified through any technique known in the art such as, for example, extraction, precipitation, ultracentrifugation, filtration, size exclusion chromatography, ion exchange chromatography, affinity chromatography (SDS-PAGE), high-pressure liquid chromatography, electrophoresis, any other technique known in the art, or a combination thereof. In an alternative aspect, the microbial cells secrete the proteins of interest into the culture medium.

In one aspect, the amyloid precursor protein produced by the devices described herein are nanoparticles. In a further aspect, the amyloid precursor protein has an average diameter of from about 50 nm to about 500 nm, or 50 nm, 100 nm 150 nm, 200 nm, 250 nm, 300 nm, 350 nm, 400 nm, 450 nm, or 500 nm, where any value can be a lower and upper endpoint of a range (e.g., 100 nm to 150 nm). In a still further aspect, the diameters of the nanoparticles can be measured using dynamic light scattering (DLS), transmission electron microscopy (TEM), scanning electron microscopy (SEM), atomic force microscopy (AFM), photon correlation spectroscopy (PCS), x-ray diffraction (XRD), or other methods.

In another aspect, the amyloid precursor protein produced by the devices described herein have an average molecular weight of from about. In a further aspect, the amyloid precursor protein has an average diameter of from 10 kDa to 500 kDa, or 10 kDa, 50 kDa, 100 kDa 150 kDa, 200 kDa, 250 kDa, 300 kDa, 350 kDa, 400 kDa, 450 kDa, or 500 kDa, where any value can be a lower and upper endpoint of a range (e.g., 10 kDa to 100 kDa).

In one aspect, compositions composed of the proteins of interest with lysed and/or intact host cells can be used herein where it is not necessary to separate the host cells and other components from the proteins.

In one aspect, the biological devices are cultured in the presence of one or more metals or metal salts to produce amyloid precursor protein and TonB protein. In one aspect, the metal can be iron, copper, zinc, or aluminum. In another aspect, the metal is a single metal. In an alternative aspect, the metal is a mixture of two or more metals. In a still further aspect, the metals can be introduced to solutions containing the proteins of interest as elemental metals or as metal salts. In this aspect, the metal salts can be sulfate salts or chloride salts. In a further aspect, the metals can be present at concentrations of from 0.1 mM to 100 mM, from 0.5 mM to 50 mM, from 1 mM to 10 mM, or at about 2 mM.

IV. Applications of the Devices and Extracts

The biological devices described herein and extracts produced therefrom can be used to detect and quantify the amount of amyloid protein that is present in a subject. As will be discussed below, elevated levels of amyloid proteins is associated with numerous diseases.

Figure 10:
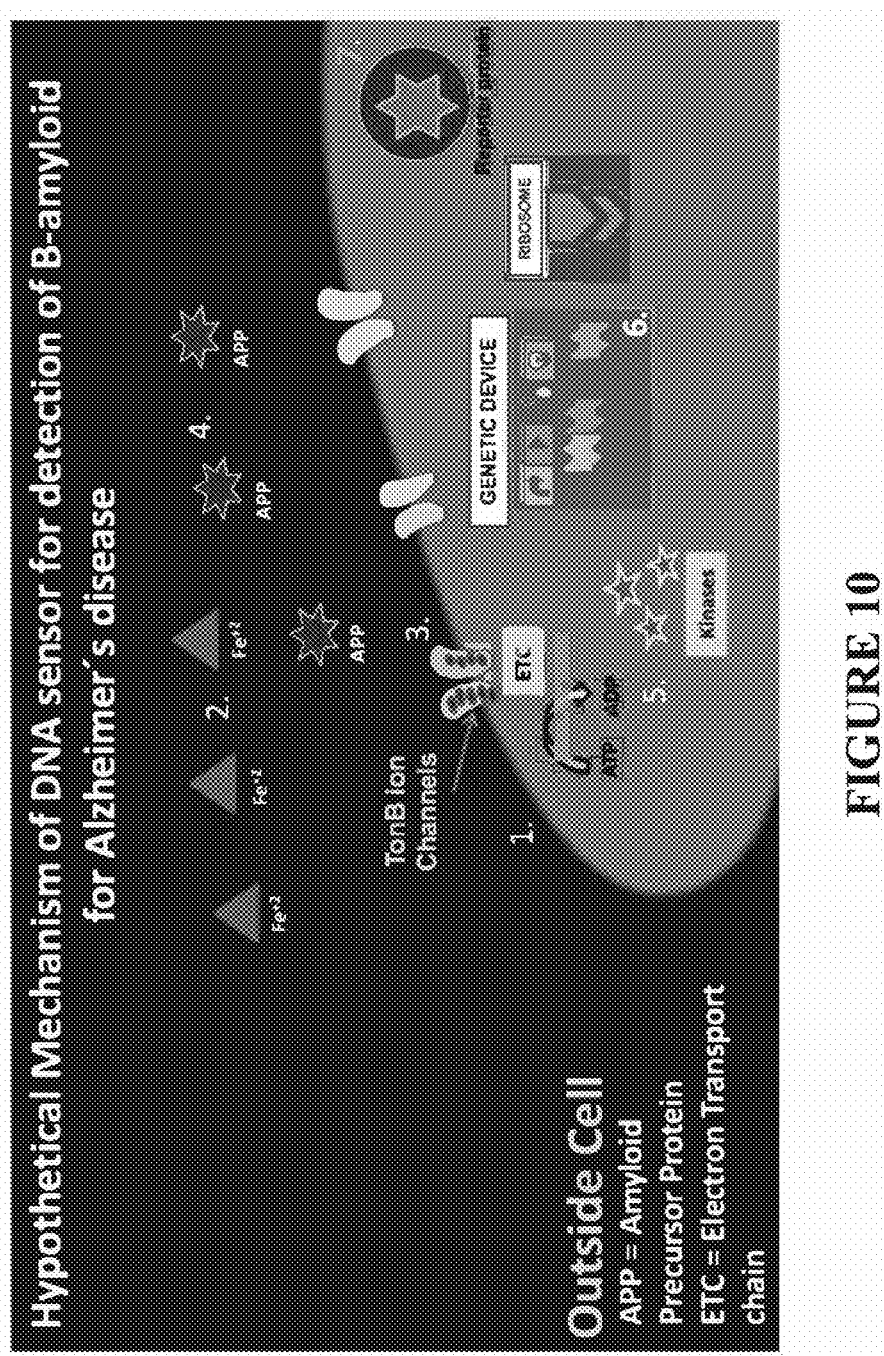
FIG. 10 shows a hypothetical mechanism of a DNA β-amyloid sensor described herein. In this mechanism (1) the device is expressed in a bacterial cell such as *E. coli*. Following this (2) iron ions outside the cell (3) stimulate TonB iron ion channels in the cell membrane. These ion channels then induce the electron transport chain in the cell membrane. (4) Amyloid precursor protein molecules enter the cell and activate second messengers. (5) The second messenger system for amyloid precursor protein phosphorylation (i.e., protein kinases) in the cytoplasm is activated, inducing a metabolic cascade towards activation of the DNA sensor in the cytoplasm. (6) Transcription of the DNA sensor stimulates production of the fluorescent reporter protein. The process concludes with (7) excitation of photons for emission of fluorescence, correlating with amyloid precursor protein concentration.

Without wishing to be bound by theory, a hypothetical mechanism of the principles of operation of a DNA β-amyloid sensor of the present invention is presented in FIG. 10. In this mechanism (1) in one aspect, the device is expressed in a bacterial cell such as *E. coli*. In a further aspect, (2) iron ions outside the cell (3) stimulate TonB iron ion channels in the cell membrane. Further in this aspect, these ion channels then induce the electron transport chain in the cell membrane. (4) In an additional aspect, amyloid precursor protein molecules enter the cell and activate second messengers. In another aspect, (5) the second messenger system for amyloid precursor protein phosphorylation (i.e., protein kinases) in the cytoplasm is activated, inducing a metabolic cascade towards activation of the DNA sensor in the cytoplasm. In a further aspect, (6) transcription of the DNA sensor stimulates production of the fluorescent reporter protein. In a still further aspect, the process concludes with (7) excitation of photons for emission of fluorescence, correlating with amyloid precursor protein concentration.

In one aspect, the amyloid precursor protein and/or TonB protein produced from the biological devices described herein can be used in medical research applications. In this aspect, the amyloid precursor protein and the TonB protein produced using the biological devices described herein are cheaper and/or more cost effective than other commercially-available sources of these same proteins.

In another aspect, the amyloid precursor protein, TonB protein, and/or biological devices described herein can be useful in conducting research into the pathology, pathogenesis, and/or treatment of diseases associated with β-amyloid plaques such as, for example, Alzheimer's disease, Lewy body dementia, inclusion body myositis, cerebral amyloid angiopathy, and brain trauma. Further in this aspect, the amyloid precursor protein, TonB protein, and/or biological devices described herein can be useful in studying the elevated incidence of Alzheimer's disease and similar conditions in patients with Down syndrome or Parkinson's disease.

In one aspect, elevated levels of β-amyloid have been shown to be present in patients with certain cancers. In a further aspect, the amyloid precursor protein, TonB protein, and/or biological devices described herein can be useful in conducting research into the growth, invasiveness, and metastasis of various cancers, including, but not limited to, cancers of the liver, breast, pancreas, colon, prostate, and lung. In a still further aspect, the amyloid precursor protein, TonB protein, and/or biological devices described herein may be useful in elucidating the pathways by which tumors form and/or spread, or may be useful as model targets for chemotherapy agents.

In still another aspect, elevated levels of β-amyloid have been found in a subset of patients with chronic traumatic encephalopathy (CTE), although a definitive link between β-amyloid plaques and CTE has not yet been established. CTE is an increasing problem among amateur and professional athletes and military veterans and further research in this area is needed. In one aspect, the amyloid precursor protein, TonB protein, and/or biological devices described herein can be useful in conducting research into CTE.

In one aspect, patients having type II diabetes exhibit an increased likelihood of developing Alzheimer's disease. In a further aspect, the amyloid precursor protein, TonB protein, and/or biological devices disclosed herein can be useful in predicting whether a diabetic patient is likely to develop Alzheimer's disease or can be used in the development of drugs for diabetic patients to halt the progression of Alzheimer's disease.

In a further aspect, the interaction of amyloid precursor protein, β-amyloid, and/or amyloid plaques with metals can be assessed. In this aspect, the metals can be elemental metals or can be ions. In a further aspect, the metal can be iron, copper, zinc, or aluminum. In another aspect, the metal is a single metal. In an alternative aspect, the metal is a mixture of two or more metals. In a still further aspect, the metals can be introduced to solutions containing the proteins of interest as elemental metals or as metal salts. In this aspect, the metal salts can be sulfate salts or chloride salts. In a further aspect, the metals can be present at concentrations from 0.1 mM to 100 mM, from 0.5 mM to 50 mM, or from 1 mM to 10 mM, or can be about 2 mM.

In one aspect, described herein is a method for measuring the amount of amyloid protein in a subject, the method involving the steps of:
(a) mixing a sample from the subject with the biological device or extract produced therefrom to produce a test sample; and
(b) measuring fluorescence intensity of the test sample.

In another aspect, described herein is a method for diagnosing or predicting a disease associated with elevated levels of amyloid in a subject, the method involving the steps of:
(a) mixing a sample from the subject with the biological device or extract produced therefrom to produce a test sample; and
(b) measuring fluorescence intensity of the test sample.

In one aspect, when metals are added to the culture medium containing the biological devices, the biological devices can be allowed to grow and form colonies. In this aspect, the growth of the biological devices containing the DNA construct described herein can be compared to the growth of cells not containing such a construct. In a further aspect, the growth and behavior of the biological devices can serve as proxies or models for the interaction of metals and amyloid precursor protein, β-amyloid, and/or amyloid plaques, since performing similar experiments in living tissues can be difficult.

In one aspect, biological devices such as those described herein are used as models for in vivo behavior of amyloid precursor protein. In this aspect, without wishing to be bound by theory the TonB protein expressed by the biological devices provides energy for transporting metals, metal complexes, and/or other large products across cell membranes, or acts as an ion channel for metals and metal complexes.

In certain aspects, a fluorescent dye can be added to the patient sample that includes the extracts produced herein. As demonstrated in the Examples, a fluorescent dye can enhance the fluorescence produced by the extract.

Non-limiting examples of fluorescent dyes include, rhodamine, BODIPY®, coumarin and cyanine dyes. Other non-limiting examples of fluorescent dyes include a red fluorescent squarine dye such as 2,4-Bis[1,3,3-trimethyl-2-indolinylidenemethyl] cyclobutenediylium-1,3-dioxolate, an infrared dye such as 2,4 Bis [3,3-dimethyl-2-(1H-benz[e]indolinylidenemethyl)] cyclobutenediylium-1,3-dioxolate, or an orange fluorescent squarine dye such as 2,4-Bis [3,5-dimethyl-2-pyrrolyl] cyclobutenediylium-1,3-diololate, quantum dots, Alexa Fluor® dyes, ANICA, BODIPY® 630/650, BODIPY® 650/665, BODIPY®-FL, BODIPY®-R6G, BODIPY®-TMR, BODIPY™-TRX, Cascade Blue®, CyDye™, including but not limited to Cy2™, Cy3™, and Cy5™, 6-FAM™, Fluorescein, HEX™, 6-JOE, Oregon Green® 488, Oregon Green® 500, Oregon Green® 514, Pacific Blue™ REG, phycobilliproteins including, but not limited to, phycoerythrin and allophycocyanin, Rhodamine Green™, Rhodamine Red™, ROX™, TAMRA™, TET™, tetramethylrhodamine, or Texas Red®.

In one aspect, the fluorescent dye is cyanine dye. In another aspect, the cyanine dye includes functional groups that can form covalent bonds with target proteins. For example, the cyanine dye can include NHS ester groups that can react with amino groups present in a protein. In another aspect, the fluorescent dye is a C2, Cy3, Cy3.5, Cy5, Cy5.5 and Cy7 cyanine dye, where the numerical value is the number of methane groups present in the dye. The absorption and emission maxima, respectively, for these fluors are: FITC (490 nm; 520 nm), Cy3 (554 nm; 568 am), Cy3.5 (581 nm; 588 nm), Cy5 (652 nm: 672 nm), Cy5.5 (682 nm; 703 nm) and Cy7 (755 nm; 778 nm). In another aspect, the fluorescent dye is a sulfo-cyanine dye. In a further aspect, the fluorescent dye is a C3 sulfo-cyanine dye. The sulfo-cyanine dyes manufactured by Lumiprobe and kits thereof can be used herein.

The fluorescent dye can be added directly to the patient sample containing the extract as a solid or solution. In another aspect, a tube or vial can be coated with mixture of the extract and fluorescent dye, where the patient sample is added to the tube or vial.

In a further aspect, biological devices such as those described herein are used in diagnostic tests for the detection of Alzheimer's disease in living patients, including early stages of the disease. In this aspect, the use of these diagnostic tests can identify Alzheimer's patients at an early stage, when few or no symptoms are present, thus enabling physicians and caregivers to start treatment early and delay the progression of the disease. In a still further aspect, the biological devices are used in diagnostic tests for other amyloid-plaque-associated diseases such as, for example, Lewy body dementia, inclusion body myositis, and cerebral amyloid angiopathy. In another aspect, the biological devices can be used in diagnostic tests to determine whether a subject is likely to develop an invasive tumor, or whether a subject's cancer may metastasize or has already metastasized. In still another aspect, the biological devices can be used in diagnostic tests to determine whether patients with type II diabetes are likely to develop Alzheimer's or another form of dementia associated with amyloid plaques.

In one aspect, provided herein is a method for diagnosing Alzheimer's disease and/or determining the predisposition of a patient to develop Alzheimer's disease or diagnosing a pre-Alzheimer's condition. In one aspect, the method for diagnosing or predicting Alzheimer's disease in a subject involves (a) mixing a sample from the subject with the biological device described herein to produce a test sample; and (b) measuring the fluorescence intensity of the test sample. In another aspect, the method for diagnosing or predicting Alzheimer's disease in a subject involves (a) mixing a sample from the subject with an extract produced from the biological devices described herein to produce a test sample; and (b) measuring fluorescence intensity of the test sample. In one aspect, the sample from the patient can be blood, serum, plasma, saliva, spinal fluid, or urine.

After the patient sample has been mixed with the biological device or extract produced from the device, the amount of fluorescence that is subsequently produced is quantified using techniques and instrumentation known in the art. In one aspect, the amount of fluorescence that is produced can be correlated with clinical symptoms indicative of Alzheimer's disease such as, for example, memory loss, disorientation, and mental confusion. In one aspect, the amount of fluorescence from the reporter protein correlates to protein production in media.

After the fluorescence has been quantified, the value is correlated in order to determine if (1) the subject has Alzheimer's disease or (2) if the subject is has pre-Alzheimer's disease or is likely to develop Alzheimer's disease (i.e., predisposed to Alzheimer's disease). In one aspect, a chart or computer program can be used to correlate different fluorescence values to different symptoms or probability of having or contracting Alzheimer's disease. Results from a series of such tests on Alzheimer's, pre-Alzheimer's, and healthy patients are presented in the Examples.

In one aspect, a clinician or medical provider may diagnose a patient with Alzheimer's disease based on the concurrent presence of these three symptoms. Current definitive determinations of Alzheimer's can only be made upon examination of neural tissue after patient death, but certain symptoms such as memory loss, disorientation, and mental confusion are generally simultaneously present in Alzheimer's patients. In one aspect, the devices and compositions described herein can be used to diagnose Alzheimer's disease prior to patient death and without the need for autopsy or removal of brain tissue for histological analysis. In another aspect, the results from use of the devices, compositions, and methods described herein correlate well with a clinical medical diagnosis of Alzheimer's disease and/or of a suspected pre-Alzheimer's condition. In a further aspect, the results from use of the devices, compositions, and methods described herein also correlate with results gleaned from CT scans and/or MRI analyses of Alzheimer's, pre-Alzheimer's, and healthy patients.

In a further aspect, the devices, compositions, and methods described herein can be used to diagnose pre-Alzheimer's conditions in patients exhibiting one or two, but not all three, clinical medical symptoms of Alzheimer's disease (e.g., mental confusion, disorientation, memory loss). In a still further aspect, early diagnosis of pre-Alzheimer's conditions paves the way for therapeutic, medical, and/or pharmaceutical intervention to delay the onset of Alzheimer's disease.

In other aspects, the extracts produced by the devices can be added to patient samples, and the sample subsequently analyzed by Raman spectroscopy. The Raman spectrum if the sample can produce a fingerprint of the patient that is either health, pre-Alzheimers, or diagnosed with Alzheimers. Not wishing to be bound by theory, the extract increases the intensity of certain peaks in the Raman spectrum, which makes it easier to diagnose the different stages of Alzheimers.

V. Aspects

The present disclosure can be described in accordance with the following numbered Aspects, which should not be confused with the claims.

Aspect 1: A DNA construct comprising the following genetic components: (a) a gene that expresses amyloid precursor protein, (b) a gene that expresses transferrin; and (c) a gene that expresses TonB; and optionally (d) a gene that expresses a reporter protein.

Aspect 2: The DNA construct of aspect 1, further comprising a gene that expresses ☐amyloid receptor.

Aspect 3: The DNA construct of aspect 1, further comprising a gene that expresses a riboswitch.

Aspect 4: The DNA construct of aspect 1, wherein the gene that expresses amyloid precursor protein has SEQ ID NO. 3 or at least 70% homology thereto.

Aspect 5: The DNA construct of aspect 1, wherein the gene that expresses transferrin has SEQ ID NO. 5 or at least 70% homology thereto.

Aspect 6: The DNA construct of aspect 1, wherein the gene that expresses TonB has SEQ ID NO. 6 or at least 70% homology thereto.

Aspect 7: The DNA construct of aspect 2, wherein the gene that expresses ☐-amyloid receptor has SEQ ID NO. 8 or at least 70% homology thereto.

Aspect 8: The DNA construct of aspect 3, wherein the gene that expresses a riboswitch has SEQ ID NO. 2 or at least 70% homology thereto.

Aspect 9: The DNA construct of aspect 1, further comprising one or more promoters. Aspect 10: The DNA construct of aspect 9, wherein the promoter is a T3 promoter, a T7 promoter, an iron promoter, or a GAL1 promoter.

Aspect 11: The DNA construct of aspect 10, wherein the promoter comprises an iron promoter and at least one GAL1 promoter.

Aspect 12: The DNA construct of aspect 10, wherein the promoter comprises an iron promoter and at least one T7 promoter.

Aspect 13: The DNA construct of aspect 10, wherein the iron promoter has SEQ ID NO. 4 or at least 70% homology thereto.

Aspect 14: The DNA construct of aspect 1 further comprising at least one ribosomal binding site.

Aspect 15: The DNA construct of aspect 1 further comprising a LAC operon.

Aspect 16: The DNA construct of aspect 1 further comprising a gene that confers resistance to an antibiotic.

Aspect 17: The DNA construct of aspect 16, wherein the antibiotic comprises tetracycline, neomycin, kanamycin, ampicillin, hygromycin, chloramphenicol, amphotericin B, bacitracin, carbapenam, cephalosporin, ethambutol, fluoroquinolones, isoniazid, methicillin, oxacillin, vancomycin, streptomycin, quinolones, rifampin, rifampicin, sulfonamides, cephalothin, erythromycin, gentamycin, penicillin, other commonly-used antibiotics, or a combination thereof.

Aspect 18: The DNA construct of aspect 1 further comprising at least one terminator Aspect 19: The DNA construct of aspect 18, wherein the terminator is a T7 terminator or a CYC1 terminator.

Aspect 20: The DNA construct of aspect 1, wherein the construct comprises a gene that expresses a reporter protein.

Aspect 21: The DNA construct of aspect 20, wherein the fluorescent reporter protein is a red fluorescent protein, a green fluorescent protein, a cyan fluorescent protein, or a yellow fluorescent protein.

Aspect 22: The DNA construct of aspect 21, wherein the fluorescent reporter protein is a yellow fluorescent protein.

Aspect 23: The DNA construct of aspect 21, wherein the yellow fluorescent protein has SEQ ID NO. 1 or at least 70% homology thereto.

Aspect 24: The DNA construct of aspect 21, wherein the fluorescent reporter protein is a green fluorescent protein.

Aspect 25: The DNA construct of aspect 24, wherein the green fluorescent protein has SEQ ID NO. 9 or at least 70% homology thereto.

Aspect 26: The DNA construct of aspect 1, wherein the DNA construct comprises (a) gene that expresses amyloid precursor protein, (b) a gene that expresses transferrin, (c) a gene that expresses TonB, (d) a gene that expresses a ribosomal switch, and (e) a gene that expresses an iron promoter.

Aspect 27: The DNA construct of aspect 1, wherein the DNA construct comprises from 5' to 3' the following genetic components in the following order: (a) gene that expresses amyloid precursor protein, (b) a gene that expresses transferrin, and (c) a gene that expresses TonB.

Aspect 28: The DNA construct of aspect 1, wherein the DNA construct comprises from 5' to 3' the following genetic components in the following order: (a) a gene that expresses a ribosomal switch, (b) gene that expresses amyloid precursor protein, (c) a gene that expresses transferrin, and (d) a gene that expresses TonB.

Aspect 29: The DNA construct of aspect 1, wherein the DNA construct comprises from 5' to 3' the following genetic components in the following order: (a) a gene that expresses a ribosomal switch, (b) a gene that expresses amyloid precursor protein, (c) a gene that expresses transferrin, (d) a gene that expresses an iron promoter, and (e) a gene that expresses TonB.

Aspect 30: The DNA construct of aspect 1, wherein the DNA construct comprises from 5' to 3' the following genetic components in the following order: (a) a GAL1 promoter, (b) a gene that expresses amyloid precursor protein, (c) a CYC1 terminator, (d) a gene that expresses a riboswitch, (e) an iron promoter, (f) a gene that expresses transferrin, (g) a CYC1 terminator, (h) a GAL1 promoter, and (i) a gene that expresses TonB.

Aspect 31: The DNA construct of aspect 1, wherein the DNA construct comprises from 5' to 3' the following genetic components in the following order: (a) a GAL1 promoter, (b) a gene that expresses amyloid precursor protein having SEQ ID NO. 3 or at least 70% homology thereto, (c) a CYC1 terminator, (d) a gene that expresses a riboswitch having SEQ ID NO. 2 or at least 70% homology thereto, (e) an iron promoter having SEQ ID NO. 4 or at least 70% homology thereto, (f) a gene that expresses transferrin having SEQ ID NO. 5 or at least 70% homology thereto, (g) a CYC1 terminator, (h) a GAL1 promoter, and (i) a gene that expresses TonB having SEQ ID NO. 6 or at least 70% homology thereto.

Aspect 32: The DNA construct of aspect 1, wherein the DNA construct has SEQ ID NO. 7.

Aspect 33: The DNA construct of aspect 1, wherein the DNA construct comprises (a) a gene that expresses □-amyloid receptor, (b) gene that expresses amyloid precursor protein, (c) a gene that expresses transferrin, (d) a gene that expresses TonB, (e) a gene that expresses a ribosomal switch, and (f) a gene that expresses an iron promoter.

Aspect 34: The DNA construct of aspect 1, wherein the DNA construct comprises from 5' to 3' the following genetic components in the following order: (a) a gene that expresses □-amyloid receptor, (b) gene that expresses amyloid precursor protein, (c) a gene that expresses transferrin, and (d) a gene that expresses TonB.

Aspect 35: The DNA construct of aspect 1, wherein the DNA construct comprises from 5' to 3' the following genetic components in the following order: (a) a gene that expresses □-amyloid receptor, (b) a gene that expresses a ribosomal switch, (c) gene that expresses amyloid precursor protein, (d) a gene that expresses transferrin, and (e) a gene that expresses TonB.

Aspect 36: The DNA construct of aspect 1, wherein the DNA construct comprises from 5' to 3' the following genetic components in the following order: (a) a gene that expresses □-amyloid receptor, (b) a gene that expresses a ribosomal switch, (c) gene that expresses amyloid precursor protein, (d) a gene that expresses transferrin, (e) a gene that expresses an iron promoter, and (f) a gene that expresses TonB.

Aspect 37: The DNA construct of aspect 2, wherein the DNA construct comprises from 5' to 3' the following genetic components in the following order: (a) a GAL1 promoter, (b) a gene that expresses □-amyloid receptor, (c) a CYC1 terminator, (d) a GAL1 promoter, (e) a gene that expresses an amyloid precursor protein, (f) a CYC1 terminator, (g) a gene that expresses a riboswitch, (h) an iron promoter, (i) a gene that expresses transferrin, (j) a CYC1 terminator, (k) a GAL1 promoter, and (l) a gene that expresses TonB.

Aspect 38: The DNA construct of aspect 2, wherein the DNA construct comprises from 5' to 3' the following genetic components in the following order: (a) a GAL1 promoter, (b) a gene that expresses □-amyloid receptor having SEQ ID NO. 8 or at least 70% homology thereto, (c) a CYC1 terminator, (d) a CYC1 terminator, (e) a GAL1 promoter, (f) a gene that expresses an amyloid precursor protein having SEQ ID NO. 3 or at least 70% homology thereto, (g) a CYC1 terminator, (h) a gene that expresses a riboswitch having SEQ ID NO. 2 or at least 70% homology thereto, (i) an iron promoter having SEQ ID NO. 4 or at least 70% homology thereto, (j) a gene that expresses transferrin having SEQ ID NO. 5 or at least 70% homology thereto, (k) a CYC1 terminator, (l) a GAL1 promoter, and (n) a gene that expresses TonB having SEQ ID NO. 6 or at least 70% homology thereto.

Aspect 39: The DNA construct of aspect 2, wherein the DNA construct has SEQ ID NO. 10.

Aspect 40: The DNA construct of aspect 1, wherein the DNA construct comprises (a) a gene that expresses □-amyloid receptor, (b) gene that expresses amyloid precursor protein, (c) a gene that expresses transferrin, (d) a gene that expresses TonB, and (e) a gene that expresses an iron promoter.

Aspect 41: The DNA construct of aspect 2, wherein the DNA construct comprises from 5' to 3' the following genetic components in the following order: (a) a gene that expresses □-amyloid receptor, (b) a gene that expresses amyloid precursor protein, (c) a gene that expresses transferrin, and (d) a gene that expresses TonB.

Aspect 42: The DNA construct of aspect 2, wherein the DNA construct comprises from 5' to 3' the following genetic components in the following order: (a) a ribosomal binding site, (b) a gene that expresses □-amyloid receptor, (c) a ribosomal binding site, (d) a gene that expresses amyloid precursor protein, (e) ribosomal binding site, (f) an iron promoter, (g) a ribosomal binding site, (h) a gene that expresses transferrin, (i) a ribosomal binding site, and (j) a gene that expresses TonB.

Aspect 43: The DNA construct of aspect 2, wherein the DNA construct comprises from 5' to 3' the following genetic components in the following order: (a) a ribosomal binding site, (b) a gene that expresses □-amyloid receptor, (c) a T7 promoter, (d) a LAC operon, (e) a ribosomal binding site, (f) a gene that expresses amyloid precursor protein, (g) ribosomal binding site, (h) an iron promoter, (i) a ribosomal binding site, (j) a gene that expresses transferrin, (k) a ribosomal binding site, and (1) a gene that expresses TonB.

Aspect 44: The DNA construct of aspect 2, wherein the DNA construct comprises from 5' to 3' the following genetic components in the following order: (a) a ribosomal binding site, (b) a gene that expresses □-amyloid receptor having SEQ ID NO. 8 or at least 70% homology thereto, (c) a ribosomal binding site, (d) a gene that expresses amyloid precursor protein having SEQ ID NO. 3 or at least 70% homology thereto, (e) a T7 promoter, (f) a LAC operon, (g) a ribosomal binding site, (h) an iron promoter having SEQ ID NO. 4 or at least 70% homology thereto, (i) a ribosomal binding site, (j) a gene that expresses transferrin having SEQ ID NO. 5 or at least 70% homology thereto, (k) a ribosomal binding site, and (1) a gene that expresses TonB having SEQ ID NO. 6 or at least 70% homology thereto.

Aspect 45: The DNA construct of aspect 2, wherein the DNA construct has SEQ ID NO. 11.

Aspect 46: A vector comprising the DNA construct in any one of aspects 1-45.

Aspect 47: The vector of aspect 46, wherein the vector is a plasmid.

Aspect 48: The vector of aspect 47, wherein the plasmid is pWLneo, pSV2cat, pOG44, pXT1, pSG, pSVK3, pBSK, pBSKII, pYES, pYES2, pUC, pUC19, or pETDuet-1.

Aspect 49: The vector of aspect 48, wherein the plasmid is pYES2.

Aspect 50: The vector of aspect 48, wherein the plasmid is pBSKII.

Aspect 51: The vector of aspect 48, wherein the plasmid is pETDuet-1.

Aspect 52: A biological device comprising host cells transformed with the DNA construct in any one of aspects 1-45.

Aspect 53: The biological device of aspect 52, wherein the host cells comprise fungi or bacteria.

Aspect 54: The biological device of aspect 53, wherein the bacteria comprise *E. coli*.

Aspect 55: The biological device of aspect 53, wherein the fungi comprise yeast.

Aspect 56: The biological device of aspect 55, wherein the yeast comprises *S. cerevisiae*.

Aspect 57: An extract produced by culturing the biological device of aspect 52.

Aspect 58: The extract of aspect 57, wherein the extract is produced by:
(a) culturing the biological device in a culture medium; and
(b) removing the extract from the culture medium.

Aspect 59: The extract of aspect 57, wherein the biological device is cultured in a medium comprising one or more metals or metal salts.

Aspect 60: The extract of aspect 57, wherein the metal or metal salts are iron metal, iron sulfate, copper sulfate, copper chloride, or a combination thereof.

Aspect 61: A method for diagnosing or predicting a disease associated with elevated levels of amyloid in a subject, the method comprising the steps of:
(a) mixing a sample from the subject with an extract of claim 57 to produce a test sample; and
(b) measuring the fluorescence intensity of the test sample.

Aspect 62: The method of aspect 61, wherein the sample comprises blood, serum, plasma, saliva, spinal fluid, or urine.

Aspect 63: The method of aspect 61, wherein the sample is plasma.

Aspect 64: The method of aspect 61, wherein the amyloid is β-amyloid.

Aspect 65: The method of aspect 61, wherein after step (b) correlating the amount of fluorescence to determine if the subject (1) has the disease or (2) is predisposed to the disease.

Aspect 66: The method of aspect 61, wherein the disease is Alzheimer's disease, Lewy body dementia, inclusion body myositis, chronic traumatic encephalopathy, or cerebral amyloid angiopathy.

Aspect 67: The method of aspect 61, wherein the disease is caused by trauma to the brain.

Aspect 68: The method of aspect 61, wherein the disease is cancer.

Aspect 69: The method of aspect 68, wherein the cancer is cancer of the liver, breast, pancreas, colon, prostate, or lung.

Aspect 70: A method for diagnosing or predicting a disease associated with elevated levels of amyloid in a subject, the method comprising the steps of:
(a) mixing a sample from the subject with an extract to produce a test sample, wherein the extract is produced by a biological device comprising host cells transformed with a DNA construct comprising (a) a gene that expresses amyloid precursor protein, (b) a gene that expresses TonB; and optionally (c) a gene that expresses a reporter protein; and
(b) measuring the fluorescence intensity of the test sample.

Aspect 71: The method of aspect 70, wherein the sample comprises blood, serum, plasma, saliva, spinal fluid, or urine.

Aspect 72: The method of aspect 70, wherein the sample is plasma.

Aspect 73: The method of aspect 70, wherein the amyloid is β-amyloid.

Aspect 74: The method of aspect 70, wherein after step (b) correlating the amount of fluorescence to determine if the subject (1) has the disease or (2) is predisposed to the disease.

Aspect 75: The method of aspect 70, further comprising one or more promoters.

Aspect 1: The method of aspect 75, wherein the promoter is a T3 promoter, a T7 promoter, an iron promoter, or a GAL1 promoter.

Aspect 76: The method of aspect 70, wherein the construct further comprises a gene that expresses a riboswitch.

Aspect 77: A method for measuring the amount of amyloid protein in a subject, the method comprising the steps of:
(a) mixing a sample from the subject with an extract of claim 57 to produce a test sample; and
(b) measuring the fluorescence intensity of the test sample.

Aspect 78: The method of aspect 78, wherein after step (b) correlating the amount of fluorescence to the amount of amyloid present in the subject.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperatures, etc.) but some errors and deviations should be accounted for. Unless indicated otherwise, parts are parts by weight, temperature is in ° C. or is at ambient temperature, and pressure is at or near atmospheric. Numerous variations and combinations of reaction conditions (e.g., component concentrations, desired solvents, solvent mixtures, temperatures, pressures, and other reaction ranges and conditions can be used to optimize the product purity and yield obtained from the desired process. Only reasonable and routine experimentation will be required to optimize such processes and conditions.

Preparation of DNA Construct

The DNA construct was composed of genetic components described herein and assembled in plasmid vectors (e.g., pYES2, pBSKII, or pETDuet-1). Sequences of genes and/or proteins with desired properties were identified in GenBank; these include an amyloid precursor protein gene, a TonB gene, a transferrin gene, and a β-amyloid gene. Other genetic parts were also obtained for inclusion in the DNA constructs including, for example, promoter genes (e.g., iron promoter, GAL1 promoter), reporter genes (e.g., yellow fluorescent reporter protein, green fluorescent reporter protein), and terminator sequences (e.g., CYC1 terminator). These genetic parts included restriction sites for ease of insertion into plasmid vectors.

The cloning of the DNA construct into the biological devices was performed as follows. Sequences of individual genes were amplified by polymerase chain reaction using primers that incorporated restriction sites at their 5' ends to facilitate construction of the full sequence to be inserted into the plasmid. Genes were then ligated using standard protocols to form an insert. The plasmid was then digested with restriction enzymes according to directions and using reagents provided by the enzyme's supplier (Promega). The complete insert, containing restriction sites on each end, was then ligated into the plasmid. Successful construction of the insert and ligation of the insert into the plasmid were confirmed by gel electrophoresis. FIG. 1 shows an electrophoresis gel for one DNA construct according to the present invention.

In some instances, a pBSKII plasmid already containing a gene for the amyloid precursor protein was digested with HindIII restriction enzyme according to directions and using reagents provided by the enzyme's supplier (Promega). The complete insert, containing HindIII restriction sites on each end, was then ligated into the plasmid. A ratio of 3 parts backbone vector to 4 parts insert mixture was used for ligation. T4 DNA ligase, ligase buffer (supplied by Promega), and nuclease-free water were added to the mixture of vector and insert.

PCR was used to enhance DNA concentration using a Mastercycler Personal 5332 ThermoCycler (Eppendorf North America) with specific sequence primers and the standard method for amplification (Sambrook, J., E. F. Fritsch, and T. Maniatis, 1989, *Molecular Cloning: A Laboratory Manual*, $2^{nd}$ ed., Vol. 1, Cold Spring Harbor Laboratory Press: Cold Spring Harbor, N.Y.). Digestion and ligation were used to ensure assembly of DNA synthesized parts using restriction enzymes and reagents (PCR master mix of restriction enzymes: XhoI, KpnI, XbaI, EcoRI, BamHI, and HindIII, with alkaline phosphatase and quick ligation kit, all from Promega). DNA was quantified using a NanoVue spectrophotometer (GE Life Sciences) and a standard UV/Visible spectrophotometer using the ratio of absorbances at 260 nm versus 280 nm. In order to verify final ligations, DNA was visualized and purified via electrophoresis using a Thermo EC-150 power supply.

Alternatively, the reaction mixture containing plasmid and insert was placed into an electromagnetic chamber and subjected to a minicurrent (900 mA) magnetic field with a strength of 0.35 Gauss. Successful construction of the insert and ligation of the insert into the plasmid were confirmed by gel electrophoresis.

The DNA construct was made with gene parts fundamental for expression of sequences such as, for example, ribosomal binding sites, native and constitutive promoters, reporter genes, and transcriptional terminators or stops. Backbone plasmids and synthetic inserts can be mixed together for ligation purposes at different ratios ranging from 1:1, 1:2, 1:3, 1:4, and up to 1:5. In one aspect, the ratio of backbone plasmid to synthetic insert is 1:4. The DNA constructs in FIGS. 2, 3, 4, and 5 were assembled using the techniques above.

Figure 2:
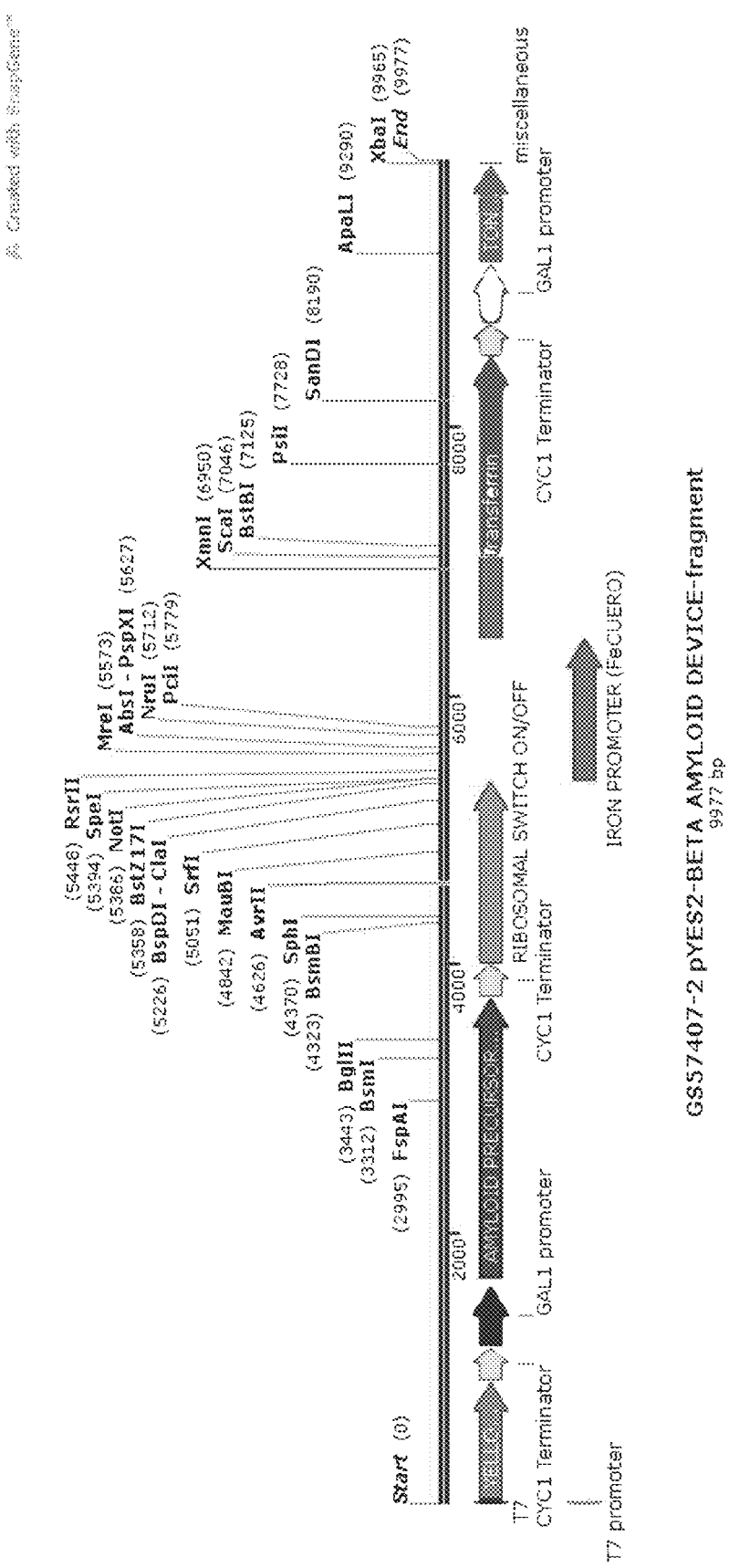
FIG. 2 shows a linear schematic of a vector described herein, wherein the vector has SEQ ID NO. 7.
Figure 3:
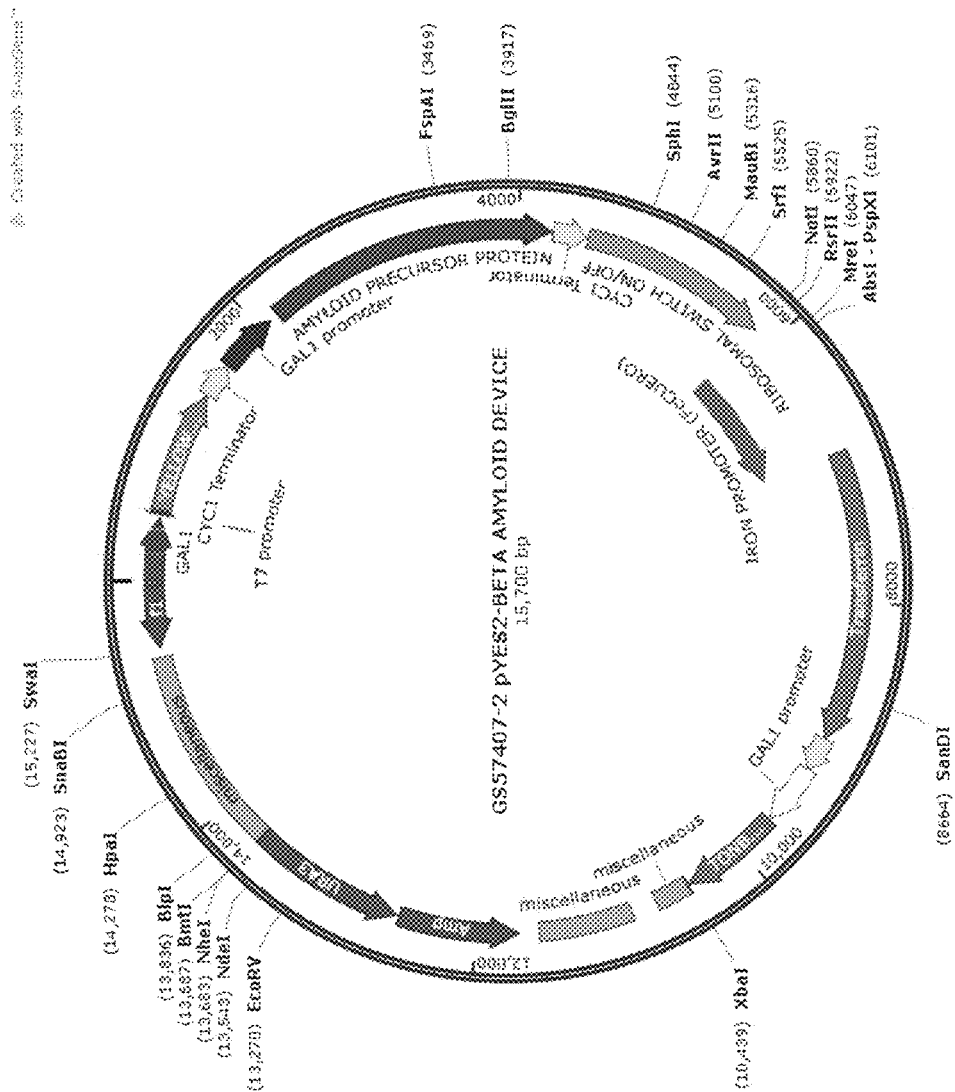
FIG. 3 shows a circular schematic of a vector described herein, wherein the vector has SEQ ID NO. 7.

The DNA device was constructed by assembling a plasmid (pBSKII, pYES2, and pETDuet-1 were all successfully tested) having the following genetic components in the following order: (a) a yellow fluorescent reporter protein having SEQ ID NO. 1, (b) a gene that expresses amyloid precursor protein having SEQ ID NO. 3, (c) a gene that expresses a riboswitch having SEQ ID NO. 2, (d) an iron promoter having SEQ ID NO. 4, (e) a gene that expresses transferrin having SEQ ID NO. 5, and (f) a gene that expresses TonB having SEQ ID NO. 6. One sample DNA device has SEQ ID NO. 7 and is shown in FIGS. 2 and 3.

Figure 4:
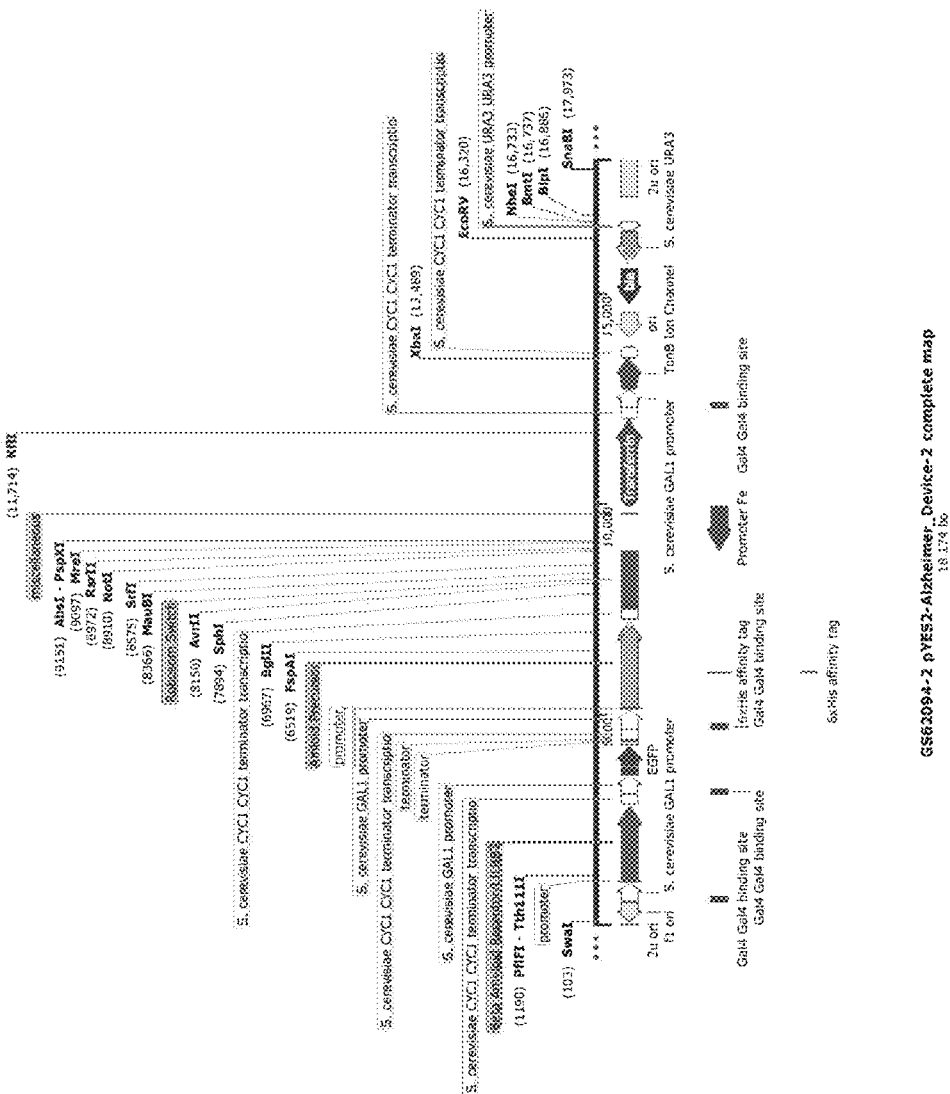
FIG. 4 shows a linear schematic of a vector described herein, wherein the vector has SEQ ID NO. 10.
Figure 5:
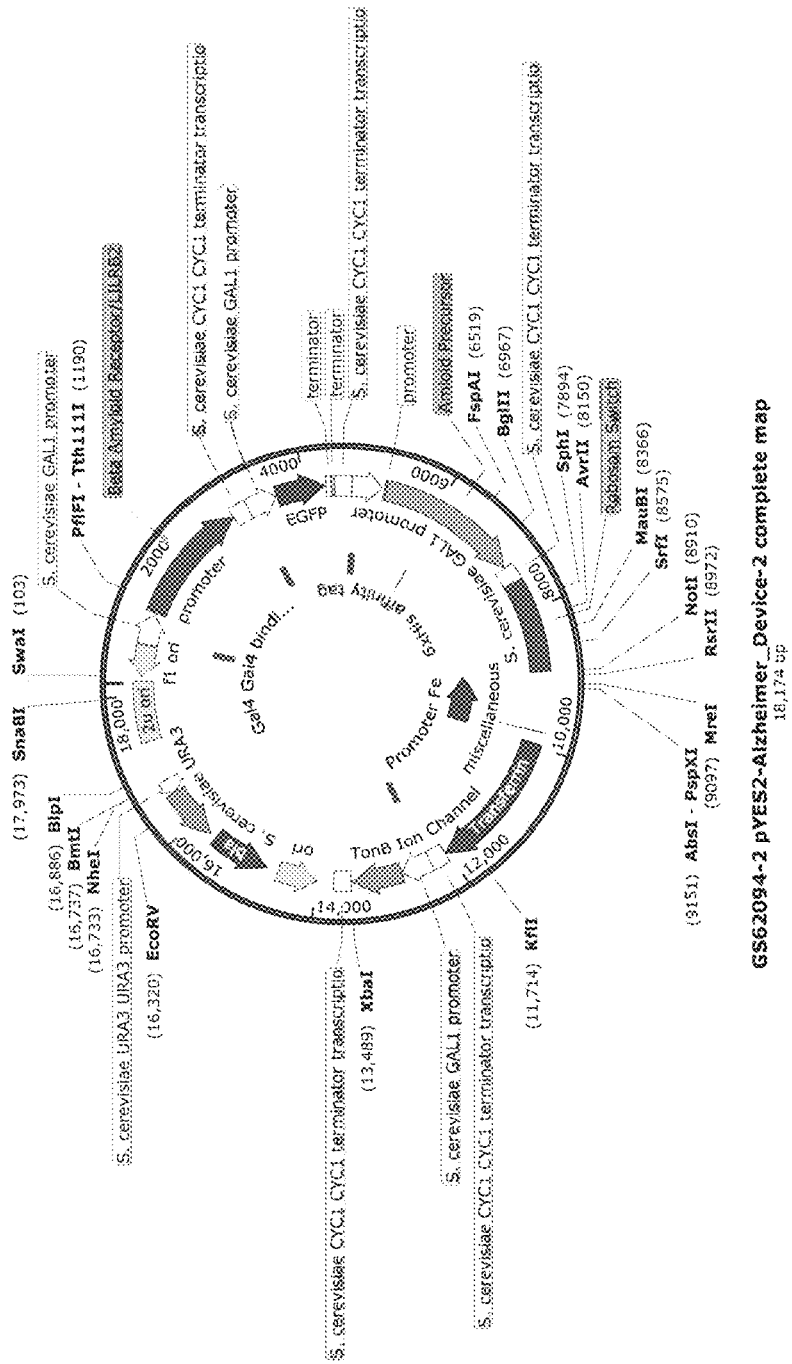
FIG. 5 shows a circular schematic of a vector described herein, wherein the vector has SEQ ID NO. 10.

A second DNA device was constructed by assembling a plasmid (pBSKII and pYES2 were both successfully tested) having the following genetic components in the following order: (a) a gene that expresses β-amyloid receptor having SEQ ID NO. 8, (b) a gene that expresses a green fluorescent reporter protein having SEQ ID NO. 9, (c) a gene that expresses an amyloid precursor protein having SEQ ID NO. 3, (d) a gene that expresses a riboswitch having SEQ ID NO. 2, (e) an iron promoter having SEQ ID NO. 4, (f) a gene that expresses transferrin having SEQ ID NO. 5, and (k) a gene that expresses TonB having SEQ ID NO. 6. One sample DNA device has SEQ ID NO. 10 and is shown in FIGS. 4 and 5.

Figure 11:
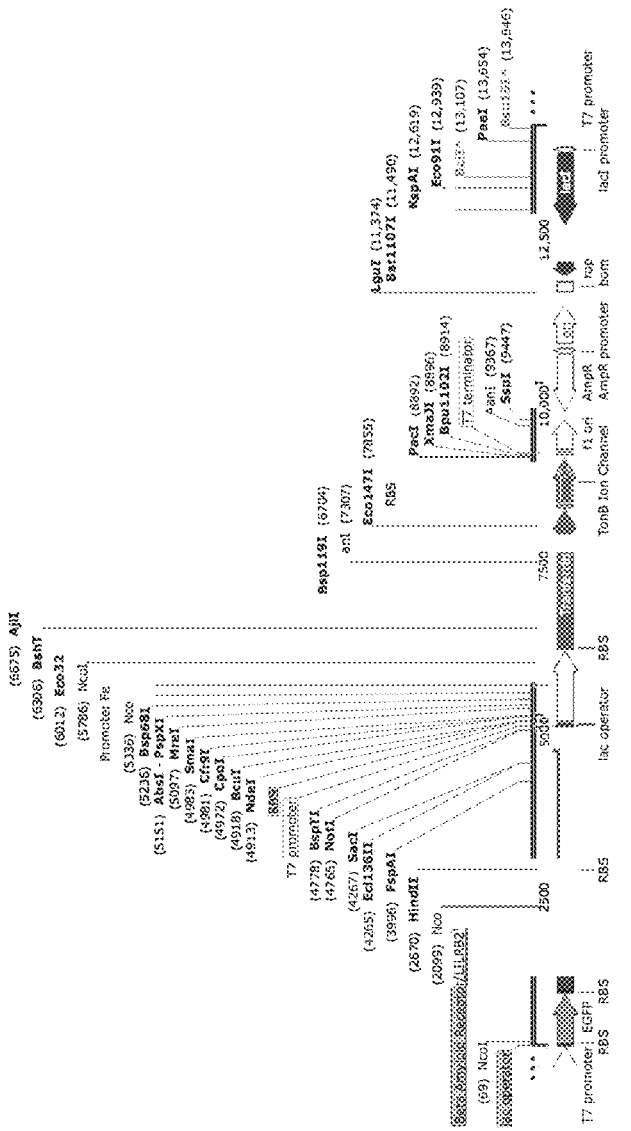
FIG. 11 shows a linear schematic of a vector described herein, wherein the vector has SEQ ID NO. 11.
Figure 12:
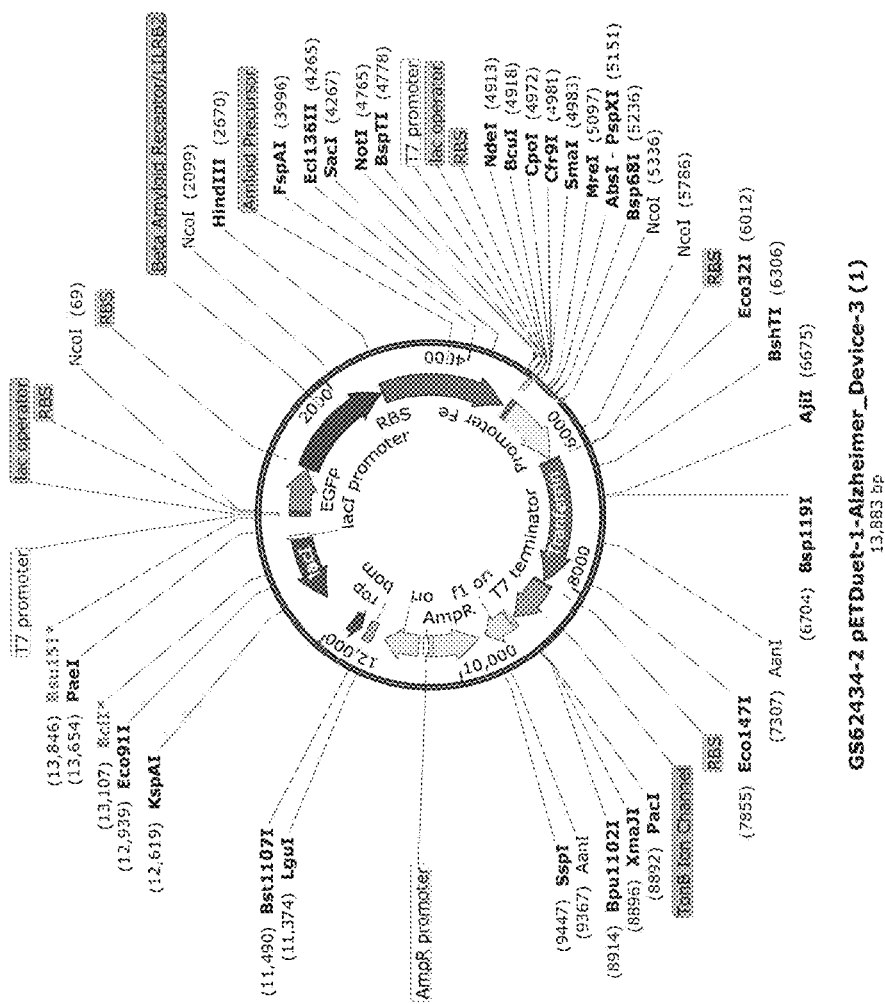
FIG. 12 shows a circular schematic of a vector described herein, wherein the vector has SEQ ID NO. 11.
Figure 15A:
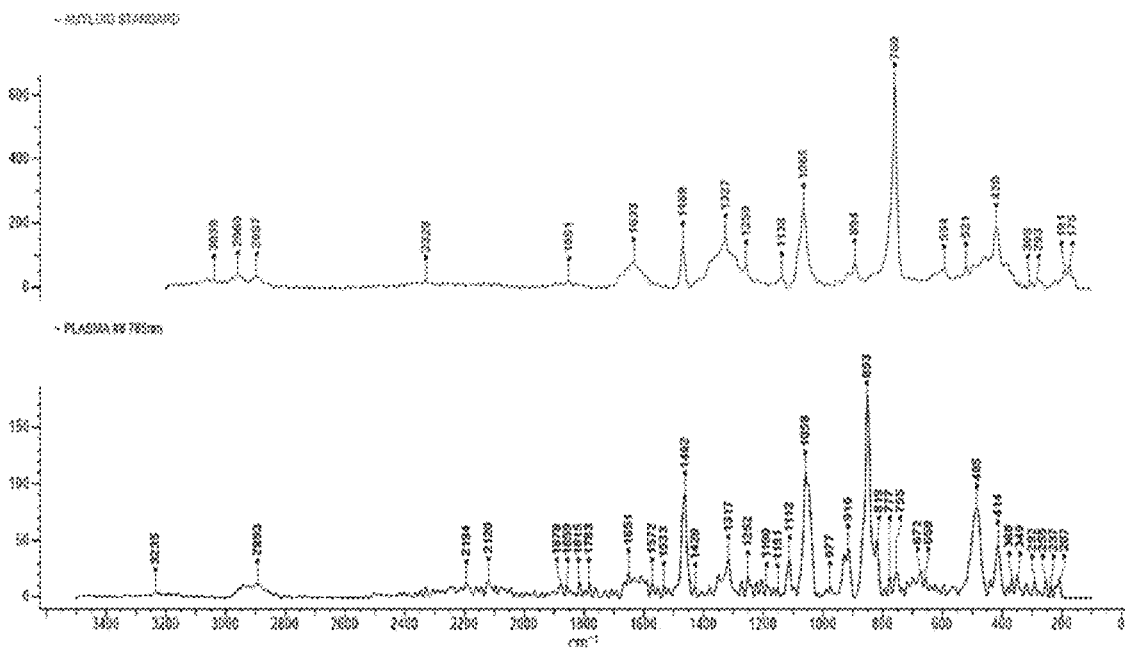
FIGS. 15A-C show the Raman spectroscopy analysis of samples. This figure illustrates the results of the Raman spectroscopy analysis for samples from different patient groups based on the plasma plus DNA amyloid sensor as compared to the standard amyloid protein.
Figure 15B:
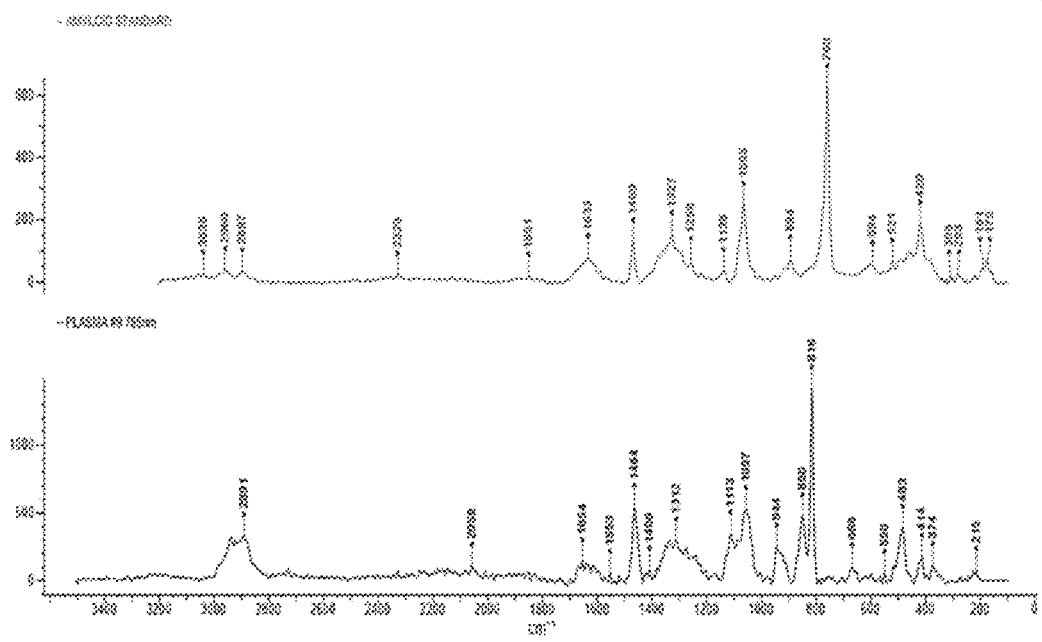
Figure 15C:
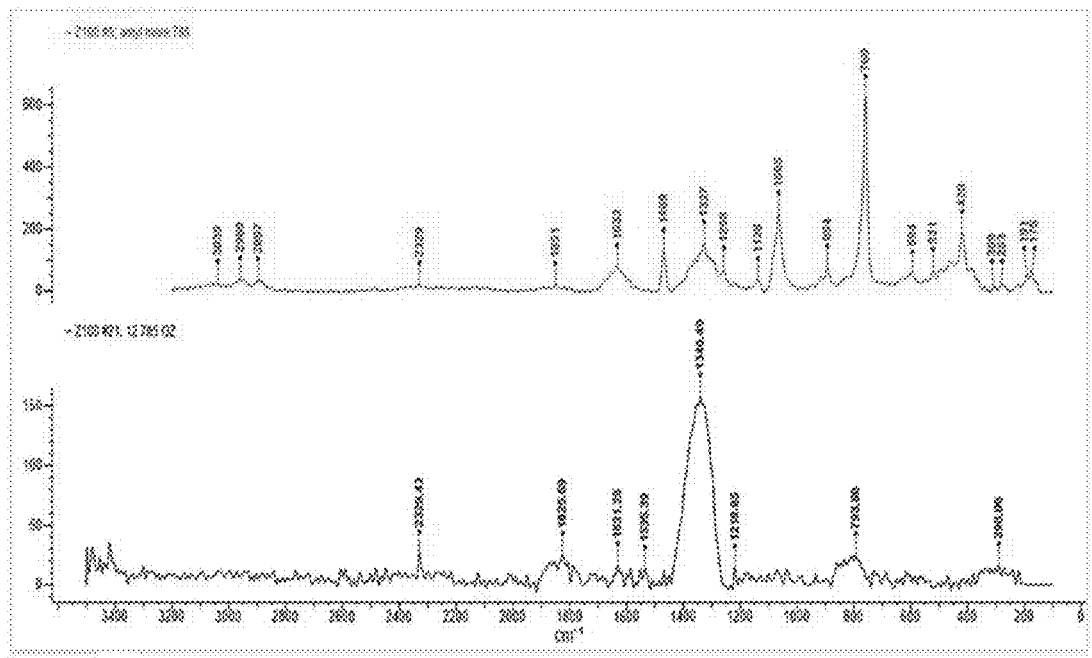

A third DNA device was constructed by assembling a plasmid (pETDuet-1 was successfully tested) having the following genetic components in the following order: (a) a gene that expresses a green fluorescent reporter protein having SEQ ID NO. 9, (b) a gene that expresses β-amyloid receptor having SEQ ID NO. 8, (c) a gene that expresses an amyloid precursor protein having SEQ ID NO. 4, (d) an iron promoter having SEQ ID NO. 4, (e) a gene that expresses transferrin having SEQ ID NO. 5, and (f) a gene that expresses TonB having SEQ ID NO. 6. One sample DNA device has SEQ ID NO. 11 and is shown in FIGS. 11 and 12.

A fourth DNA device was constructed by assembling a plasmid (pBSKII was successfully tested) having the following genetic components in the following order: (a) a T7 promoter, (b) a gene that expresses an amyloid precursor protein having SEQ ID NO. 4, (c) a gene that expresses a riboswitch having SEQ ID NO. 2, (d) a gene that expresses TonB having SEQ ID NO. 6, and (e) a gene that expresses a yellow fluorescent reporter protein having SEQ ID NO. 1.

The amount of fluorescence from the reporter protein correlated to protein production in media for all constructs.

Host Cell Purification and Transformation

Some biological devices were constructed using yeast (*S. cerevisiae*) cells with a pYES2 plasmid vector. After the vector comprising the DNA construct has been produced, the resulting vector can be incorporated into the host cells using methods known in the art (e.g., Gietz, R. D. and R. H. Schiestl, 2007, *Nature Protocols*, "Quick and easy yeast transformation using the LiAc/SS carrier and DNA/PEG method," Vol. 2, 35-37).

Other biological devices were constructed using bacteria (*E. coli*) cells with a pBSKII plasmid vector. Top10 chemically competent *E. coli* cells from Life Technologies were transformed with the DNA construct described herein using a modified version of a protocol provided by the supplier. 254, of cells were mixed with 5 μL of the DNA construct. Cells were placed on ice for 20 min. Cells were then subjected to heat shock for 50 seconds at 42° C. After heat shock, cells were once again incubated on ice for 2 min. 250 μL of SOC medium (2% w/v tryptone, 0.5% w/v yeast extract, 8.56 mM NaCl, 2.5 mM KCl, 10 mM $MgCl_2$, 10 mM $MgSO_4$, 20 mM glucose) were added to the mixture of cells and inserts. The samples were placed in an electromagnetic chamber and subjected to a minicurrent (900 mA) that created a magnetic field of 0.35 Gauss for 15 minutes. After electromagnetic exposure, 100 μL aliquots were plated in petri dishes with SOB agar (same as SOC but without the glucose), ampicillin, isopropyl β-D-1-thiogalactopyranoside (IPTG), and 5-bromo-4-chloro-3-indolyl-β-D-galactopyranoside (X-gal). Petri dishes were then incubated for 18 hours.

Alternatively, the pETDuet-1 plasmid-based device was transformed into DH5α and BL21(DE3) *E. coli* using a standard heat shock protocol. Four clones were selected from a transformed plate and processed for full-length DNA sequencing. A clone with 100% DNA sequence accuracy was selected for further processing and was used to obtain a high concentration of plasmid construct at a mid-scale plasmid purification level.

DNA expression and effectiveness of transformation were determined by fluorescence of the transformed cells expressed in fluorescence units (FSUs), according to a protocol provided by the manufacturer, using a 20/20 Luminometer (Promega). The blue fluorescence module (with a 450 nm excitation wavelength and a 600 nm emission wavelength) was used to evaluate the effectiveness of transformation. When no fluorescent reporter protein was assembled, no fluorescence was observed. Plasmid DNA extraction purification, PCR, and gel electrophoresis were also used to confirm transformation.

Protein Expression in Metal-Containing Media

The development of β-amyloid in the presence of metals was assessed. Transformed cells containing the DNA construct described herein were plated on 250 µL of agar with suitable media containing either 1 mM or 2 mM of iron metal, iron sulfate, copper chloride, or copper sulfate (i.e., 8 separate experiments). A positive control consisting of transformed cells that did not include a gene for the amyloid precursor protein was also assessed. Bacterial populations were assessed by counting colony forming units (CFUs). Results are presented in Table 5.

TABLE 5

CFU Count for Cells with and without DNA Construct Grown in Metal-Containing Media

| Metal (1 mM) | With DNA Construct | Without DNA Construct |
|---|---|---|
| Iron | $55 \times 10^6$ | $50 \times 10^6$ |
| Iron sulfate | $70 \times 10^6$ | $70 \times 10^6$ |
| Copper sulfate | $59 \times 10^6$ | $35 \times 10^6$ |
| Copper chloride | $84 \times 10^6$ | $47 \times 10^6$ |
| None | $29 \times 10^6$ | $23 \times 10^6$ |

Thus, cells transformed with a DNA construct as described herein are better able to survive in media containing metal ions.

Production and Quantification of β-Amyloid by ELISA

The Alpha Diagnostic β-Amyloid 1-42 ELISA kit was used to quantify protein production. The following procedure was employed:

1. Top10 Chemically Competent *E. coli* cells transformed with the construct depicted in FIGS. 2 and 3 were inoculated in LB+ampicillin liquid medium and incubated at 37° C. for 7 hours. Growth of the cells was determined based on absorbance ($OD_{550-600}$) using a spectrophotometer.
2. 10 mL samples of cells were mixed with 150 mL of fresh LB+ampicillin medium. In some experiments, 10 mL samples of cells were mixed with 50 mL of fresh LB+ampicillin medium.
3. Cell cultures were incubated at 37° C. for 4 hours.
4. After incubation, 100 µL of IPTG were added to each sample.
5. Cell growth was determined by measuring absorbance at 550-600 nm and comparing to a standard calibration curve.
6. Each culture was centrifuged at 5000 rpm for 15 minutes at room temperature to obtain a pellet.
7. The pellets were resuspended in 100 mL of lysis buffer (from the Open Biotechnology Protein Extraction Kit) for each 1 L of the original culture.
8. The pellets were mixed into homogeneous suspension while avoiding bubble formation.
9. 1 mL of lysozyme per 1 L of culture was added and the samples were vortexed.
10. The lysed cells were stored at −20° C. until needed.
11. Cell suspensions were thawed in a water bath at 37° C. This activates the lysozyme and clearness or viscosity indicated lysis of the cells.
12. 1 mL of $CaCl_2$ was added to each sample.
13. 1 mL of DNase was added to each sample.
14. The samples were mixed well and incubated at 37° C. for 5 minutes or until clear or until solution viscosity decreased. The extractants were left in a refrigerator at 4° C. until needed.

Figure 6:
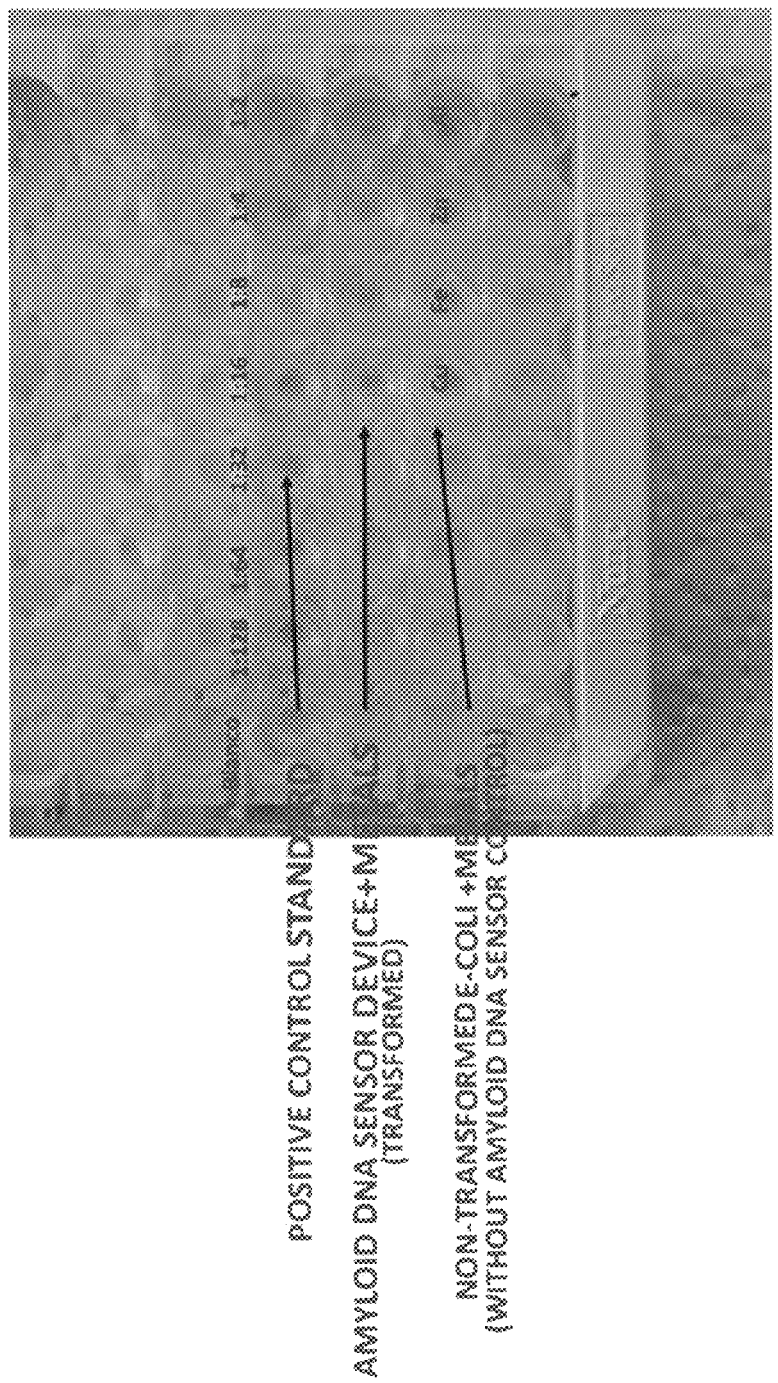
FIG. 6 shows an ELISA assay for β-amyloid protein in transformed E. coli cells containing a vector as described herein grown in the presence of different metal ions ($Cu^{2+}$, $Fe^{2+}$, $Zn^{2+}$, and $Al^{2+}$) as compared to a control (non-transformed E. coli). A darker yellow color indicates a higher concentration of β-amyloid protein, whereas a non-transformed control does not show any yellow color (third row of wells). Cells transformed with the vector and grown in the presence of metals showed the most intensity (second row of wells). The top row of wells shows dilutions of β-amyloid as a positive control.

Qualitative results can be seen in FIG. 6. Higher volumes of the device resulted in greater β-amyloid production, as expected. When the β-amyloid vector was incorporated into cells and those cells were grown in the presence of metal ions, more β-amyloid was produced.

Determination of β-Amyloid Protein in Patient Blood Samples by Western Blot

β-amyloid protein was identified in patients using a previously-published method. Protein was quantified in two human plasma samples and the volume was adjusted to yield 2 mg/mL protein in each sample, with an equal volume of buffer used as a control. Equal amounts of protein in two sets of samples at 15 µg/mL and 30 µg/mL in Laemmle sample buffer were heated in a water bath for 7 minutes and thereafter electrophoresed on 8-16% gradient SDS-polyacrylamide gel.

Figure 7:
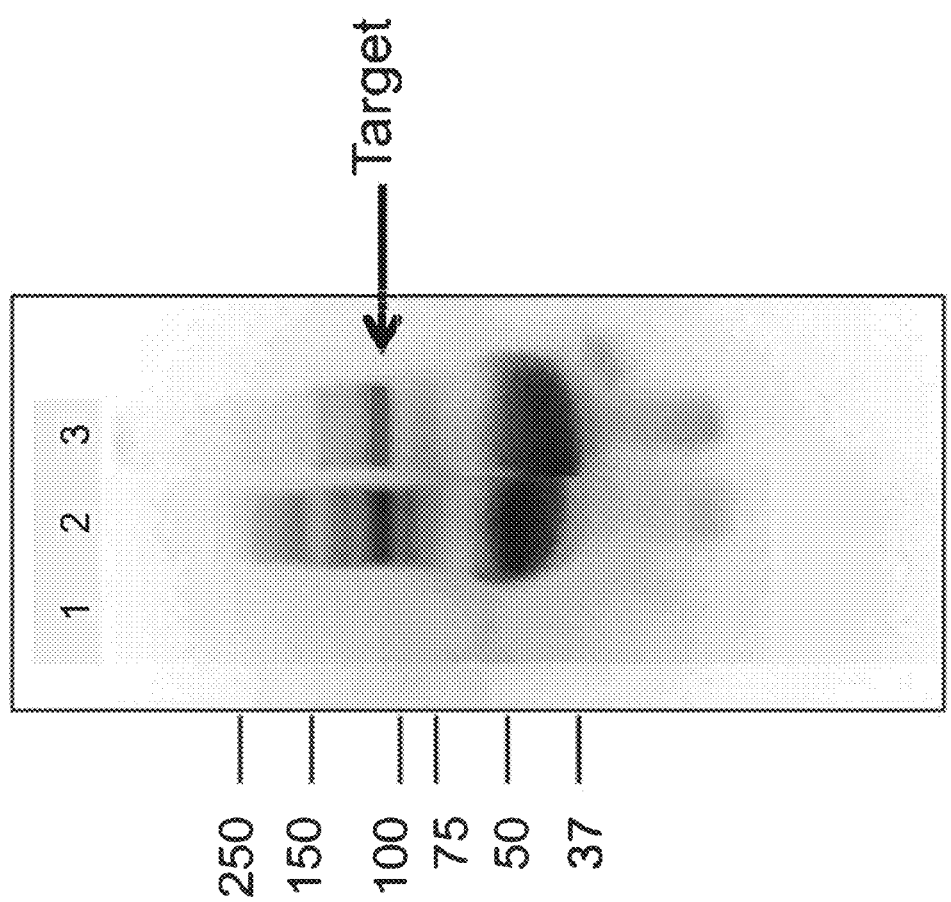
FIG. 7 shows a representative Western Blot test for β-amyloid protein in a patient's blood plasma. Lane 1 is a control performed on only buffer. Lane 2 represents a plasma sample from a patient with a high level of β-amyloid fluorescence and clinical Alzheimer's symptoms. Lane 3 represents a plasma sample from a patient with a low level of β-amyloid fluorescence and no clinical Alzheimer's symptoms.

Proteins were transferred to a polyvinylidene difluoride (PVDF) membrane and subjected to blotting including an anti-mouse β-amyloid monoclonal antibody (AMY-33). The blotted membrane was subjected to a series of washing steps in TBST buffer. The antigen-antibody complexes were visualized using enhanced chemiluminescence (ECL-2, Thermo Scientific). Results from the 30 mg/mL samples can be seen in FIG. 7. A clinically-diagnosed Alzheimer's patient showed a higher concentration of β-amyloid than a healthy patient, as expected.

In Vivo Fluorescence Determination of β-Amyloid in Blood Plasma Samples from Patients Fluorescence of the β-amyloid sensor was measured in a GloMax Bioanalyzer Detector with Instinct Software (Promega) set at a wavelength range of 400-550 nM using ultraviolet light as a source of excitation. Fluorescence was correlated to the concentration of β-amyloid in blood plasma samples from patients and compared to the criteria of medical diagnosis for Alzheimer's disease.

Alzheimer's patients were divided into three groups (1=having an Alzheimer's diagnosis, 2=pre-Alzheimer's, and 3=normal or healthy). Blood plasma samples were categorized from the three different groups of patients according to their ranges of fluorescence and medical diagnosis.

Samples from 20 patients were analyzed (7 for Alzheimer's patients, 6 samples for pre-Alzheimer's subjects, and 7 for normal/healthy subjects). Each sample was mixed with the bacterial DNA β-amyloid device (sensor) and vortexed for 30-50 seconds. A total sample volume of 240 µL was used in a ratio of 2:1 (160 µL bacterial DNA β-amyloid sensor: 80 µL blood plasma sample) for fluorescence detection of β-amyloid. The natural inherent fluorescence of the bacterial DNA β-amyloid device (1700 FSU) was subtracted from the final fluorescence in each sample. The results were then divided into three groups according to the intensity of the fluorescence in relation to medical diagnosis of the patients. Group 1 patients had 3301-7000 or greater FSU and exhibited memory loss, mental confusion, and disorientation. Group 2 patients had 1501-3300 FSU and exhibited memory loss and/or mental confusion. Group 3 had 0-1500 FSU and did not show any clinical signs of Alzheimer's disease.

CT Scan Analysis

Figure 8:
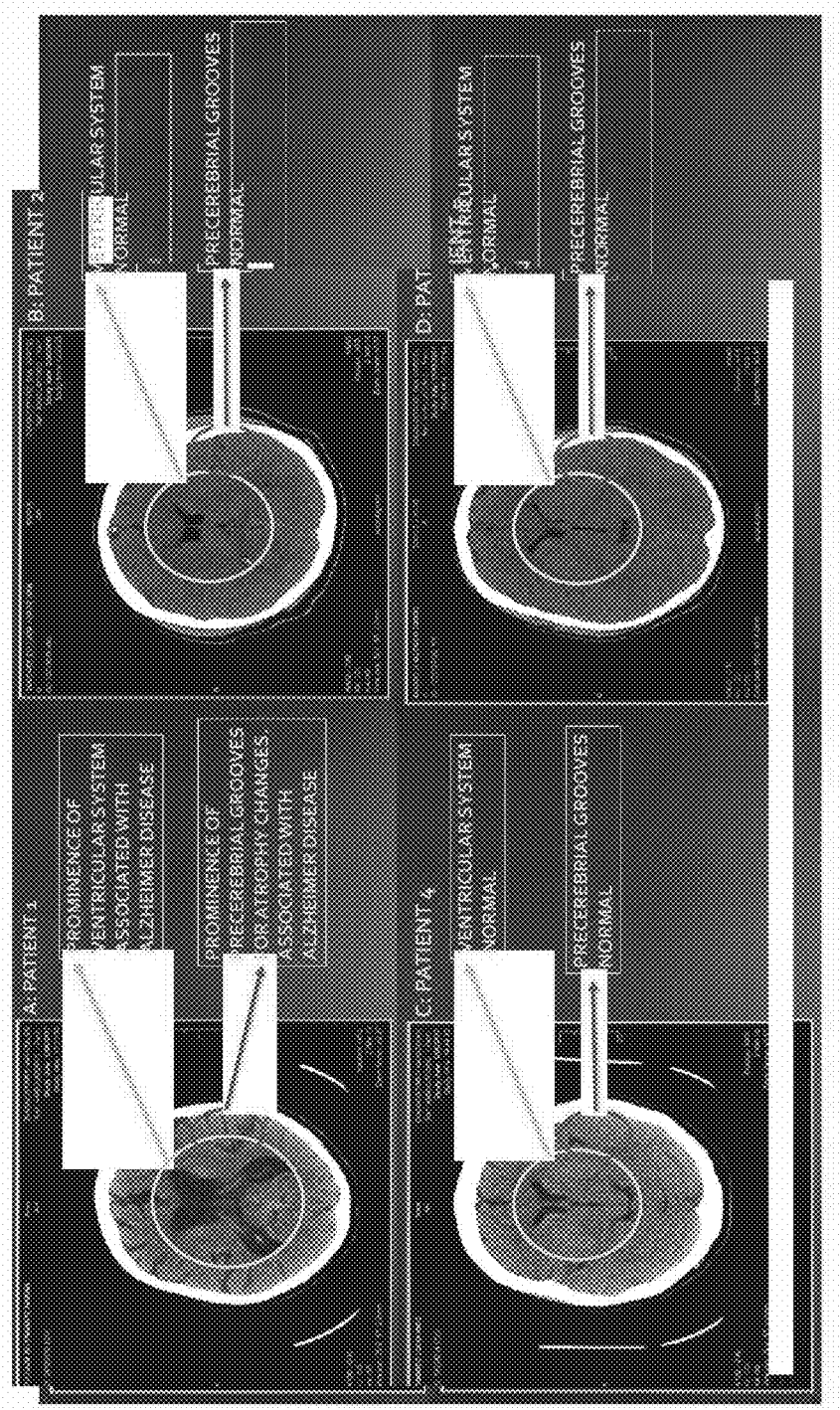
FIG. 8 shows comparative CT scan results from patients clinically diagnosed with Alzheimer's versus healthy patients. Image A (top left) shows prominent expression of symptoms in a patient clinically diagnosed with Alzheimer's and correlates to high fluorescence results for the same patient. Images B (top right), C (lower left) and D (lower right) show patients of different genders and ages with no tomographical symptoms of Alzheimer's. Images B and D correlate with low fluorescence results corresponding to normal/healthy patients, whereas Image C exhibits a slight atrophy and a mid-level of fluorescence, placing this patient in the pre-Alzheimer's group.

CT scans of experimental subjects were performed at the Diagnostimed Center in Manizales, Colombia. The analysis was carried out using axial cross-sectional images, using a helical computed tomography scan on equipment from General Electric. The scan was performed in a linear orbitometal position from the cranial base to the cerebellar tentorium with cross-sections each 5 and or 10 mm up to the vertex (i.e., soft tissue). CT scan results are presented in FIG. 8.

MRI Analysis

Figure 9:
FIG. 9 shows comparative MRI results from patients clinically diagnosed with Alzheimer's versus healthy patients. Image A (top left) shows diminishing frontal and parietal lobes, which were not evident in the CT scan. Images B (top right) and C (bottom) do not exhibit Alzheimer's symptoms in the MRI results, corresponding to a normal/healthy diagnosis. In all instances, MRI results correlate with observed fluorescence intensity.

Magnetic Resonance Imaging was performed at the Diagnostimed Center in Manizales, Colombia. Analysis was carried out using radiofrequency pulse types spin echo and turbo spin echo with a 1.5 Tesla magnet using equipment from General Electric. Imaging was created based on anatomic differentiation (i.e., T1 and T2) using three-dimensional phase contrast. MRI results are presented in FIG. 9.

Comparative Results

The presence of β-amyloid protein was measured in vivo in human blood plasma samples using *E. coli* biological devices transformed with a pBSKII plasmid having, from 5' to 3', a T7 promoter, a gene that expresses amyloid precursor protein, a riboswitch, a gene that expresses TonB, and a gene that expresses a yellow reporter protein. A direct correlation was seen between higher fluorescence of β-amyloid and clinical medical reports based on criteria of memory loss, disorientation, and mental confusion. This correlation was strongest in the group of patients with the highest levels of β-amyloid fluorescence (i.e., Group 1). Samples from women showed the highest levels of β-amyloid fluorescence and especially in older women (ages 70 and up), the β-amyloid fluorescence correlated (55.5%) with clinical medical diagnosis of Alzheimer's disease. Plasma samples from men of the same age showed lower β-amyloid fluorescence and lower correlation with clinical medical diagnosis. These results showed correlation only for groups 1 and 3 (as based on clinical criteria) with either higher β-amyloid expression with correlation with all three clinical criteria or without correlation to any of them.

For group 2, there was a high correlation of β-amyloid fluorescence (87.5%) with the clinical diagnosis of pre-Alzheimer's based on either one or two clinical criteria (i.e., memory loss, disorientation, or mental confusion).

Individuals with no Alzheimer's or pre-Alzheimer's diagnosis (i.e., group 3) showed the lowest level of β-amyloid fluorescence of any group. Correlations of clinical diagnosis and β-amyloid fluorescence from the DNA sensors are presented in Table 6. Glycemia levels for patients in each group were also measured and are presented in Table 6.

TABLE 6

Correlation of β-Amyloid Fluorescence and Medical Diagnosis

| Patient ID | Sex | Age | β-Amyloid Fluorescence | Diagnosis | Glycemia (mg/dL) |
|---|---|---|---|---|---|
| Group 1: Alzheimer's Diagnosis | | | | | |
| 1 | F | 78 | 4000 | Memory loss, disorientation, mental confusion | Not tested |
| 2 | F | 86 | 5000 | Memory loss, initial disorientation, mental confusion | 93 |
| 3 | M | 85 | 5000 | Memory loss, initial disorientation, mental confusion | 150 |
| 4 | F | 88 | 5000 | Memory loss, pronounced disorientation, mental confusion | 180 |
| 5 | F | 72 | 5000 | Memory loss, initial disorientation, mental confusion | 115 |
| 6 | F | 85 | 5000 | Memory loss, disorientation, mental confusion | 140 |
| 7 | F | 75 | 7000 | Memory loss, pronounced disorientation, mental confusion | 170 |
| Group 2: Pre-Alzheimer's Patients | | | | | |
| 8 | M | 70 | 2000 | Mental confusion | 120 |
| 9 | F | 77 | 2000 | Mental confusion | 106 |
| 10 | F | 63 | 2250 | Memory loss, mental confusion | 74 |
| 11 | F | 84 | 2700 | Memory loss, mental confusion | 98 |
| 12 | M | 80 | 3000 | Memory loss, mental confusion | 145 |
| 13 | F | 63 | 3300 | Memory loss, mental confusion | 136 |
| Group 3: Normal/Healthy | | | | | |
| 14 | M | 23 | 900 | Healthy | 127 |
| 15 | M | 28 | 900 | Healthy | 116 |
| 16 | F | 18 | 1000 | Healthy | 102 |
| 17 | F | 61 | 1000 | Healthy | Not tested |
| 18 | F | 56 | 1000 | Healthy | Not tested |
| 19 | M | 34 | 1000 | Healthy | 100 |
| 20 | F | 56 | 1500 | Healthy | 90 |

DNA β-amyloid sensor results were compared to CT scan, MII, and medical diagnosis for selected patients, thus confirming the efficacy of the sensor for detecting β-amyloid protein in patient blood plasma samples. It was found that fluorescence results were more accurate and more distinctively related to the patient's disease status compared to CT scans, which are most accurate for patients who already have an Alzheimer's diagnosis, or to MM, which is more general and/or less specific for targeting Alzheimer's-related damages. Comparative results from the β-amyloid sensor, clinical medical symptoms, CT can, and MM are presented in Table 7 along with glycemia levels for selected patients.

TABLE 7

Comparative Results for DNA β-Amyloid Sensor, Medical Diagnosis, CT Scan, and MRI

| Patient | Sex | Age | β-Amyloid Fluorescence | Clinical Symptoms | MRI | CT Scan | Glycemia (mg/dL) |
|---|---|---|---|---|---|---|---|
| 1 | F | 85 | 5000 ± 200 | Memory loss, disorientation, mental confusion | N/A | Prominence of pericerebral grooves for atrophy changes. Prominence of ventricular system. | 140 |
| 2 | M | 34 | 1000 ± 150 | None | Normal volume between gray and white substance, cerebrum and brain in normal aspect. No evidence of intra- and extra-axial injuries. Ventricular system without dilatation | No signs of Alzheimer's found. | 100 |
| 3 | F | 82 | 1700 ± 50 | Memory loss, initial disorientation, anxiety | N/A | Bilateral frontal atrophy. Ventricular system slightly expanded. | N/A |
| 4 | F | 61 | 1600 ± 50 | None | Cerebrum and brain in normal aspect. Slight atrophy in bilateral frontoparietal. sphenoid sinusitis. No evidence of intra- and extra-axial injuries. Non-specific leukoencephalopathy. | No signs of Alzheimer's found. | N/A |
| 5 | M | 29 | 900 ± 0 | None | Normal volume between gray and white substance. Cerebellum and brain in normal aspect. No evidence of intra- and extra-axial injuries. Ventricular system without dilatation. | No signs of Alzheimer's found. | 117 |
| 6 | F | 92 | 2800 ± 0 | Memory loss, mental confusion | N/A | Prominence of pericerebral grooves for atrophy changes. Supratentorial ventricular system expanded. | N/A |

β-Amyloid Fluorescence using Intact Yeast Devices

Devices were prepared using yeasts (*S. cerevisiae*) carrying pYES2 plasmids (FIGS. 2 and 3). These devices were used to determine β-amyloid fluorescence in a manner similar to what was described above with bacteria. Results from DNA sensor composed of intact yeast cells confirmed that sensors may be constructed using eukaryotic cells, and are presented in Table 8.

TABLE 8

β-Amyloid Fluorescence using Intact Yeast Cells

| Patient | Sex | Age | β-Amyloid Fluorescence | Medical Diagnosis |
|---|---|---|---|---|
| Group 1: Alzheimer's Patients | | | | |
| 1 | F | 50 | 4350 | Memory loss, mental confusion |
| 2 | F | 82 | 4400 | Memory loss, mental confusion |
| 3 | F | 66 | 5600 | Memory loss, mental confusion |
| 4 | F | 75 | 9800 | Memory loss, mental confusion |
| Group 2: Pre-Alzheimer's Subjects | | | | |
| 5 | F | 85 | 2400 | Memory loss |
| 6 | F | 92 | 2800 | Memory loss, mental confusion |
| Group 3: Normal/Healthy Subjects | | | | |
| 7 | M | 43 | 1900 | Healthy |
| 8 | M | 29 | 1000 | Healthy |
| 9 | M | 40 | 1100 | Healthy |
| 10 | F | 57 | 1200 | Healthy |

β-Amyloid Fluorescence using Yeast Extracts

Devices were prepared using yeasts (*S. cerevisiae*) carrying pYES2 plasmids (FIGS. 2 and 3). Cells were lysed and extracts were collected. These extracts were used to determine β-amyloid fluorescence in a manner similar to what was described above with intact cells. Results from DNA sensor composed of yeast extracts confirmed that whole cells do not need to be present for the sensor to work, and are presented in Table 9.

TABLE 9

β-Amyloid Fluorescence using Cell Extracts

| Patient | Sex | Age | β-Amyloid Fluorescence | Medical Diagnosis |
|---|---|---|---|---|
| Group 1: Alzheimer's Patients | | | | |
| 1 | M | 86 | 4200 | Memory loss, mental confusion, disorientation |
| Group 2: Pre-Alzheimer's Subjects | | | | |
| 2 | F | 82 | 2100 | Memory loss |
| Group 3: Normal/Healthy Subjects | | | | |
| 3 | F | 61 | 1300 | Healthy |
| 4 | M | 40 | 1100 | Healthy |
| 5 | M | 29 | 1000 | Healthy |

Due to the success of this initial test, a further series of experiments were conducted using the yeast extracts, but with samples from a larger set of patients. In some instances, a lyophilized yeast extract was used. These results are presented in Table 10, with patients tested using a lyophilized extract being marked by an asterisk; samples have been background corrected to account for the level of fluorescence produced by a control containing buffer and water but no patient sample. Glycemia values were also measured for the subjects but did not correlate to the presence of β-amyloid or the diagnosis of Alzheimer's or pre-Alzheimer's.

TABLE 10

β-Amyloid Fluorescence using Cell Extracts

| Patient ID | Gender | Age | β-Amyloid Fluorescence | Medical Diagnosis | Glycemia (mg/dL) |
|---|---|---|---|---|---|
| Group 1: Alzheimer's Diagnosis | | | | | |
| 11 | F | 77 | 11000 | Cognitive impairment (disorientation, mental confusion) and memory loss | 84 |
| 3 | M | 76 | 13000 | Cognitive impairment (disorientation, mental confusion) | 87 |
| 9 | F | 72 | 13000 | Cognitive impairment (disorientation, mental confusion) and memory loss | 91 |
| 8 | F | 89 | 13300 | Cognitive impairment (disorientation, mental confusion) and memory loss | 86 |
| 10 | M | 67 | 15000 | Cognitive impairment (disorientation, mental confusion) and memory loss | 87 |
| 4* | F | 78 | 15700 | Not determined | 88 |
| 2 | F | 77 | 15800 | Cognitive impairment (disorientation, mental confusion) | 87 |
| 6 | F | 86 | 16300 | Cognitive impairment (disorientation, mental confusion) and memory loss | 89 |
| Group 2: Pre-Alzheimer's | | | | | |
| 32 | F | 62 | 9000 | Cognitive impairment | 85 |
| 17 | M | 47 | 9000 | Not determined | 77 |
| 16 | F | 50 | 9300 | Cognitive impairment | 73 |
| 13* | M | 57 | 9600 | Not determined | 81 |
| 1* | F | 61 | 10000 | Not determined | 97 |
| 7* | F | 78 | 10700 | Memory loss | 82 |
| 5 | F | 75 | 11000 | Cognitive impairment | 75 |
| Group 3: Healthy/Normal | | | | | |
| 24 | M | 22 | 6800 | Healthy | 90 |
| 30* | F | 27 | 6900 | Healthy | 82 |
| 20* | F | 29 | 7100 | Healthy | 67 |
| 23* | F | 22 | 7300 | Healthy | 76 |
| 31 | M | 50 | 7300 | Healthy | 172 |
| 15 | F | 56 | 7400 | Healthy | 97 |
| 22 | F | 25 | 7500 | Healthy | 94 |
| 29* | M | 28 | 7500 | Healthy | 82 |
| 21 | M | 29 | 7600 | Healthy | 68 |
| 19 | F | 32 | 7700 | Healthy | 64 |
| 18* | F | 35 | 7800 | Healthy | 65 |
| 27 | F | 23 | 7800 | Healthy | 88 |
| 26 | F | 28 | 8100 | Healthy | 93 |
| 28 | F | 29 | 8800 | Healthy | 90 |
| 14 | F | 41 | 8900 | Healthy | 72 |
| 25 | F | 21 | 9000 | Healthy | 81 |

Additional testing including CT scans and magnetic resonance imaging were performed on selected patients. Results are presented in Table 11. Matching patient ID numbers in Tables 10 and 11 represent the same respective patients.

TABLE 11

Additional Imaging to Verify Fluorescence Results

| Patient ID | Gender | Age | Medical Diagnosis | CT Scan | MRI |
|---|---|---|---|---|---|
| 2 | F | 77 | Cognitive impairment (disorientation, mental confusion) | Dilation of the ventricular system | Sulci widening, dilation of the ventricular system, hippocampal atrophy |
| 6 | F | 86 | Cognitive impairment (disorientation, mental confusion) and memory loss | Prominence of ventricular system and sulci widening | Sulci widening, dilation of the ventricular system, hippocampal atrophy |

TABLE 11-continued

Additional Imaging to Verify Fluorescence Results

| Patient ID | Gender | Age | Medical Diagnosis | CT Scan | MRI |
|---|---|---|---|---|---|
| 5 | F | 75 | Not determined | Sulci widening | Sulci widening, hippocampal atrophy |
| 7 | F | 78 | Memory loss | Not determined | Sulci widening |
| 23 | F | 22 | Healthy | Without alteration | Without cerebral alterations |
| 24 | M | 28 | Healthy | Without alteration | No signs of Alziheimer's disease |

Use of Fluorescent Dye with Yeast Extract

Blood plasma and spinal fluid were taken from the following groups (three subjects per group)s:
1. clinically diagnosed Alzheimer's patient (70 years old or older)
2. patients not clinically not diagnosed with Alzheimer's but with relatives diagnosed with Alzheimer's (50-60 years old)
3. healthy patients (younger than 30 years old)

To each patient sample, a solution of the yeast extract produce from the device in FIGS. 4-5 (3:1 volume ratio of extract to sample). To 90 µL of sample with extract, sulfo-cyanine Cy3 NHS ester was added per the instructions in the Lumiprobe kit. Subsequent purification was also performed per the instructions of the Lumiprobe kit. Fluorescence was measured in a GloMax Bioanalyzer Detector with Instinct Software (Promega) set at a wavelength range of 400-550 nM using ultraviolet light as a source of excitation. The results are provided in Table 10 below. The results show that health subjects had lower fluorescent readings when compared to subjects with a family history of Alzheimer's and patients with Alzheimer's.

TABLE 10

| Sample | Fluorescence (FSU) Blue/490(510-570) |
|---|---|
| Dye Cy3 | 856 |
| Amyloid Protein (0.01 mg/mL) | 1391 |
| Amyloid Protein (0.01 mg/mL) + Dye Cy3 | 5098 |
| Extract Device | 1.10E+04 |
| Extract Device + Cy3 | 2.30E+04 |
| Plasma Healthy Patient | 2.30E+03 |
| Plasma Patient diagnosed with Alzheimer | 9.00E+03 |
| Plasma Healthy Patient + Cy3 | 4.20E+03 |
| Plasma Patient diagnosed with Alzheimer + Cy3 | 9.40E+03 |
| Spinal fluid (SF) Patient with family history of Alzheimers | 895 |
| Spinal fluid (SF) Patient diagnosed with Alzheimer | 983 |
| Spinal fluid (SF) Patient with family history of Alzheimers + Cy3 | 1.85E+05 |
| Spinal fluid (SF) Patient diagnosed with Alzheimer + Cy3 | 5.72E+05 |
| Plasma Healthy Patient + Extract Device | 1.10E+04 |
| Plasma Healthy Patient + Extract Device + Cy3 | 1.10E+05 |
| Plasma Patient diagnosed with Alzheimer + Extract Device | 1.30E+04 |
| Plasma Patient diagnosed with Alzheimer + Extract Device + Cy3 | 1.30E+05 |
| Spinal Fluid (SF) Patient diagnosed with Alzheimer + Extract Device | 1.00E+04 |
| Spinal Fluid (SF) Patient diagnosed with Alzheimer + Extract Device + Cy3 | 5.40E+04 |
| Water | 491 |
| PBS | 867 |

Table 11 shows comparative fluorescent results of three healthy females (average age 28) and three females with Alzheimer's (average age 77). The healthy subjects had a lower fluorescent reading. Mill and CT results were also consistent with no evidence of Alzheimer's. Conversely, the female subjects with Alzheimer's had a higher fluorescent reading. Mill and CT results indicated the presence of Alzheimer's. Thus, the higher fluorescent reading is an indicator of Alzheimer's.

TABLE 11

| B-Amyloid Fluorescence - FSU (Plasma + Extract Device) Mean* | B-Amyloid Fluorescence - FSU (Plasma + Extract Device + Cy3) Mean* | Medical Diagnosis | MRI | CT Scan | Glycemia (mg/dl) |
|---|---|---|---|---|---|
| 1.30E+04 | 1.30E+05 | Cognitive Decline | Bilateral frontoparietal atrophy and enhacement of the ventricular system | Decrease of the hippocampus | 100 |
| 1.10E+04 | 1.10E+05 | healthy | No encephalic alteration. No enhacement of the ventricular system. | No effect on the hippocampus | 76 |

Use of Sensors to Detect Alzheimers in Patients

This investigation was carried out based on the integrative approach at the molecular and atomic level. Therefore, our aim was to develop two DNA sensors that detect Alzheimer's disease related β-amyloid protein in blood using synthetic and molecular biology. The DNA sensors were constructed in E. Coli or Saccharomyces cerviceae using genetic sequences and they were tested in terms of fluorescence expression units (FSU) when mixed with human blood plasma using a fluorescence detector. The intensity of the detection was enhanced by labeling the fluorescence targeted molecules in samples, and it was carried out through conjugation method using fluorescent dyes.

Construction of DNA Sensor

Synthesized DNA sequences from CloneTex Systems, Inc (Austin, Tex.) were assembled in pBSKII or pYES2 plasmid, employing standard experimental laboratory protocols. Both bacterial or yeast DNA sensors were constructed by site-directed cloning with specific primers as provided below. However, only the yeast DNA sensor (FIGS. 2 and 3) was used to detect β-amyloid in patient blood related to Alzheimer's. While the DNA bacterial sensor was used for in vitro determination of β-amyloid protein using ELISA method (FIGS. 11 and 12).

Preparation of DNA Construct

The DNA constructs were composed of genetic components described herein and assembled in plasmid vectors (i.e. pBSKII or pYES2). Sequences of genes and/or proteins with desired properties were identified in GenBank. The DNA constructs were made with similar gene parts having sequence sizes ranging from 747 to 1300 bp. These included different gene sequences with respective accession number: amyloid precursor protein gene (no. NM_201414.2) and a TonB gene (no. ACB93044.1). Other genetic parts were also obtained for inserting in the DNA constructs including, T7 promoter gene, iron promoter gene (no. CP015495.1), yellow fluorescent reporter protein (no. JQ394803.1), and riboswitch TC aptamer (no. D26134.1). However, the transferrin protein was added to the yeast DNA construct. These genetic parts included restriction sites for ease of insertion into plasmid.

This procedure was carried out by combining standard experimental laboratory methods of molecular and synthetic biology. Each gene was amplified by PCR with gene-specific primers with added restriction sites where needed.

Cloning of the Genetic Parts into the Bacterial or Yeast Device

The cloning of the genetic parts into the bacterial and yeast devices were performed as follows. Sequences of individual genes were amplified by PCR, using gene-specific primers. Genes were excised from plasmids following a protocol supplied by Promega (Madison, Wis.). The excised fragments were purified by agarose gel electrophoresis prior to ligation.

Ligation Process

A pBSKII or pYES2 plasmid already containing a gene for the amyloid precursor protein was then digested with HindIII restriction enzyme according to directions and using reagents provided by the enzyme's supplier (Promega, Madison, Wis.). The complete insert containing HindIII restriction sites on each end was ligated into the plasmid following protocol of Promega (Madison, Wis.). The reaction mixture was placed into an electromagnetic chamber for ligation and/or transformation and subjected to a minicurrent (900 mA) magnetic field with a strength of 0.35 Gauss. Successful construction of the insert and ligation of the insert into the plasmid were confirmed by gel electrophoresis.

Host Cell Purification and Transformation

Competent E. coli cells (One Shot, Top 10, Invitrogen) or yeast cells (INVSc1 yeast host strain, Invitrogen) were transformed with the DNA construct described herein using a modified version of a protocol provided by the supplier. A fully assembled S. cerviceae device was sub-cloned into pYES2 vector.

DNA expression and effectiveness of transformation were determined by the number of colonies present using a 20/20 Luminometer (Promega). Plasmid DNA extraction purification, PCR, and gel electrophoresis were also used to confirm transformation.

Effect of Metal Ions on β-Amyloid Protein Expression

The effect of metal ions on both growth of the DNA b-amyloid bacterial sensor and the production of the b-amyloid protein by the bacterial sensor were determined as provided below.

Determination of β-Amyloid Protein by ELISA

A culture of E. coli transformed with DNA β-amyloid device in the pBSK II was subjected to extraction of β-amyloid protein. Production of cell pellet was obtained prior to the extraction of the protein following standard procedures and protocol provided by Open Biotechnology protein extraction kit (ThermoFisher, Waltham, Mass.). Cells of the DNA bacterial device were grown in different concentrations of LB+ampicillin liquid medium at 37° C. for 7 hours and 4 hours. Cell growth was determined by absorbance at 550-600 nm. Next, grown cells were subjected to centrifugation in order to obtain final pellet, which was subjected to isolation of β-amyloid using the Open Biotechnology protein extraction kit (ThermoFisher, Waltham, Mass.). Finally, the pellet was lysed with lysozyme and the homogenized solution was subjected to different temperatures.

The Alpha Diagnostic International β-amyloid 1-42 ELISA kit (San Antonio, Tex.) was used to determine β-amyloid protein production plate and compared to different concentrations of β-amyloid standards. Different concentrations of the extracted β-amyloid protein from the DNA β-amyloid device culture grown with or without metals were determined in different wells of the ELISA. The color intensity of the sample was also used to determine the concentration of the amyloid protein; the higher the color intensity the higher the concentration of protein. FIG. 13 provides the ELISA assay for β-amyloid protein with or without metal ions.

Determination of β-Amyloid Protein in Patient Blood Samples by Western Blot

β-Amyloid protein was identified from patients by using standard method. Protein was quantified in two human plasma samples and the volume was adjusted to yield 2 mg/mL protein in each sample, where an equal volume of buffer was used as a control. Another human blood plasma sample was also analyzed; however, due to the lack of homogeneity, low volume, and lack of consistency during the initial preparation of this sample, this result is not shown herein. Equal amounts of protein in two sets of samples at 15 μg/mL and 30 μg/mL in Laemmle sample buffer were used and subsequently electrophoresed on 8-16% gradient SDS-polyacrylamide gel. The results from samples of 30 μg/mL of protein are only presented herein. The proteins were transferred to a PVDF (polyvinylidene difluoride) membrane and subjected to blotting including an anti-Mouse β-Amyloid Monoclonal Antibody (AMY-33). The blotted membrane was subjected to a series of washing steps in TBST buffer. The antigen-antibody complexes were visualized using enhanced chemiluminescence (ECL-2, Thermo Scientific, Rockford, Calif.). FIG. 14 provides the Western Blot test for β-amyloid protein from patient's blood plasma. Similar Western Blot analysis was carried out for extract of DNA amyloid yeast sensor mixed with plasma from healthy patient or diagnosed Alzheimer's patient.

Production of Extract from DNA Amyloid Yeast Cells Device

Extract from three days of cultured yeast cell device was obtained after a process of sonication and filtration (<3 micron), and lyophilization. This extract was mixed with blood plasma (3:1).

Determination of Amyloid Protein in Blood Plasma Samples by Raman Photonic Spectroscopy Raman spectroscopy (RENISHAW INVIA CONFOCAL RAMAN SPECTROMETER, UK) was used to detect the presence of amyloid protein in plasma of patients for each group. Analysis was done for each plasma sample and their corresponding mixture of the DNA amyloid sensor plus plasma. Two replicates per sample were analyzed by Raman spectroscopy. One hundred to two hundred mL plasma samples were used for Raman analysis and compared to amyloid standard. The laser was used at wavelengths between 532 nm-785 nm at 10% laser intensity. Sample intensity and Raman shift (1/cm) were used as a measurement parameter. Results were obtained based on parameters above. Raman intensity is affected by light source intensity, upon $1/\lambda^4$ of source wavelength, concentration of sample or number of molecules, and scattering properties of the sample. All spectra was gathered with a 785 nm excitation laser with 10 sec exposure and 4 acquisitions using a 1 mm quartz cuvette at 25° C. Spectra was processed and analyzed using Bio-Rad KNOWITALL INFORMATICS SYSTEMS 2018.

Determination of Particle Size of the DNA Amyloid Sensor

Purified Amyloid Extract from the DNA amyloid culture was diluted with 500 mmol Tris; concentrations were measured by drying solution in an oven at 55 deg C. for 24 hours. The concentration of the supernatant was determined; 76.25 mg/mL, with which 1×, 2× and 5× solutions with 500 mMol Tris were prepared for measurement. Then, sample of 700 uL of the solution were transferred into a quartz cuvette to be placed in the Malvern Zetasizer Nano, UK for determining the molecular weight of the protein. The Zetasizer instrument is capable of measuring particle and molecular size from less than a nanometer to several microns using dynamic light scattering; zeta potential and electrophoretic mobility using electrophoretic light scattering; and molecular weight using static light scattering.

Determination of Molecular Weight by Centrifugal Device and Gel Electrophoresis

Extract from DNA Amyloid transformed yeast culture was used for determining the molecular weight of the Amyloid protein. Amyloid precursor protein produced in bacteria as fragment (45 kDa) (see above) was used as a control reference. Extract from DNA amyloid yeast culture was produced through different steps including centrifugation for 190 minutes at 9000 rpm, pellet resuspension in nuclease free deionized water, followed by sonication process at different cycles, and centrifugation process. Supernatant from centrifugation was filtered through 0.2 μm or 0.45 μm for the DNA amyloid bacteria culture or DNA amyloid yeast culture, respectively. This extract containing the amyloid protein was subjected to purification.

Purification of Alzheimer Device Protein by Affinity Chromatography (SDS-PAGE)

The purity of the protein was determined by 12% SDS-PAGE gel electrophoresis. SDS-PAGE gel was prepared according to standard method. Twelve percent Acrylamide/Bis Solution (Plus One GE), mixed with Tris-HCl, 0.1% SDS, Ammonium persulfate (APS), Tetramethylethylenediamine (TEMED) was used. For the stacking gel, 5% Acrylamide/Bis solution (Plus One GE), 125 mM Tris-HCl, pH 6.8, 0.1% SDS, 0.05% APS, 0.1% TEMED were used. Then, electrophoresis was performed in running buffer containing 1× Tris-Glycine (25 mM Tris, pH 8.3, 192 mM glycine) and 0.1% SDS. The running conditions were: voltage 70 to 80 V, 400 mA, 30 W.

The proteins were visualized after staining the gel with the dye Coomassie Brilliant Blue R-250 (Amresco), according to the supplier's instructions. The protein bands expressed on the gel were observed and the molecular weight was determined according the molecular weight ladder as standard reference. The eluted fractions were concentrated using Macrosep Advance Centrifugal 30 kDa MWCO and 100 kDa Omega (Pall Corporation) at 2300 rpm for 2 hours at 4° C.

Enhancement of Fluorescence, Using Non-Radioactive Labeling Through Molecular Conjugation This method was carried out using a labeling kit protocol (NHS labeling protocol with the ester of the amino biomolecules Lumiprobe USA), which includes the Cy3 dye to mark the specific side of the amyloid proteins. The following four steps were performed: 1) antibody preparation, 2) mixing antibody with fluorophore, 3) purification of the labeled antibody by a column, and centrifugation at 3800 rpm, 4) reading of the sample in GloMax®-Multi+ Detection System with Instinct™ Software: Base Instrument with shaking (PROMEGA, Madison, Wis. USA) at different fluorescence modules (Green, Blue, UV, AFC, Red).

The advantage of using a marker such as the dye Cy3 is that it naturally bonds without being radio labeled to the targeting protein such as amyloid. Therefore, anytime a source of light comes in contact with this complex (Cy3 dye+DNA extract device), it will emit more fluorescence specific to the protein amyloid that is bonded to the dye.

In Vivo Fluorescence Determination of β-Amyloid in Blood Plasma Samples from Patients Fifty blood plasma samples from different patients were evaluated in the present investigation using the extract of the yeast cell sensor. Fluorescence (FSU) of the DNA β-amyloid sensor was measured in a GloMax Bioanalyzer Detector GloMax®-Multi+ Detection System with Instinct™ Software (Promega, Madison, Wis.) set at the wavelength range of 400-550 nm as a source of excitation. Fluorescence was correlated to the concentration of β-amyloid in blood plasma samples from patients and compared to the criteria of medical diagnosis for Alzheimer's disease. The fluorescence mechanism of the interaction between the source of photonic excitation-emission and the blood plasma sample mixed with the DNA β-amyloid in metals and the extract of the yeast cell sensor is shown in FIG. 10, which is based on the excitation coupled with biophysical emission and biochemical principles.

Alzheimer's patients were divided in three groups (1=Alzheimer's Diagnosed; 2=Pre-Alzheimer's; 3=Normal/Healthy). Blood plasma samples were used from the three different groups of patients according to their ranges of fluorescence and medical diagnosis criteria. All patients in the present investigation were within the age between 57 years-old to 89 years-old.

Samples were analyzed using the extract from the yeast cell sensor mixed with the blood plasma at a volume ratio of 3:1 (extract:blood plasma). The results were then divided in three groups according to the intensity of the fluorescence in relation to the medical diagnosis criteria for Alzheimer's disease as follows: Group 1/Alzheimer's diagnosed=12,800-16,300 FSU; Group 2/Pre-Alzheimer's=11,800-12,800 FSU; and Group 3/Healthy/Asymptomatic=7,700-11,800 FSU. The inherent fluorescence (FSU) of the extract from the yeast sensor (4,000 FSU) was subtracted from the final fluorescence in each sample.

In Vivo Clinical Glycemia Determinations in Blood Plasma Samples from Patients

Levels of glycemia were determined from patient's blood samples, and they were correlated to fluorescence (FSU) and to the clinical medical criteria. Glycemia analysis was also carried out at the clinical laboratory Alvarez-Medina, Cali-Colombia, and at DiagnostiMed Center, Manizales-Colombia. Glycemia analysis was also performed in blood plasma samples from patients following the American Diabetes Association protocol based on the Glucose-Oxidase/Peroxidase-Hexokinase test.

Enhancement of Fluorescence, Using Non-Radioactive Labeling Through Molecular Conjugation This method was carried out using a labeling kit protocol (NHS labeling protocol with the ester of the amino biomolecules Lumiprobe USA), which includes the Cy3 dye to mark the specific side of the amyloid proteins. The following four steps were performed: 1) antibody preparation, 2) mixing antibody with fluorophore, 3) purification of the labeled antibody by a column, and centrifugation at 3800 rpm, 4) reading of the sample in GloMax®-Multi+ Detection System with Instinct™ Software: Base Instrument with shaking (PROMEGA, Madison, Wis. USA) at different fluorescence modules (Green, Blue, UV, AFC, Red)

The advantage of using a marker such as the dye Cy3 is that it naturally bonds without being radio labeled to the targeting protein such as amyloid. Therefore, any time a source of light comes in contact with this complex (Cy3 dye+DNA extract device), it will emit more fluorescence specific to the protein amyloid that is bonded to the dye.

Comparative Analysis Between Fluorescence of the DNA β-Amyloid Sensor and MRI, and Medical Diagnosis
MRI Analysis Although both CT Scan and MRI Analysis were performed in patients, results from MIII are only shown in the denoted paper. CT Scan results (not shown) produced partial comparative results since it was mainly specific Alzheimer's Diagnosed patients, as compared to MRI, showed more specificity across patients. Therefore, MIII analysis was performed following the standard MRI protocol. The analysis was carried out using radiofrequency pulse types Spin-eco and turbo Spin-eco with 1.5 Tesla magnet using GE equipment (Boston, Mass.). Imaging was created based on anatomic differentiation (i.e. T1 and T2) using the three-dimensional phase contrast.

Statistical Analysis

Statistical Analysis was performed to categorize the patients in three groups (Diagnosed Alzheimer's, Pre-Alzheimer's, and Normal), using the Statgraphics Centurion Software version 16.1 (2017 Statgraphics Technologies, Inc., The Plains, Va.). Hence, an analysis of variance (ANOVA) was carried out to determine the mean, standard deviation, variance, correlation (r) between groups, and the type of gender within each group, the effect of age, and the p-value or level of significance of these correlations.

Results
In Vitro Determination of the Effect of Metal Ions on Production of β-Amyloid Protein in Bacterial b-Amyloid Device by ELISA The ELISA results showed a higher concentration of β-amyloid protein in samples of β-amyloid device with higher volume of cells grown in the presence of metal ions as compared to non-transformed $E.\ coli$ cells. The β-amyloid device grown in the presence of metal ions exhibited more yellowish intensity as compared to a non-transformed control (FIG. 13).

A direct correlation exists between the influence of the metal ions and production of β-amyloid protein from the DNA β-amyloid device sensor. A direct correlation exists between the influence of the metal ions and the production of β-amyloid protein from the DNA β-amyloid device sensor. For instance, when the DNA amyloid sensor was grown in aluminum, iron, or copper, the sensor showed higher concentration of amyloid (200, 100, and 100 μg/ml, respectively) as compared to control (i.e., cells without the DNA amyloid sensor), which showed negligible amyloid production.

Determination of β-Amyloid Protein in Patient Blood Plasma Samples Using Western Blot Results from Western blot analysis showed bands with stronger intensity in the sample of a patient with high β-amyloid fluorescence (>158,000 FSU) and clinically reported with Alzheimer's symptoms as compared to a sample from a healthy patient (900 FSU) (FIG. 14A). Similar results were obtained for plasma samples mixed with extract of DNA amyloid yeast sensor, in which the sample from diagnosed Alzheimer's patient with higher fluorescence (12800 FSU) showed higher expression of the protein as compared to Healthy with lower fluorescence (10500 FSU). (FIG. 14B)

In Vitro Test of Fluorescence of DNA β-Amyloid Device Sensor

Results showed higher fluorescence of the DNA β-amyloid sensor at different dilutions as compared to control (non-transformed $E.\ coli$ or extract from the yeast cell sensor). A similar correlation was shown by the control sensor but with lower fluorescence (FSU).

In Vivo Clinical Alzheimer's Determination as Compared to Fluorescence in Blood Plasma from Patients The presence of β-amyloid protein was measured in vivo using human blood plasma samples. The results showed a direct correlation between higher fluorescence of β-amyloid and the medical report, which is based on the following criteria: 1. memory loss, and 2. cognitive impairment (e.g., mental disorientation, and/or mental confusion), as compared to a healthy patient. Hence, the Alzheimer's diagnosed Group 1 was directly correlated with the two criteria mentioned above, while the pre-Alzheimer's Group 2 showed correlation to one of the above-mentioned criteria, and in some cases could be asymptomatic as compared to control Group 1 that is asymptomatic. Plasma samples mixed with yeast extract exhibited high fluorescence intensity. This intensity was enhanced more than 10 fold when both the mixture of plasma plus the extract of the DNA amyloid sensor was labeled with non-radioactive Cy3 dye, after conjugation (Table 12), as compared to samples of the mixture that were not labeled. Hence, Group 1 or Alzheimer's diagnosed showed the highest fluorescence intensity (mean=158,100 FSU), as compared to non-labeled (mean=13,800 FSU); Group 2 or pre-Alzheimer's, which showed the second highest fluorescence intensity (mean=127,700 FSU), as compared to non-labeled (mean=10,500 FSU); followed by Group 3 or control/ healthy/asymptomatic having the lowest fluorescence intensity (Mean=82,200 FSU), as compared to non-labeled (mean=10,500 FSU). The pre-Alzheimer's Group 2 exhibited a mean of 127,700 FSU that was between the diagnosed Alzheimer's Group 1 and the healthy Group 3. Samples from women showed the highest β-amyloid fluorescence in Group 1 (140,000-183,600 FSU) (Table 1). In Group 2 (pre-Alzheimer's) the level of fluorescence was equally distributed amongst both genders. The β-amyloid sensor produced higher β-amyloid fluorescence in plasma samples in both genders. Group 1 showed higher β-amyloid fluorescence with patients between the age range of 70-89 years-old as compared to Group 2 patients, which showed lower amyloid fluorescence between the age range between 57-78 years-old. The variability of the level of fluorescence intensity was noticeable within the range of the Alzheimer's diagnosed Group 1 as compared to the pre-Alzheimer's Group 2 and healthy Group 1, which showed less variability within their narrower range.

Although glycemic expression was used as a parameter to correlate the expression of β-amyloid device fluorescence, there was no direct correlation between β-amyloid samples from Alzheimers' patient's glycemia levels with the yeast extract.

TABLE 12

Comparative results between fluorescence of the DNA bacterial cell □-Amyloid sensor mixed with patient blood plasma, MRI, and medical diagnosis analysis. This table confirms the efficacy of using fluorescence of blood plasma for diagnosing Alzheimer's symptoms when compared to invasive conventional diagnostic methods such as MRI.

| Patient | Gender | Age | Conjugation Fluorescence (FSU) | Medical Diagnosis | MRI | Glycemia (mg/dL) |
|---|---|---|---|---|---|---|
| \multicolumn{7}{c}{Group 1: Alzheimer's diagnosed} |
| 12 | Female | 77 | 151200 | Cognitive impairment (Disorientation, Mental Confusion) and Memory Loss | Sulci widening. Dilatation of the ventricular system, hippocampal atrophy | 84 |
| 68 | Female | 63 | 143000 | Cognitive impairment (Disorientation, Mental Confusion) and Memory Loss | Sulci widening. Dilatation of the ventricular system, hippocampal atrophy | 102 |
| 59 | Female | 85 | 140000 | Cognitive impairment (Disorientation, Mental Confusion) and Memory Loss | Sulci widening. Dilatation of the ventricular system, hippocampal atrophy | 101 |
| 67 | Female | 75 | 152300 | Cognitive impairment (Disorientation, Mental Confusion) and Memory Loss | Sulci widening. Dilatation of the ventricular system, hippocampal atrophy | 96 |
| 3 | Male | 76 | 161000 | Cognitive impairment (Disorientation, and Mental Confusion) | Prominence of ventricular system and. Sulci widening | 87 |
| 9 | Female | 72 | 143800 | Cognitive impairment (Disorientation, and Mental Confusion) and Memory Loss | Prominence of ventricular system and. sulci widening | 91 |
| 69 | Male | 80 | 143200 | Cognitive impairment (Disorientation, Mental Confusion) and Memory Loss | Sulci widening. Dilatation of the ventricular system, hippocampal atrophy | 110 |
| 38 | Male | 75 | 164000 | Cognitive impairment (Disorientation, and Mental Confusion) and Memory Loss | Sulci widening. Dilatation of the ventricular system, hippocampal atrophy | 75 |
| 8 | Female | 89 | 139300 | Cognitive impairment (Disorientation, and Mental Confusion) and Memory Loss | Sulci widening and hippocampal atrophy | 86 |
| 34 | Male | 80 | 186000 | Cognitive impairment (Disorientation, and Mental Confusion) | Sulci widening. Dilatation of the ventricular system, hippocampal atrophy | 91 |
| 61 | Male | 80 | 146300 | Disorientation and Memory Loss | Sulci widening. Dilatation of the ventricular system, hippocampal atrophy | 80 |

TABLE 12-continued

Comparative results between fluorescence of the DNA bacterial cell □-Amyloid sensor mixed with patient blood plasma, MRI, and medical diagnosis analysis. This table confirms the efficacy of using fluorescence of blood plasma for diagnosing Alzheimer's symptoms when compared to invasive conventional diagnostic methods such as MRI.

| Patient | Gender | Age | Conjugation Fluorescence (FSU) | Medical Diagnosis | MRI | Glycemia (mg/dL) |
|---|---|---|---|---|---|---|
| 41 | Male | 84 | 199500 | Cognitive impairment (Disorientation, and Mental Confusion) and Memory Loss | Sulci widening. Dilatation of the ventricular system, hippocampal atrophy | 93 |
| 40 | Male | 78 | 140000 | Cognitive impairment (Disorientation, and Mental Confusion) and Memory Loss | Sulci widening. Dilatation of the ventricular system, hippocampal atrophy | 89 |
| 10 | Male | 67 | 156700 | Cognitive impairment (Disorientation, Mental Confusion) and Memory Loss | Sulci widening. Dilatation of the ventricular system, hippocampal atrophy | 87 |
| 48 | Female | 76 | 149500 | Mental confusion and Memory Loss | Sulci widening. Dilatation of the ventricular system, hippocampal atrophy | 86 |
| 4 | Female | 78 | 163400 | Cognitive impairment (Disorientation, and Mental Confusion) and Memory loss | Sulci widening. Dilatation of the ventricular system, hippocampal atrophy | 88 |
| 63 | Female | 75 | 140000 | Cognitive impairment (Disorientation, and Mental Confusion) and Memory loss | Sulci widening. Dilatation of the ventricular system, hippocampal atrophy | 98 |
| 2 | Female | 77 | 141200 | Cognitive impairment (Disorientation, and Mental Confusion) | Sulci widening, dilatation of the ventricular system, hippocampal atrophy | 87 |
| 6 | Female | 86 | 183600 | Cognitive impairment (Disorientation, and Mental Confusion) and Memory loss | Sulci widening. Dilatation of the ventricular system, hippocampal atrophy | 89 |
| Total Mean +/− SD | | | 158100 +/− 18700 | | | |
| Group 2: Pre- Alzheimer's | | | | | | |
| 13 (2) | Male | 57 | 124300 | Asymptomatic | Hippocampal atrophy | 81 |
| 7 (2) | Female | 78 | 137500 | Memory Loss | Sulci widening | 82 |
| 5 (2) | Female | 75 | 117100 | Cognitive impairment | Sulci widening and hippocampal atrophy | 75 |
| 47 | Male | 66 | 139500 | Memory Loss | Dilatation of the ventricular system and hippocampal atrophy | 95 |
| 53 | Female | 69 | 136600 | Disorientation and memory loss | Dilatation of the ventricular system and hippocampal atrophy | 83 |
| 32 (2) | Female | 62 | 139000 | Cognitive impairment | Bilateral frontal atrophy. | 85 |
| 54 | Female | 77 | 125300 | Memory Loss | Sulci widening and slightly hippocampal atrophy | 93 |
| 56 | Male | 67 | 116800 | Disorientation and memory loss | Sulci widening and hippocampal atrophy | 95 |

TABLE 12-continued

Comparative results between fluorescence of the DNA bacterial cell □-Amyloid sensor mixed with patient blood plasma, MRI, and medical diagnosis analysis. This table confirms the efficacy of using fluorescence of blood plasma for diagnosing Alzheimer's symptoms when compared to invasive conventional diagnostic methods such as MRI.

| Patient | Gender | Age | Conjugation Fluorescence (FSU) | Medical Diagnosis | MRI | Glycemia (mg/dL) |
|---|---|---|---|---|---|---|
| 53 | Female | 75 | 114200 | Memory Loss | Dilatation of the ventricular system | 87 |
| 55 | Male | 71 | 128000 | Memory Loss | Sulci widening. Dilatation of the ventricular system, hippocampal atrophy | 105 |
| 33 | Male | 66 | 123500 | Cognitive impairment (Disorientation, and Mental Confusion) | Sulci widening. Dilatation of the ventricular system and Slightly hippocampal atrophy | 123 |
| 50 | Female | 70 | 117300 | Asymptomatic | Dilatation of the ventricular system, hippocampal atrophy | 80 |
| Total mean +/− SD | | | 127700 +/− 9036 | | | |
| Group 3: Healthy | | | | | | |
| 37 | Male | 80 | 103800 | Healthy | Not signs for Alzheimer disease | 84 |
| 46 | Male | 71 | 74600 | Healthy | Without alterations | 94 |
| 62 | Female | 74 | 105400 | Healthy | Without alterations | 87 |
| 66 | Male | 68 | 89390 | Healthy | Without alterations | 100 |
| 42 | Female | 74 | 105800 | Memory loss | Without alterations | 88 |
| 1 (2) | Female | 61 | 31000 | Healthy | Without alterations | 97 |
| 64 | Male | 72 | 59670 | Healthy | Without alterations | 90 |
| 36 | Male | 63 | 104200 | Healthy | Without alterations | 87 |
| 44 | Female | 80 | 109300 | Disorientation | Without alterations | 86 |
| 60 | Female | 59 | 78000 | Healthy | Without alterations | 87 |
| 58 | Female | 66 | 44900 | Healthy | Without alterations | 95 |
| 35 | Female | 65 | 65820 | Healthy | Without alterations | 92 |
| 57 | Female | 62 | 60950 | Healthy | Without alterations | 84 |
| 43 | Female | 75 | 106700 | Healthy | Without alterations | 87 |
| 49 | Female | 71 | 60300 | Healthy | Without alterations | 89 |
| 51 | Male | 79 | 72800 | Healthy | Without alterations | 105 |
| 45 | Female | 74 | 98000 | Healthy | Without alterations | 103 |
| 39 | Female | 75 | 110000 | Healthy | Without alterations | 91 |
| 65 | Male | 77 | 80028 | Healthy | Without alterations | 115 |
| Total mean +/− SD | | | 82200 +/− 23970 | | | |

Note 1:
FSU = Fluorescence Units, MRI = Magnetic Resonance Imaging
Note 2:
The fluorescence of the extract alone (4000 FSU) was subtracted from each sample fluorescence
Note 3:
MRI criteria used in investigation were: 1) Sulci widening, 2) Dilatation of the ventricular system, and 3) hippocampal atrophy. However, in some cases other related MRI criteria was used "bilateral frontal atrophy". This was applied on a Pre- Alzheimer's patients.
Note 4:
Medical Diagnosis criteria used was: A) Cognitive impairment (Mental concussion and/or disorientation); B) Memory Loss
Note 5:
Asymptomatic = no symptoms Determination of Amyloid Protein in Blood Plasma Samples by Raman Photonic Spectroscopy Results of the Raman analysis show that intensity and the shift value of the amyloid protein correlate with the peaks of the sample but the range size depended on the type of patient group and type of sample (i.e. plasma alone, or plasma+ extract of DNA amyloid sensor). Thus, the range for the standard amyloid protein was between 600 to 1800 $cm^{-1}$, which corresponds to the different molecules including tyrosine (800 $cm^{-1}$), phenylalanine (1000 $cm^{-1}$), tyrosine-phenyl (1100 $cm^{-1}$), amide I (1500 $cm^{-1}$), amide II (1600 $cm^{-1}$), amide III (1200-1300 $cm^{-1}$). For instance, for plasma plus extract of DNA amyloid sensor, the range of the fingerprint was similar to the range of the plasma alone. However, the number of peaks of the plasma plus extract was higher (10 peaks) for group 1, followed by group 2 (8 peaks) and group 3 (6 peaks). The intensity varied according to the group in which group 2 showed the highest intensity (FIGS. 14A-C) while for plasma alone, group 1 showed 7-8 peaks similar to the standard amyloid with the highest intensity (>2000 $cm^{-1}$). Group 2 showed 8 peaks with lower intensity (approximately 1,000 $cm^{-1}$), and group 3 showed 5-6 peaks and the lowest intensity (600 $cm^{-1}$) (data not showing due to large size of the figure), but it only showed one peak specific for amyloid protein, with the other 3 peaks related to an amide compound (i.e. 1200-1600 $cm^{-1}$) common to any protein analyzed by Raman spectroscopy.

Determination Particle Size of the DNA Amyloid Sensor

Figure 16A:
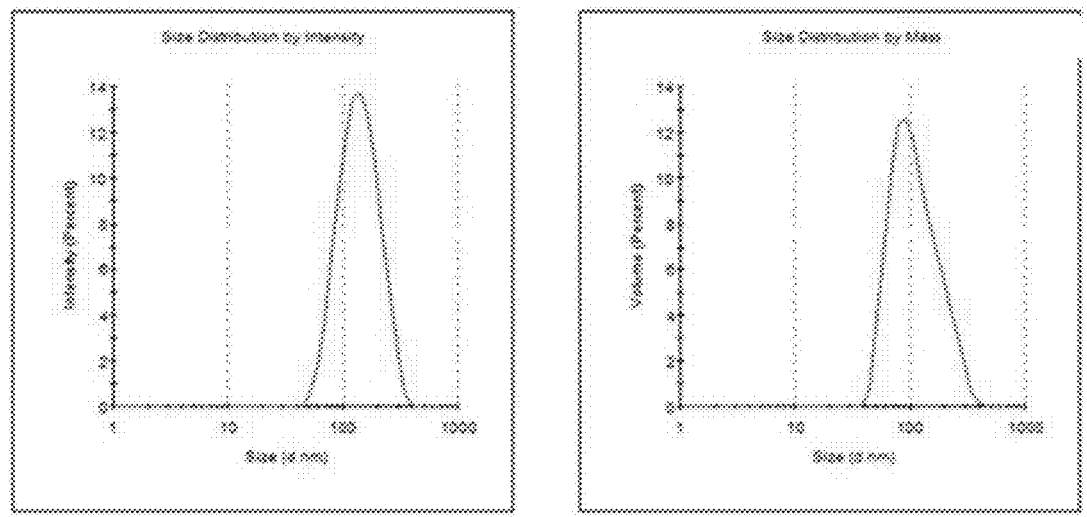
FIGS. 16A-B show both the DNA amyloid sensor and the control of synthesized amyloid protein, showed close particle size, 124 nm and 95 nm, respectively.
Figure 16B:
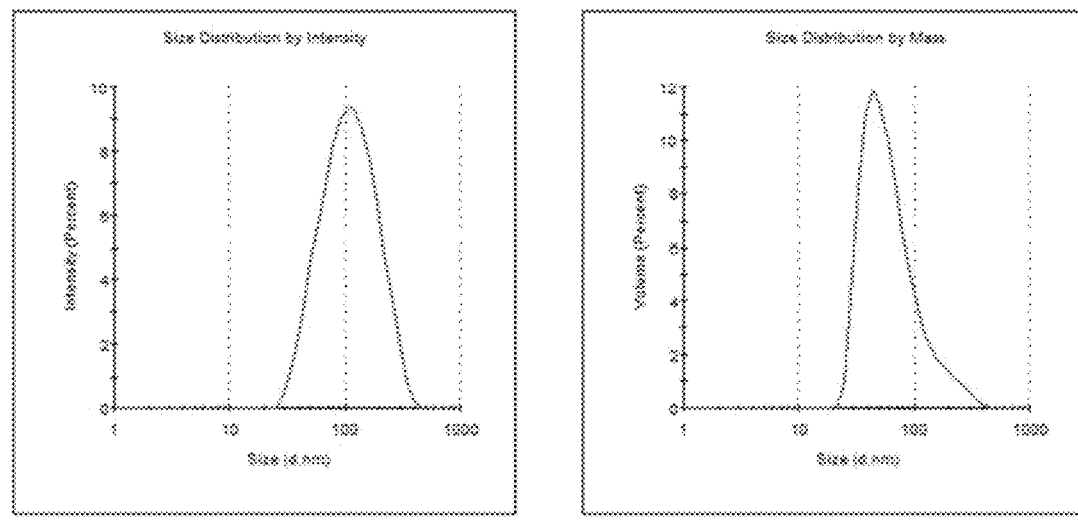

Both the DNA amyloid sensor and the control of synthesized amyloid protein, showed close particle size, 124 nm and 95 nm, respectively (FIGS. 16A-B). Results are provided below for each sample.

Amyloid Sensor Extract

| Sample Details | |
|---|---|
| Record Number: | 5 |
| Temperature (° C.): | 25.0 |
| Derived Count Rate (kcps): | 223.6 |
| Intercept: | 0.967 |

| Hydrodynamic Radius | | | |
|---|---|---|---|
| Z-Average (±SD) (d · nm): | 124.4 ± 45.24 | Estimated MW (±SD) (KDa): | 5.30e4 ± 1.93e+04 |
| Polydispersity Index: | 0.132 | % Polydispersity: | 36.4 |
| | | Sample Polydispersity: | Polydisperse |

| Distribution Results | | | | | | |
|---|---|---|---|---|---|---|
| | Mode ± SD (nm) | % Pd | Est. MW (KDa) (Mean ± SD)* | % Intensity | % Mass | Peak Polydispersity |
| Peak 1: | 141.8 ± 57.00 | 39.2 | 7.63e+4 ± 2.99e+4 | 100.0 | 100.0 | Polydisperse |
| Peak 2 | 0.000 ± 0.000 | 0 | 0.0 ± 0.0 | 0.0 | 0.0 | |
| Peak 3: | 0.000 ± 0.000 | 0 | 0.0 ± 0.0 | 0.0 | 0.0 | |

Control

| Sample Details | |
|---|---|
| Record Number: | 129 |
| Temperature (° C.): | 25.0 |
| Derived Count Rate (kcps): | 179.1 |
| Intercept: | 0.790 |

| Hydrodynamic Radius | | | |
|---|---|---|---|
| Z-Average (±SD) (d · nm): | 95.97 ± 64.88 | Estimated MW (±SD) (KDa): | 2.89e4 ± 1.95e+04 |
| Polydispersity Index: | 0.457 | % Polydispersity: | 67.6 |
| | | Sample Polydispersity: | Polydisperse |

| Distribution Results | | | | | | |
|---|---|---|---|---|---|---|
| | Mode ± SD (nm) | % Pd | Est. MW (KDa) (Mean ± SD)* | % Intensity | % Mass | Peak Polydispersity |
| Peak 1: | 105.7 ± 65.78 | 53.8 | 5.08e+4 ± 2.74e+4 | 93.8 | 92.2 | Polydisperse |
| Peak 2 | 5560 ± 721.0 | 15.0 | 2.75e+8 ± 4.11e+7 | 6.2 | 7.8 | Monodisperse |
| Peak 3: | 0.000 ± 0.000 | 0 | 0.0 ± 0.0 | 0.0 | 0.0 | |

Determination of Molecular Weight of the DNA Amyloid Sensor

Figure 17:
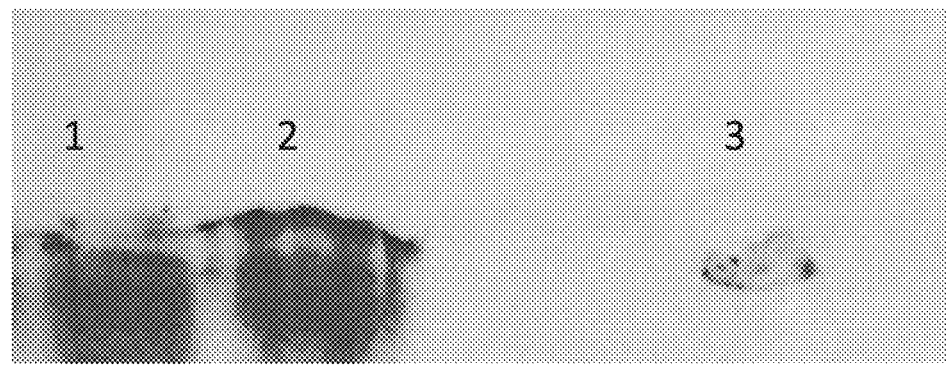
FIG. 17 shows the SDS-PAGE Protein Purification of Alzheimer Device Extract. 1. Alzheimer Device extract concentrated by filter 30K. 2. Alzheimer Device extract concentrated by filter 100K. 3. Standard Beta Amyloid Protein. The purified protein in the extract is larger than 100 KDa.

The extract from DNA amyloid yeast culture showed production of amyloid protein after filtration in centrifugal devices within the range of 30 to 100 kDa as well as in gel electrophoresis (FIG. 17 lane 1, 2, and 3). However, sample extracts from DNA amyloid yeast exhibit the highest and strongest molecular weight as also shown by the thickness and brightness of the bands in the gel electrophoresis (FIG. 17 lanes 1 and 2), as compared to the control reference fragments which showed lighter brightness and weaker bands (FIG. 17 lane 3).

Figure 18A:
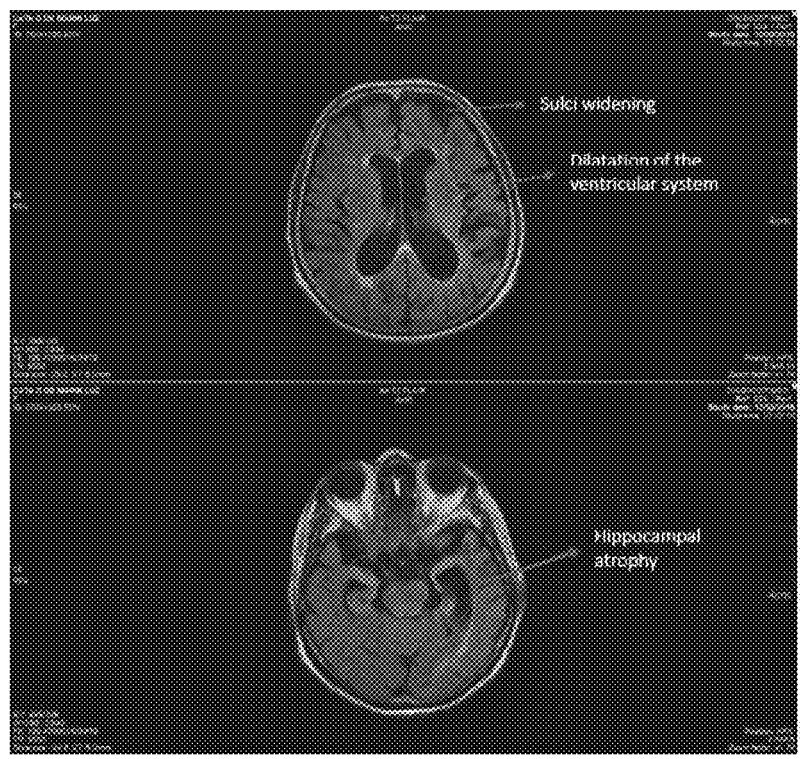
FIG. 18A shows comparative Mill results from patients clinically diagnosed with Alzheimer's versus healthy patients, using extract of yeast DNA b-Amyloid sensor.
Figure 18B:
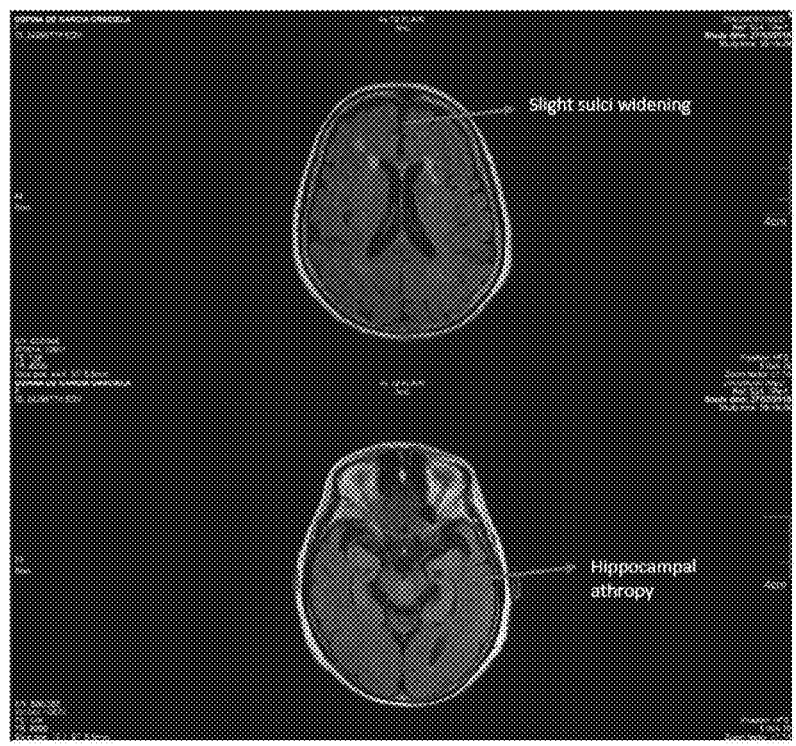
FIG. 18B shows the Mill of pre-Alzheimers patient (5) using extract of yeast DNA b-Amyloid sensor.
Figure 18C:
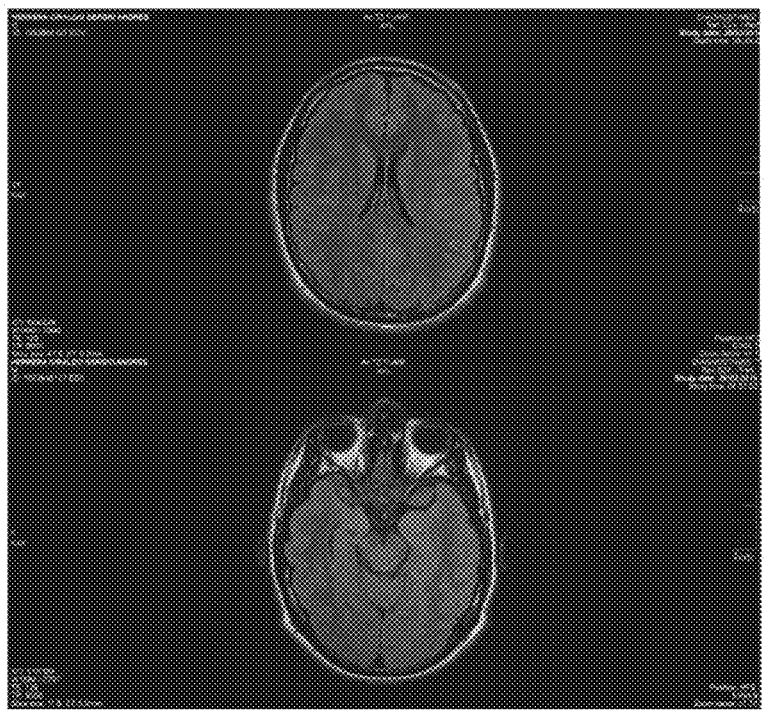
FIG. 18C shows the MM of a healthy patient without encephalic alterations (24) using extract of yeast DNA b-Amyloid sensor

Comparative Results Between Fluorescence of the DNA β-Amyloid Sensor Mixed with Patient Blood Plasma, and MRI, and Medical Diagnosis The comparative results between fluorescence produced by the β-amyloid sensor with MRI and medical diagnosis from patients in all three groups showed good correlation (Table 1) (FIGS. 18A-C), which confirms the efficacy of the β-amyloid sensor for detecting β-amyloid protein. These results also confirm the reliability of our classification of the three groups (i.e. Alzheimer's Diagnosed, Pre-Alzheimer's, and Normal) based on the intensity of the fluorescence. The correlation was very strong between the fluorescence and the two medical diagnosis criteria (1. memory loss and 2. cognitive impairment such as mental disorientation, and/or mental confusion) according to the group's classification. This strong correlation was followed by the comparative results of the conventional MRI analysis. The two conventional diagnostic methods described herein (i.e. MRI, and medical diagnosis) all correlated well with our fluorescence results based on the constructed β-amyloid sensor when used with healthy and/or non-Alzheimer's patients.

Statistical Analysis

Results showed that the three groups were well categorized based on the three selected parameters. Group 1 showed the highest fluorescence total mean (154947.37+/−18,700 FSU) followed by Group 2 (127,700+/−9036), as compared to Group 3, which exhibited the lowest total mean (82,200+/−23,970) (Table 1). The identification of these groups showed a good level of significance ($\alpha$=0.05) and correlation variance (P=1.519*E−7) (Table ??). Also, the effect of sex per group and within each group showed a strong positive correlation Pearson coefficient (R) and a significant p-value, but a positive weak correlation for age.

DISCUSSION

There is a direct correlation between the fluorescence produced by the β-amyloid sensor and the concentration of β-amyloid protein when tested in vitro and in vivo. The fluorescence of the extract produced by the yeast cells transformed with the DNA construct mixed with blood plasma confirms the suitability of the extract for detecting amyloid proteins in human blood plasma due to the fact that both yeast and human cells are eukaryotic cells. The high variability of the fluorescence within the Alzheimer's diagnosed Group 1 as compared to less variability within the ranges of the pre-Alzheimer's Group 2 and control/healthy Group 3 is perhaps due to associated factors such as heritage and/or environmental (e.g., metal ions) that are influencing the onset of Alzheimer's disease. However, Group 1 showed higher fluorescence for female than male, as compared to Groups 2 and 3 where there was no difference. This could be due to other unknown associated factors expressed during the onset of the disease related to women's physiology. Age showed weak positive correlation in Groups 1 ($r=0.096$) and 2 ($r=0.155$) and a weak negative correlation in Group 3 ($r=-0.0687$). Perhaps, this is because all three groups are within the same close range of age; age is still important with the development of the disease, and the negative value of Group 3 (Healthy) corroborates the good categorization of the groups.

The fluorescence mechanism is based on excitation and emission of photons [19] at the molecular level as illustrated in FIG. 10. This was further confirmed at the cellular level when β-amyloid sensor device cells were grown in media containing different metals ($Fe^{2+}$, $Cu^{2+}$, $Al^{2+}$, and $Zn^{2+}$) as compared to controls of non-transformed cells. A previous report also using fluorescence to detect glucose for early diagnosis of diabetes suggests a similar hypothetical mechanism.

The Raman spectroscopy analysis, which is based on photonicity, confirmed not only the presence of the amyloid protein in the plasma sample but also the efficacy of the DNA amyloid sensor to diagnose Alzheimer's according to its level (Alzheimer's diagnosed, Pre-Alzheimer's and Healthy) before the onset of the disease.

Also, the DNA amyloid sensor exhibited a particle size similar to the control synthesized amyloid protein, which confirms the atomic similarity between the two molecules. This is also corroborated by the similarity of molecular weight between the two molecules when analyzed by SDS-PAGE Electrophoresis. The slight difference in numbers of the particle size between the Amyloid sensor (124 nm) and the control synthetic amyloid protein (95 nm) is perhaps due to the purity of the chemically synthesized amyloid protein as compared to the DNA amyloid yeast device that might have small associated proteins or other compounds, which costs interference the photonicity, as it always occurs with biomolecules.

Additionally, the influence of metals such as iron on the expression of β-amyloid was corroborated by the sensitive ELISA test. The expression of β-amyloid has been previously demonstrated by other authors using the ELISA method for cerebrospinal fluid. These results demonstrate the influence of metals on the expression of β-amyloid proteins, which suggests a possible effect of metals at the molecular level for triggering Alzheimer's disease. Perhaps this correlation was facilitated by the presence of both a riboswitch and an iron ion channel (TonB) in the β-amyloid sensor. Another report also corroborates the effective function of iron ion channels and riboswitches in DNA metal sensors.

The results herein suggest that the medical criteria outlined above were not sufficient to identify the symptoms for the disease at the time when the patients were examined. Medical diagnosis in this instance is performed using subjective methods based on observation and questioning and not on physical testing and/or molecular (biomarker) identification. However, the β-amyloid sensors can provide more specific and/or stronger criteria for diagnosing Alzheimer's disease since it is based on a more universal molecule or biomarker such as a protein. Therefore, the diagnosis of Alzheimer's disease can be more objective based on the presence of targeted molecules such as β-amyloid protein.

The sensitivity and accuracy of the β-amyloid sensor for detecting β-amyloid in relation to Alzheimer's disease is due to the fluorescence produced by the sensor, which is based on photon emission at the molecular and atomic levels that ultimately provide more specific detection. The photonic detection provides a definite advantage for detection of the disease. However, the photon effect can be subject to some variations due to the fact that photonic detection of amyloid protein is based on the energy of quanta taken up by one mole of molecules.

However, the intensity of the fluorescence can vary when the molar concentration of the substrate is high, which causes photonic interference. Consequently, a yield of the photonics quantum can be determined in order to obtain the full photonic effect.

Specific wavelengths were used to induce fluorescence of the β-amyloid sensor when mixed with plasma samples to determine concentration of β-amyloid protein. The photon is the mediator for any type of electromagnetic interaction. The photon has no mass or charge and is responsible for producing all electric and magnetic fields. The photons interact with the electron cloud formed by the bonds of the molecules and produce a vibratory effect that is used for the detection, identification and characterization of biological molecules.

Hence, the photonics effect is shown by emission of fluorescence, where intensity represents the presence of the biomolecules such as amyloid protein. Using the β-amyloid sensor, we were able to identify three distinct groups of patients with clear symptoms and/or without symptoms.

The high sensitivity of the β-amyloid sensor was also corroborated by Western blot test, which showed higher correlation between concentrations of β-amyloid protein and fluorescence in blood plasma samples.

Finally, the inconsistent correlation between the level of glycemia and fluorescence units (FSU) during the detection of β-amyloid protein using the β-amyloid sensor in blood plasma could be explained by the lack of affinity of the units of the measurement parameters between the two analyses. Thus, glycemia levels are measured based on mass of glucose, while fluorescence is based on energy (photon units).

The quantification of fluorescence produced using the sensor and extracts produced herein is a reliable and more practical diagnostic method as demonstrated and confirmed by other sensitive conventional technologies such as Mill and medical diagnostic parameters. Although MM is a useful anatomical expression of Alzheimer's, it is not always able to fully predict the disease. Also, tomography does not always capture small damages at the cellular level. For instance, the intensity inhomogeneity, and the segmentation of the magnetic resonance imaging are not always accurate. Additionally, the advance state of the disease might affect the condition of the cells, as we have noticed in the denote investigation. Therefore, the sensitivity for early detection of the disease can be diminished.

The reliability of the β-amyloid sensor is perhaps due to the inherent bioluminescence of the DNA β-amyloid sensor that is compatible with the blood plasma at the molecular level regardless of the type of amyloid isoform.

The β-amyloid sensor described herein detects the amyloid protein regardless of the types of isoforms that are transported through the blood-brain barrier (BBB). The inherent bioluminescence/fluorescence properties of the sensor provides a wider range of sensitivity. This can be explained based on the active transport in the BBB. During transmembrane transport, different amyloid isoforms form that have similar chemical structures. Our β-amyloid sensor will be able to detect different isoforms. One of the main advantages in constructing the β-amyloid sensors by synthetic biology for early detection of Alzheimer's disease in blood is the assemblage of exons that are specific sequences for targeting specific proteins. Thus, the production and the expression of the amyloid protein can be more specific.

Throughout this application, various publications are referenced. The disclosures of these publications in their entireties are hereby incorporated by reference into this application in order to more fully describe the compounds, compositions, and methods described herein.

Various modifications and variations can be made to the compounds, compositions, and methods described herein. Other aspects of the compounds, compositions, and methods described herein will be apparent from consideration of the specification and practice of the compounds, compositions, and methods disclosed herein. It is intended that the specification and examples be considered as exemplary.

What is claimed:

1. A vector comprising a DNA construct comprising the following genetic components:
   (a) a gene that encodes amyloid precursor protein having SEQ ID NO. 3 or at least 90% homology thereto,
   (b) a gene that encodes transferrin having SEQ ID NO. 5 or at least 90% homology thereto;
   (c) a gene that encodes TonB having SEQ ID NO. 6 or at least 90% homology thereto;
   (d) a gene that encodes β-amyloid receptor having SEQ ID NO. 8 or at least 90% homology thereto; and optionally
   (e) a gene that encodes a reporter protein;
   wherein the vector is a pYES2, pBKSII, or pETDuet-1 plasmid.

2. The vector of claim 1, further comprising a gene that encodes a riboswitch.

3. The vector of claim 2, wherein the gene that encodes the riboswitch has SEQ ID NO. 2 or at least 90% homology thereto.

4. The vector of claim 1, wherein the vector comprises a promoter, and wherein the promoter is a T3 promoter, a T7 promoter, an iron promoter, or a GAL1 promoter.

5. The vector of claim 1, wherein the vector comprises the gene that encodes a reporter protein.

6. The vector of claim 1, wherein the vector further comprises a gene that encodes a riboswitch and an iron promoter.

7. The vector of claim 1, wherein the vector comprises from 5' to 3' the following genetic components in the following order: (a) the gene that encodes amyloid precursor protein, (b) the gene that encodes transferrin, and (c) the gene that encodes TonB.

8. The vector of claim 1, wherein the vector comprises from 5' to 3' the following genetic components in the following order: (a) a gene that encodes a riboswitch, (b) the gene that encodes amyloid precursor protein, (c) the gene that encodes transferrin, and (d) the gene that encodes TonB.

9. The vector of claim 1, wherein the vector comprises from 5' to 3' the following genetic components in the following order: (a) a gene that encodes a riboswitch, (b) the gene that encodes amyloid precursor protein, (c) the gene that encodes transferrin, (d) an iron promoter, and (e) the gene that encodes TonB.

10. The vector of claim 1, wherein the vector comprises (a) the gene that encodes β-amyloid receptor, (b) the gene that encodes amyloid precursor protein, (c) the gene that encodes transferrin, (d) the gene that encodes TonB, (e) a gene that encodes a riboswitch, and (f) an iron promoter.

11. The vector of claim 1, wherein the vector comprises from 5' to 3' the following genetic components in the following order: (a) the gene that encodes β-amyloid receptor, (b) the gene that encodes amyloid precursor protein, (c) the gene that encodes transferrin, and (d) the gene that encodes TonB.

12. The vector of claim 1, wherein the vector comprises from 5' to 3' the following genetic components in the following order: (a) the gene that encodes β-amyloid receptor, (b) a gene that encodes a riboswitch, (c) the gene that encodes amyloid precursor protein, (d) the gene that encodes transferrin, and (e) the gene that encodes TonB.

13. The vector of claim 1, wherein the vector comprises from 5' to 3' the following genetic components in the following order: (a) the gene that encodes β-amyloid receptor, (b) a gene that encodes a riboswitch, (c) the gene that encodes amyloid precursor protein, (d) the gene that encodes transferrin, (e) an iron promoter, and (f) the gene that encodes TonB.

14. The vector of claim 1, wherein the vector comprises (a) the gene that encodes β-amyloid receptor, (b) the gene that encodes amyloid precursor protein, (c) the gene that encodes transferrin, (d) the gene that encodes TonB, and (e) an iron promoter.

15. The vector of claim 1, wherein the vector comprises from 5' to 3' the following genetic components in the following order: (a) a ribosomal binding site, (b) the gene that encodes β-amyloid receptor, (c) a ribosomal binding site, (d) the gene that encodes amyloid precursor protein, (e) a ribosomal binding site, (f) an iron promoter, (g) a ribosomal binding site, (h) the gene that encodes transferrin, (i) a ribosomal binding site, and (j) the gene that encodes TonB.

16. The vector of claim 1, wherein the vector comprises from 5' to 3' the following genetic components in the following order: (a) a ribosomal binding site, (b) the gene that encodes β-amyloid receptor, (c) a T7 promoter, (d) a LAC operon, (e) a ribosomal binding site, (f) the gene that encodes amyloid precursor protein, (g) a ribosomal binding site, (h) an iron promoter, (i) a ribosomal binding site, (j) the gene that encodes transferrin, (k) a ribosomal binding site, and (l) the gene that encodes TonB.

17. A biological device comprising host cells transformed with the vector of claim 1.

18. An extract produced by culturing the biological device of claim 17.

19. A method for diagnosing or predicting a disease associated with elevated levels of amyloid in a subject, the method comprising the steps of:
   (a) mixing a sample from the subject with an extract of claim 18 to produce a test sample; and
   (b) measuring the fluorescence intensity of the test sample.

20. The method of claim 19, wherein the sample comprises blood, serum, plasma, saliva, spinal fluid, or urine.

21. The method of claim 19, wherein after step (b) correlating the amount of fluorescence to determine if the subject (1) has the disease or (2) is predisposed to the disease.

22. The method of claim 19, wherein the disease is Alzheimer's disease, Lewy body dementia, inclusion body myositis, chronic traumatic encephalopathy, or cerebral amyloid angiopathy.

23. The method of claim 19, wherein the disease is caused by trauma to the brain or cancer.

* * * * *